US012559560B2

(12) United States Patent
Holland et al.

(10) Patent No.: US 12,559,560 B2
(45) Date of Patent: Feb. 24, 2026

(54) ANTIBODY-BASED COMPOSITIONS FOR TARGETING TROPOMYOSIN RECEPTOR KINASE B (TrkB) ISOFORMS

(71) Applicant: Fred Hutchinson Cancer Center, Seattle, WA (US)

(72) Inventors: Eric Holland, Seattle, WA (US); Siobhan Pattwell, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 781 days.

(21) Appl. No.: 17/759,665

(22) PCT Filed: Jan. 29, 2021

(86) PCT No.: PCT/US2021/015699
§ 371 (c)(1),
(2) Date: Jul. 28, 2022

(87) PCT Pub. No.: WO2021/155141
PCT Pub. Date: Aug. 5, 2021

(65) Prior Publication Data
US 2023/0103618 A1 Apr. 6, 2023

Related U.S. Application Data

(60) Provisional application No. 63/036,301, filed on Jun. 8, 2020, provisional application No. 62/967,978, filed on Jan. 30, 2020.

(51) Int. Cl.
*C07K 16/28* (2006.01)
*G01N 33/574* (2006.01)

(52) U.S. Cl.
CPC ....... *C07K 16/2863* (2013.01); *G01N 33/574* (2013.01); *C07K 2317/14* (2013.01); *C07K 2317/24* (2013.01); *C07K 2317/34* (2013.01); *C07K 2317/55* (2013.01); *C07K 2317/565* (2013.01); *C07K 2317/622* (2013.01); *G01N 2333/912* (2013.01)

(58) Field of Classification Search
None
See application file for complete search history.

(56) References Cited

U.S. PATENT DOCUMENTS

| | | | |
|---|---|---|---|
| 5,877,016 A | 3/1999 | Presta et al. | |
| 2005/0112139 A1* | 5/2005 | Karp | A61P 37/00 |
| | | | 424/188.1 |
| 2007/0059304 A1 | 3/2007 | Cho et al. | |
| 2019/0161551 A1* | 5/2019 | Croll | C07K 16/2863 |

FOREIGN PATENT DOCUMENTS

WO 2015127158 A1 8/2015

OTHER PUBLICATIONS

Almagro et al. Frontiers in Bioscience 13:1619-1633, 2008.*
Edwards et al J.. Mol. Biol. (2003) 334, 103-118.*
Declerck et al. Journal of Biological Chemistry, vol. 270, Issue 15, 1995, pp. 8397-8400.*
Rose et al. Nature 426, 74-78, 2003.*
Written Opinion mailed Jun. 9, 2021, issued in corresponding International Application No. PCT/US2021/015699, filed Jan. 29, 2021, 8 pages.
International Search Report mailed Jun. 9, 2021, issued in corresponding International Application No. PCT/US2021/015699, filed Jan. 29, 2021, 12 pages.
Queen, C., et al., "A Humanized Antibody That Binds to the Interleukin 2 Receptor," Proceeds of the National Academy of Sciences of the United States of America (PNAS) 86(24):10029-10033, Dec. 1989.

* cited by examiner

*Primary Examiner* — Oluwatosin A Ogunbiyi
(74) *Attorney, Agent, or Firm* — Christensen O'Connor Johnson Kindness PLLC

(57) ABSTRACT

In some aspects, the disclosure provides antibody-based reagents that specifically bind a tropomyosin receptor kinase B (TrkB) isoform that is associated with cancers. In some embodiments, the isoform is TrkB.T1. In some embodiments, the antibody or antibody derivative specifically binds a polypeptide comprising, consisting essentially of, or consisting of the sequence FVLFHKIPLDG (SEQ ID NO:1), or a sequence with at least 80% sequence identity thereto. In other aspects, the disclosure provides methods of producing the antibody or antibody derivative, related hybridomas, and methods of detecting and treating cancers incorporating use of the disclosed antibody reagents.

17 Claims, 27 Drawing Sheets

Specification includes a Sequence Listing.

Antibody Validation

1. Collect antisera after two rounds of boosting protocol

- ✧ 49  ✧ 298
- ✧ 50  ✧ 299
- ✧ 42r ✧ 300
- ✧ 43r ✧ 4976
- ✧ 51  ✧ 4977
- ✧ 52  ✧ 4979
- ✧ 53  ✧ 290
- ✧ 44r ✧ 291
- ✧ 45r ✧ 292
- ✧ 46  ✧ 13
- ✧ 47  ✧ 14
- ✧ 48  ✧ 92
- ✧ 94  ✧ 93
- ✧ 95

2. Test antisera

- • Western blot
- • Flow cytometry
- • IHC
  - – TrkB.T1$^{+/+}$ brain
  - – TrkB.T1$^{+/-}$ brain
  - – TrkB.T1$^{-/-}$ brain

3. Rank order top choices:

1. 13
2. 94
3. 4977
4. 14
5. 43r
6. 4976
7. 49
8. 42r
9. 92
10. 46

*A*

SEQ ID NO: 2

METDTILLWVLLLWVPGSTGQTVVTQESALTTSPGETVTLTCRSSTGA
VTTSNYANWVQEKPDHLFTGLIGGINNRAPGVPARFSGSLIGDKAVLTI
TGAQTEDEAIYFCALWYSNHWVFGGGTKLTVLGGGSGGGGSGGGGG
SQVQLQQSGPELARPWASVKISCQAFYTFSRGIHFDIRNTMYWIQWVK
QRPGQGLEWIGAIYPGNGDPTYSQNFKDKATLTADKSSNTAYMQLSSL
TSEDSAVYYCARYDYGGGFTYWGQGTLVTVSAGSAPSTCSKPTCPPP
ELLGGPSVFIFPPKDTLMISRTPEVTCVVVDVSQDDPEVQFTWY
INNEQVRTARPPLREQQFNSTIRVVSTLPITHQDWLRGKEFKCKV
HNKALPAPIEKTISKARGQPLEPKVYTMGPPREELSSRSVSLTCMI
NGFYPSDISVEWEKNGKAEDNYKTTPAVLDSDGSYFLYNKLSVPTS
EWQRGDVFTCSVMHEALHNHYTQKSISRSPGK

ANTIBODY-BASED COMPOSITIONS FOR TARGETING TROPOMYOSIN RECEPTOR KINASE B (TrkB) ISOFORMS

CROSS-REFERENCES TO RELATED APPLICATIONS

This application is a National Stage of International Application No. PCT/US2021/015699, filed Jan. 29, 2021, which claims the benefit of U.S. Provisional Application Nos. 62/967,978, filed Jan. 30, 2020 and 63/036,301, filed Jun. 8, 2020, the disclosures of which are hereby expressly incorporated herein by reference in their entireties.

STATEMENT REGARDING SEQUENCE LISTING

The sequence listing associated with this application is provided in text format in lieu of a paper copy and is hereby incorporated by reference into the specification. The name of the text file containing the sequence listing is 73262_Sequence_final_20210123.txt. The text file is 6 KB; was created on Jan. 23, 2021; and being submitted via EFS-Web with the filing of the specification.

BACKGROUND

The burden of cancers on society is immense, with millions of deaths and even more new cases occurring each year. Cancers are diseases characterized by dysregulated cell growth that ultimately lead to intrusion into and displacement of healthy tissue. This disruption of healthy tissue, including in areas distant from the point of initial transformation, results in the negative symptoms of the disease. Accordingly, early detection of cancer can be critical to maximizing the success of treatment and minimizing the morbidity caused by the disease.

Transformation into cancer cells includes the loss functional control of the cell cycle resulting in increased and uncontrolled replication as compared to the healthy cells from the same tissue. As part of their transformation, the cancer cells also typically begin to exhibit unique gene expression patterns and phenotypes compared to their healthy cell counterparts. These differences often include unique expression of proteins that can serve to differentiate the cancer cells from their healthy progenitor cells. Broadly, cancer cells are often categorized by the type of cell that is presumed to be origin of the cancer (e.g., carcinomas from epithelial cells, sarcomas from connective tissue cells, lymphomas and leukemias from hematopoietic cells, blastomas from immature precursor cells and embryonic tissues, etc.). Many specific lineages of cancers exhibit unique gene expression patterns, including expression of unique markers, that can be useful for detection of the particular cancer-type.

However, despite the advances in the art, there are few "pan-cancer" markers that can reliably signify a generalized cancer state, regardless of specific type. Thus, there remains a need for compositions and facile methods that reliably detect many cancer-types. This disclosure addresses these and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides an antibody or antibody-binding derivative thereof that binds to a polypeptide with a sequence with at least 80% or at least 90% identity to the sequence FVLFHKIPLDG (SEQ ID NO:1). In some embodiments, the polypeptide is in the C terminal domain of a human tropomyosin receptor kinase B (TrkB) isoform.

In some embodiments, the antibody is a monoclonal antibody. In some embodiments, the antibody is a chimeric antibody. In some embodiments, the chimeric antibody is humanized. In some embodiments, the antibody derivative comprises an antigen binding antibody fragment. In some embodiments, the antibody fragment is a Fab fragment, an F(ab)2 fragment, a VHH fragment, or a VNAR fragment. In some embodiments, the antibody derivative is a single chain antibody. In some embodiments, the single-chain antibody is a single chain variable fragment (scoff) or a single-chain Fab fragment (scFab). In some embodiments, the antibody or antigen binding derivative thereof comprises one or more of the complementarity determining regions (CDRs) included in a variable region corresponding to positions 21-273 of the sequence set forth in SEQ ID NO:2. In some embodiments, the antibody or antigen binding derivative thereof comprises a variable light chain region with an amino acid sequence with at least about 85% identity to a variable light chain region with a sequence of positions 21-129 of the sequence set forth in SEQ ID NO:2. In some embodiments, the antibody or antigen binding derivative thereof comprises a variable heavy chain region with an amino acid sequence with at least about 85% identity to a variable heavy chain region with a sequence of positions 146-273 of the sequence set forth in SEQ ID NO:2. In some embodiments, the antibody or antigen binding derivative thereof is detectably labeled.

In another aspect, the disclosure provides a method of producing an antibody that binds a polypeptide with at least 80% or at least 90% identity to the sequence FVLFHKIPLDG (SEQ ID NO:1). The method comprises:

immunizing an antibody producing animal with a construct comprising a peptide including a sequence with at least 80% or at least 90% identity to the sequence FVLFHKIPLDG (SEQ ID NO:1), wherein the animal has a genetic background that is null for a TrkB.T1 isoform, and isolating an antibody from the animal that binds to a polypeptide with at least 80% or at least 90% identity to the sequence FVLFHKIPLDG (SEQ ID NO:1).

In some embodiments, the C terminal domain comprises a polypeptide is a C-terminal domain of a human tropomyosin receptor kinase B (TrkB) isoform. In some embodiments, the construct comprises the peptide coupled to an immunogenic carrier. In some embodiments, the method further comprises isolating one or more splenocytes from the animal. In some embodiments, the method further comprises fusing a splenocyte obtained from the animal that produces an antibody that binds to the polypeptide with at least 80% or at least 90% identity to the sequence FVLFHKIPLDG (SEQ ID NO:1) with an immortal cell to produce a hybridoma.

In another aspect, the disclosure provides the hybridoma produced by the method described herein.

In another aspect, the disclosure provides a method of detecting the presence or elevated risk of a cancer in a subject, wherein the cancer is characterized by elevated levels of tropomyosin receptor kinase B (TrkB) isoform with a polypeptide with at least 80% or at least 90% identity to the sequence FVLFHKIPLDG (SEQ ID NO:1) at the C terminal end. The method comprises: contacting a biological sample obtained from the subject with the antibody or antibody derivative as described herein, and detecting binding of the antibody or antibody derivative to a component of the sample to determine a level of the TrkB isoform, wherein an elevated level of isoform TrkB isoform compared to a reference standard is indicative of the presence or risk of the cancer in the subject.

In some embodiments, the isoform is TrkB.T1. In some embodiments, the cancer is characterized by expression of nestin. In some embodiments, the cancer is a platelet-derived growth factor (PDGF)-driven cancer. In some embodiments, the cancer is characterized by reduced expression of phosphatase and tensin homolog (PTEN). In some embodiments, the cancer is a solid tumor. In some embodiments, the solid tumor is in soft tissue, kidney, liver, spleen, or central nervous system tissue. In some embodiments, the cancer is a non-solid tumor, e.g., a leukemia or lymphoma. In some embodiments, the cancer is selected from adreno-cortical carcinoma (ACC), bladder urothelial cancer (BLCA), breast invasive carcinoma (BRCA), cervical squamous cell carcinoma and endocervical adenocarcinoma (CESC), cholangiocarcinoma (CHOL), colon adenocarcinoma (COAD), colorectal adenocarcinoma (COAD/READ), lymphoid neoplasm diffuse B-cell lymphoma (DLBC), esophageal carcinoma (ESCA), head & neck squamous carcinoma (HNSC), kidney chromophobe (KICH), kidney renal clear cell carcinoma (KIRC), kidney renal papillary cell carcinoma (KIRP), acute myeloid leukemia (LAML), liver hepatocellular carcinoma (LIHC), lung adenocarcinoma (LUAD), lung squamous cell carcinoma (LUSC), mesothelioma (MES), ovarian serous cystadenocarcinoma (OV), pancreatic adenocarcinoma (PAAD), pheochromocytoma and paraganglioma (PCPG), prostate adenocarcinoma (PRAD), rectum adenocarcinoma (READ), sarcoma (SARC), skin cutaneous melanoma (SKCM), stomach adenocarcinoma (STAD), stomach and esophageal (STES), testicular germ cell tumor (TGCT), thyroid carcinoma (THCA), thymoma (THYM), uterine corpus endometrial carcinoma (UCEC), uterine carcinoma (UCS), uveal melanoma (UVM), and gliomas such as low grade glioma (LGG) and glioblastoma (GBM). In some embodiments, the cancer is a pediatric cancer selected from Wilms tumor (WT), rhabdoid tumor (RT), neuroblastoma (NBL), and clear cell sarcoma of the kidney (CCSK).

In some embodiments, the biological sample is a tissue sample. In some embodiments, the component of the sample is a cell. In some embodiments, the biological sample is a liquid sample. In some embodiments, the reference standard is a level of the TrkB isoform in an equivalent biological sample from one or more healthy subjects. In some embodiments, the biological sample is a tissue sample, and wherein the reference standard is a level of the TrkB isoform in an equivalent tissue sample from healthy tissue of the same subject. In some embodiments, the reference standard is a level of full length TrkB in the same biological sample or a similar biological sample as obtained from the subject. In some embodiments, the method further comprises treating the subject determined to have cancer. In some embodiments, the method is performed at multiple time points during and/or after treatment for cancer to monitor the efficacy of the treatment and/or recurrence of the cancer.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A graphically illustrates boxplots for transcript expression of TrkB.FL and TrkB.T1 from brain samples from The Genotype-Tissue Expression (GTEx) project and The Cancer Genome Atlas (TCGA) LGG and TCGA GBM demonstrate a predominance of TrkB.T1 in glioma samples compared to normal brain. FIG. 1B graphically illustrates Principal Component Analysis (PCA) plot of all brain samples from GTEx project and TCGA samples using gene expression from all genes from hg19. Samples are noted based on status of predominant NTRK2 transcript: "blue" for TrkB.T1 and "orange" for TrkB.FL. FIG. 1C illustrates TrkB.T1 and TrkB.FL transcript expression shows increased expression of TrkB.T1 compared to TrkB.FL across 50 human glioblastoma stem cell (GSC) lines (6 lines: BTSC349, BTSC349, h543, h516, h561, h676; 44 lines from Mack, S. C. et al. Chromatin landscapes reveal developmentally encoded transcriptional states that define human glioblastoma. *J. Exp. Med.* 216, 1071-1090 (2019), incorporated herein by reference) t-test, p=$1.9 \times 10^{-08}$.

FIG. 3A illustrates a receptor schematic of TrkB.FL and TrkB.T1 highlighting region of antibody specificity. FIG. 3B is a four-panel schematic summarizing antibody validating process. Mice used for TrkB.T1-specific antibody development included standard CD1, BALBC, A/J mice (mouse IDs shown in blue) and TrkB.T1−/− mice (mouse IDs shown in red). Prior to fusion, antisera from each mouse was tested for positive staining in immunohistochemistry on TrkB.T1+/+ wild-type mouse brain, TrkB.T1+/− mouse brain, and TrkB.T1−/− mouse brain and normal human brain. Clone selection protocol and representative image of positive western blots during antibody development using WES system. WES blots were confirmed with western blotting using Life Tech XCell SureLock® Mini-Cell electrophoresis system using wild-type mouse brain and TrkB.T1−/− brain. Western blots were performed in duplicate using technical replicates of each clone on biologically independent samples, and representative images were chosen, TrkB.T1 band at 95 kDa. Aperio 40× scale bars=25 μm. TrkB.T1 immunohistochemistry shows punctate vesicular staining in normal human (FIG. 3C) and mouse cortex (FIG. 3D) compared to intense diffuse staining in human (FIG. 3C) and mouse (FIG. 3D) glioma with lack of punctate vesicular pattern. Lack of staining in rodent negative control (no primary antibody) and TrkB.T1$^{-/-}$ cortex demonstrates antibody specificity for TrkB.T1 splice variant. (IDHmut—IDH mutant; 1p19q codel—1p 19 q co-deleted). Photomicrographs are at 40× and 600×. Immunohistochemistry was performed on independent biological samples of each tumor type, in replicates of 3-5.

FIG. 4A illustrates a Kaplan-Meier plot with Log-rank (Mantel-Cox) test showing symptom-free survival of PDGFB vs PDGFB+TrkB.T1 induced gliomas (median survival 34 days vs 109 days; *P<0.05). FIGURE B illustrates TrkB.T1 qRT-PCR results showing predominance in mouse tumorsphere cells lines. Cell lines were analyzed in triplicate; n=3 per cell type; error bars represent standard deviation. qRT-PCR bars for TrkB.T1 shown in teal, qRT-PCR bars TrkB.FL shown in orange. These results were consistent with western blot analyses (not shown).

FIG. 6B is an exemplary sequence of the fusion scFv-FC construct illustrated in FIG. 6A and which binds to the antigen with an amino acid sequence set forth in SEQ ID NO:1. The framework of rabbit IgG Fc domain is indicated in bold, whereas the IgK sequence is underlined.

FIG. 7A graphically illustrates results of a soft agar colony formation assay in 3T3 cells that shows significantly increased colonies with TrkB.T1 compared to control and TrkB.FL (p<0.0001; graph represents mean+SEM). Survival curves for Nestin/tv-a; Ink4a/Arf$^{-/-}$ mice injected with RCAS-shPTEN alone or RCAS-shPTEN+RCAS-TrkB.T1 (FIG. 7B) demonstrate decreases in survival due to tumor burden outside the central nervous system for mice injected with RCAS-TrkB.T1+RCAS-shPTEN vs. RCAS-shPTEN alone (median survival 131 days vs. 250 days, log rank hazard ratio 0.07243, 95% confidence interval 0.0.04768 to 0.11, p<0.0001) including soft tissue, kidney, liver, and spleen as shown in (FIG. 7C). FIG. 7D shows flow cytometry analysis of splenic tumor demonstrates a large B-cell lymphoma (CD45 bright/B220+; "blue" population). The histologic sections show a diffuse collection of large atypical cells with vesicular chromatin and high mitotic rate with a vague nodular pattern (20×). FIG. 7E shows flow cytometry analysis of splenic tumor demonstrates a myeloid leukemia (CD45+/GR1+; "pink" population) with extramedullary erythropoiesis (Ter119+/dim CD45; grey population). The histologic sections show focal collections of intermediate size cells with open chromatin and frequent mitosis, admixed with maturing erythroid cells (20×). FIG. 7F shows flow cytometry analysis of splenic tumor demonstrates an abnormal T-cell population (CD45 bright/CD3e+/CD4-/ CD8a-; "green" population) consistent with a T-cell lymphoma admixed with reactive B-cells (CD45 bright/B220 variable; "blue" population). The histologic sections show large atypical cells with a high mitotic rate admixed with scattered small reactive lymphocytes and eosinophils (20×).

DETAILED DESCRIPTION

Figure 1A:
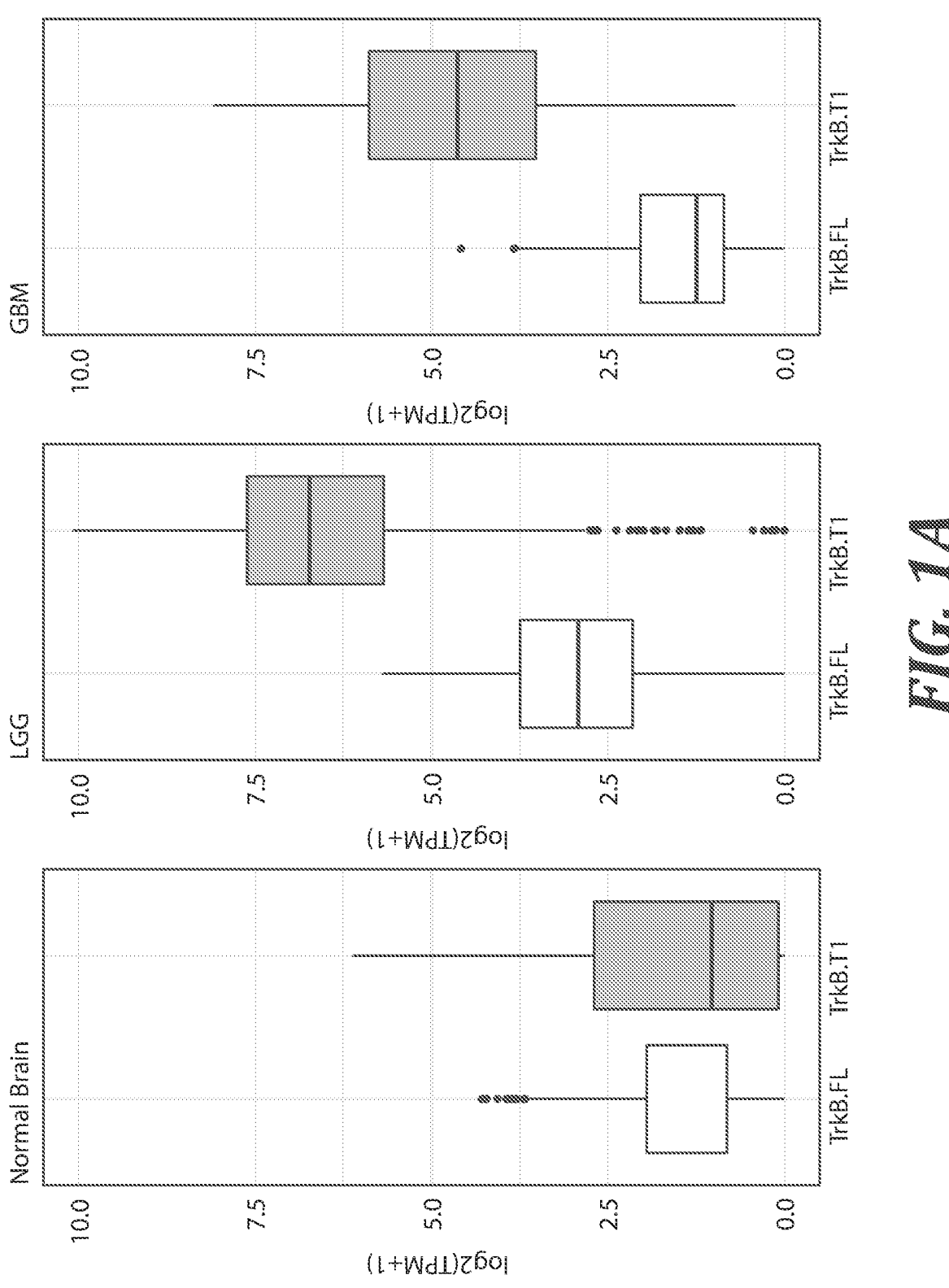
FIGS. 1A-1C illustrate that NTRK2 splice variant, TrkB.T1, is the predominant TrkB isoform in human glioma.

This disclosure is based on investigations demonstrating a novel role of isoforms of a neurotrophin receptor, tropomyosin receptor kinase B (TrkB; encoded by the NTRK2 gene), in cancers. As described in more detail below, the inventors first demonstrated the novel role for the TrkB splice variant, TrkB.T1, in human glioma via NTRK2 transcript analyses. While prior efforts to develop antibodies that specifically bound to the TrkB.T1 isoform failed due to lack of immunogenicity, the inventors employed an alternative approach and successfully developed a novel antibody that specifically bound to the TrkB.T1 isoform permitting for the first time immuno-detection of the isoform. TrkB.T1 was found to enhance PDGF-driven gliomas in vivo and to augment PDGF-induced Akt and STAT3 signaling in vitro. Next-generation sequencing broadly implicated TrkB.T1 in the PI3K/Akt and PI3K/ERBB2 signaling cascades in a ligand independent fashion. This study established NTRK2 as illustrating the importance of expanding upon whole gene and gene fusion analyses to explore splice variants in basic and translational oncology research.

Expanding on the initial results, the role of the TrkB.T1 splice variant was explored in multiple tumor types using The Cancer Genome Atlas (TCGA) and Therapeutically Applicable Research to Generate Effective Treatments (TARGET) data, as well as an RCAS/tv-a mouse model. The inventors demonstrated that TrkB.T1 is the predominant TrkB isoform in a wide range of adult and pediatric tumors and causes multiple tumor types in mice when combined with PTEN loss. Not only do these results demonstrate that the TrkB isoform has a causal role in the development of many types of cancers, thus providing a useful target for cancer therapy, but that it represents a powerful marker for the detection of cancer generally and can serve as the foundation for fast file strategies to detect and monitor cancer.

Antibody Compositions

As described below in more detail, previous efforts to produce selectively binding antibodies against TrkB.T1 isoforms have been routinely unsuccessful. The TrkB.T1 isoform deviates from the structure of full-length TrkB by having a truncated C-terminal end, which resides in the intracellular space when the translated is integrated in the plasma membrane. Additionally, due to an alternative splicing event, there is a unique ~11 amino acid sequence at the C-terminal end of the isoform that is not present in the full-length TrkB.FL protein. This 11 amino acid sequence, set forth herein as SEQ ID NO:1, is highly conserved among animals typically used for production of antibodies. Accordingly, without being bound to any particular theory, it is possible that this 11 amino acid sequence is not sufficiently immunogenic in the target antibody producing organisms because the B cells that would produce antibodies to it have been negatively selected by virtue of this peptide sequence being an endogenous antigen. Notwithstanding these limitations, the inventors were successful utilizing an alternative strategy (described in more detail below) that incorporated a series of peptide fusions and immunogenic boosting using genetically modified TrkB.T1$^{-/-}$ mice to produce selectively binding antibodies.

In accordance with the foregoing, in one aspect the disclosure provides an antibody or antigen-binding derivative thereof that specifically binds to an epitope in a C-terminal end domain of a tropomyosin receptor kinase B (TrkB) isoform. In some embodiments, the epitope is in a sequence comprising the last 11 continuous amino acids at the C-terminus TrkB.T1 isoform. In some embodiments, the last 11 continuous amino acids at the C-terminus TrkB.T1 isoform has the sequence FVLFHKIPLDG (set forth herein is SEQ ID NO:1), or has a sequence with at least 80% or 90% identity to SEQ ID NO:1. It will be understood that the disclosed antibody will specifically bind to any TrkB isoform that contains this C terminal sequence and the remainder of the isoform (i.e. N-terminal portions) need not be in perfect alignment with the known TrkB.T1 isoform sequence.

As used herein, the term "antibody" encompasses immunoglobulin molecules and antigen binding antibody derivatives and fragments thereof, derived from any antibody-producing mammal (e.g., mouse, rat, rabbit, and primate including human), that specifically bind to an antigen of interest (e.g., the C-terminal end of TrkB.T1 isoform, such as SEQ ID NO:1, or a sequence with at least 80% or 90% identity to SEQ ID NO:1). Exemplary antibodies include monoclonal antibodies, multi-specific antibodies (e.g., bispecific antibodies), chimeric antibodies (e.g., mouse-rabbit, mouse-human, mouse-primate, primate-human monoclonal antibodies), and humanized antibodies, as described in more detail below.

An antibody "derivative" encompasses fragments, modifications, fusions, or other antibody-related constructs that incorporate structure of at least part of an antibody molecule. An antigen-binding antibody derivative will typically contain at least a portion of the complementarity-determining regions (CDRs) of the original antibody sufficient to bind to the antigen of interest (e.g., the C-terminal end of TrkB.T1 isoform, such as SEQ ID NO:1, or a sequence with at least 80% or 90% identity to SEQ ID NO:1). An antibody "fragment" is a portion of a full-length antibody, preferably including the CDRs, antigen binding regions, and/or variable regions thereof necessary to permit binding to the antigen. Illustrative examples of antibody fragments and derivatives encompassed by the present disclosure include Fab, Fab', F(ab)$_2$, F(ab')$_2$ and Fv fragments, nanobodies (e.g., V$_H$H fragments and V$_{NAR}$ fragments), linear antibodies, single-chain antibody molecules, multi-specific antibodies formed from antibody fragments, and the like. Single-chain antibodies include single-chain variable fragments (scFv) and single-chain Fab fragments (scFab). A "single-chain Fv" or "scFv" antibody fragment, for example, comprises the V$_H$ and V$_L$ domains of an antibody, wherein these domains are present in a single polypeptide chain. The Fv polypeptide can further comprise a polypeptide linker between the V$_H$ and V$_L$ domains, which enables the scFv to form the desired structure for antigen (e.g., the C-terminal end of TrkB.T1 isoform, such as SEQ ID NO:1, or a sequence with at least 80% or 90% identity to SEQ ID NO:1) binding. Single-chain antibodies can also include diabodies, triabodies, and the like. Antibody fragments can be produced recombinantly, or through enzymatic digestion.

The disclosed antibody or antigen-binding derivative thereof does not have to be naturally occurring or naturally derived, but can be further modified to suit various uses, e.g., reduce the size of the domain or modify affinity for the antigen as necessary. For example, complementarity determining regions (CDRs) and potential entire variable regions can be derived from one source organism (e.g., mouse, human, etc.) and combined with other components, such as constant regions, of a different organism (e.g., human, mouse, rabbit, etc.) to produce a "chimeric molecule" that avoids stimulating immune responses in a subject. An exemplary chimeric antigen-binding antibody derivative is reflected in SEQ ID NO:2, which is the amino acid sequence of a chimeric construct containing the variable regions of the mouse D12 monoclonal antibody clone (described in more detail below) fused with rabbit IgG Fc sequence. It will be understood that constant regions of other species, such as from human, can be similarly incorporated into such a chimeric construct. A "humanized antibody" is a chimeric antibody that comprises a minimal sequence that conforms to specific CDRs derived from non-human immunoglobulin that is transplanted into a human antibody framework. Humanized antibodies are typically recombinant proteins in which only the antibody CDRs are of non-human origin.

The antibodies, or antibody fragments or derivatives of the disclosure can be produced using any technique commonly known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual* (Cold Spring Harbor Laboratory Press, 2nd ed. 1988); Hammerling et al., in: *Monoclonal Antibodies and T-Cell Hybridomas* 563-681 (Elsevier, N.Y., 1981), incorporated herein by reference in their entireties. The term "monoclonal antibody" refers to an antibody that is derived from a single clone, including any eukaryotic, prokaryotic, or phage clone, and not the method by which it is produced. Methods for producing and screening for specific antibodies using hybridoma technology are routine and well known in the art. Once a monoclonal antibody is identified, the encoding relevant binding domains can be cloned into an expression vector that also comprises nucleic acids encoding the other components of a derivative.

Antibody fragments that recognize specific epitopes can be generated by any technique known to those of skill in the art. For example, Fab and F(ab')₂ fragments of the invention can be produced by proteolytic cleavage of immunoglobulin molecules, using enzymes such as papain (to produce Fab fragments) or pepsin (to produce F(ab')₂ fragments). F(ab')₂ fragments contain the variable region, the light chain constant region and the CHI domain of the heavy chain. Further, the antibodies of the present invention can also be generated using various phage display methods known in the art.

As used herein, the term "specifically binds" refers to an association or union of a binding domain or a molecule containing the binding domain (e.g., an antibody or antigen-binding derivative or fragment thereof), to a target molecule (e.g., the C-terminal end of TrkB.T1 isoform, such as SEQ ID NO:1, or a sequence with at least 80% or 90% identity to SEQ ID NO:1) with an affinity or $K_a$ (i.e., an equilibrium association constant of a particular binding interaction with units of 1/M) equal to or greater than $10^5$ $M^{-1}$, while not significantly associating with any other domains of TrkB full length protein. Antibodies or antibody derivatives can be classified as "high affinity" or "low affinity". "High affinity" refers to antibodies or antibody derivatives with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" refers to those antibodies or antibody derivatives with a $K_a$ of up to $10^7$ $M^{-1}$, up to $10^6$ $M^{-1}$, up to $10^5$ $M^{-1}$. Alternatively, affinity can be defined as an equilibrium dissociation constant (Kd) of a particular binding interaction with units of M (e.g., $10^{-5}$ M to $10^{-13}$ M). In certain embodiments, an antibody or antibody derivative can have "enhanced affinity," which refers to a selected or engineered antibody or antibody derivative with stronger binding to a target antigen than a reference antibody or antibody derivative. For example, enhanced affinity may be due to a $K_a$ (equilibrium association constant) for the TrkB.T1 isoform that is higher than a reference antibody or antibody derivative, or due to a $K_d$ (dissociation constant)

for the TrkB.T1 isoform that is less than that of a reference antibody or antibody derivative, or due to an off-rate ($K_{off}$) for the TrkB.T1 isoform that is less than that of a reference antibody or antibody derivative. A variety of assays are known for identifying antibodies or antibody derivatives of the present disclosure that specifically bind TrkB isoforms, such as TrkB.T1 isoform, as well as determining binding domain affinities, such as Western blot, ELISA, and Biacore® analysis (see also, e.g., Scatchard et al., *Ann. N.Y. Acad. Sci.* 51:660, 1949; and U.S. Pat. Nos. 5,283,173, 5,468,614, or the equivalent).

In some embodiments, the antibody or antigen-binding derivative thereof comprises one or more of the light chain CDRs that are included in SEQ ID NO:2, for example in a light chain subdomain represented by residues 21-129 of SEQ ID NO:2. In some embodiments, the antibody or antigen-binding derivative thereof comprises one or more of the heavy chain CDRs that are included in SEQ ID NO:2, for example in a heavy chain subdomain represented by residues 146-273 of SEQ ID NO:2.

The antibody or antigen-binding derivative thereof can comprise a combination of the light and heavy chain CDRs that are present in SEQ ID NO:2, for example a light chain subdomain represented by residues 21-129 of SEQ ID NO:2 and/or a heavy chain subdomain represented by residues 146-273 of SEQ ID NO:2, as described above. For example, in some embodiments the antibody or antigen-binding derivative thereof comprises: at least CDRL1 and CDRH1, at least CDRL2 and CDRH2, or at least CDRL3 and CDRH3. In some embodiments, the antibody or antigen-binding derivative thereof comprises at least at least CDRL1, CDRL2, CDRH1, and CDRH2. In some embodiments, the antibody or antigen-binding derivative thereof comprises CDRL1, CDRL2, CDRL3, CDRH1, CDRH2, and CDRH3. Optionally, the CDRL1, CDRL2, and/or CDRL3 referred to above are the CDRs present in a light chain subdomain represented by residues 21-129 of SEQ ID NO:2, and/or the CDRH1, CDRH2, and/or CDRH3 referred to above are the CDRs present a heavy chain subdomain represented by residues 146-273 of SEQ ID NO:2, in any combination.

In certain embodiments, substitutions, insertions, or deletions may occur within one or more CDRs without substantially reducing the ability of the antibody to bind antigen (i.e., a TrkB.T1 isoform, such as SEQ ID NO:1 or a sequence with at least 80% or 90% identity to SEQ ID NO:1). For example, conservative alterations (e.g., conservative substitutions as provided herein) that do not substantially reduce binding affinity may be made in CDRs. In certain embodiments, each CDR provided above either is unaltered, or contains one, two, three or four amino acid substitutions.

In some embodiments, the CDRs and/or variable regions described above are included in the antibody or derivative thereof with framework region sequences having at least 90% identity, or at least 95% identity to a human immunoglobulin framework sequences. In some embodiments, each of framework region 1 (FR1), framework region 2 (FR2), framework region 3 (FR3), and framework region 4 (FR4) have at least 90% identity, or at least 95% identity to a corresponding human FR1, FR2, FR3, or FR4 sequence.

The CDRs in various combinations thereof described above are typically incorporated into a structure or scaffold permitting binding to the target antigen (e.g., the C-terminal end of TrkB.T1 isoform, such as SEQ ID NO:1, or a sequence with at least 80% or 90% identity to SEQ ID NO:1). In some embodiments, the antibody or antigen-binding derivative thereof comprises a variable light chain region with an amino acid sequence with at least about 85%, at least about 90%, at least about 95%, at least about 98%, at least about 99%, or 100% identity a variable light chain region present in SEQ ID NO:2, such as region with residues 21-129 of SEQ ID NO:2. In some embodiments, the antibody or antigen-binding derivative thereof comprises a variable heavy chain region with an amino acid sequence with at least about 85%, at least about 90%, at least about 95%, at least about 98%, at least about 99%, or 100% identity to a variable heavy chain region present in SEQ ID NO:2, such as region with residues 146-273 of SEQ ID NO:2. In some embodiments, the antibody or antigen-binding derivative thereof comprises both a variable light chain region with an amino acid sequence with at least about 85%, at least about 90%, at least about 95%, at least about 98%, at least about 99%, or 100% identity to a variable light chain region corresponding to residues 21-129 of SEQ ID NO:2 and a variable heavy chain region with an amino acid sequence with at least about 85%, at least about 90%, at least about 95%, at least about 98%, at least about 99%, or 100% identity to a variable heavy chain region corresponding to residues of 146-273 of SEQ ID NO:2.

In some embodiments the antibody or antigen-binding derivative thereof is detectably labeled. A label or detectable label, as used herein, refers to a moiety attached to an antibody or an analyte to render the reaction between the antibody and the analyte detectable, and the antibody so labeled is referred to as being "detectably labeled."

A label can produce a signal itself that is detectable by visual or instrumental means. Various labels include signal-producing substances, luminescent moieties, bioluminescent moieties, radioactive moieties, positron emitting metals, nonradioactive paramagnetic metal ions, and the like. A nonlimiting example of a luminescent moieties includes luminol; non-limiting examples of bioluminescent moieties include luciferase, luciferin, and aequorin; and nonlimiting examples of suitable radioactive moieties include a radio-active metal ion, e.g., alpha-emitters or other radioisotopes such as, for example, iodine (131I, 125I, 123I, 121I), carbon (14C), sulfur (35S), tritium (3H), indium (115mIn, 113mIn, 112In, U1In), and technetium (99Tc, 99mTc), thallium (201Ti), gallium (68Ga, /18t7\ 153r WO 2016/073853-44-PCT/US2015/059468 67Ga), palladium (103Pd), molybdenum (99Mo), xenon (133Xe), fluorine (10F), 13JSm, Lu, 159Gd, 149Pm, 140La, 175Yb, 166Ho, 90Y, 47Sc, 86R, 188Re, 142Pr, 105Rh, 97Ru, 68Ge, 57Co, 65Zn, 85Sr, 32P, 153Gd, 169Yb, 51Cr, 54Mn, 75Se, and tin (113Sn, 117Sn). The detectable moieties can be coupled or conjugated either directly to the antibody or antibody derivatives of the disclosure or indirectly, through an intermediate (such as, for example, a linker) using suitable techniques.

A label can also be a moiety that does not itself emit a signal but can be detected upon its activity with a substrate. For example, the label can be a suitable enzyme, such as horseradish peroxidase, alkaline phosphatase, β-galactosidase, glucose oxidase, or acetylcholinesterase, that can facilitate a detectable signal under specifically applied conditions using known substrates. Again, the detectable moieties can be coupled or conjugated either directly or indirectly to the antibody or antibody derivatives of the disclosure.

Additionally or alternatively, a functional payload can be tethered to the antibody or antibody derivative described above. The functional payload can be any payload capable of inducing a change in a target cell that expresses, at least transiently, a TrkB isoform (e.g., TrkB.T1). The change can be to a therapeutic effect if the cell is in vivo, in which case the payload can be characterized as a therapeutic payload. Exemplary, non-limiting functional payloads can comprise a nucleic acid, a protein or peptide, a lipid, a small molecule pharmaceutical, and/or a radioisotope. The antibody or antibody derivative can be conjugated to the functional payload according to any known technique. The conjugation can be covalent or ionic. Many linker and conjugation technologies are known and are encompassed by this disclosure.

Methods of Production

As described in more detail below, the inventors overcame substantial challenges faced in the art to produce antibodies that selectively bind the unique C-terminal domain of a TrkB isoform (e.g., TrkB.T1 resulting from an alternative displacing event).

Accordingly, in another aspect this disclosure provides a method of producing an antibody that binds a polypeptide with the sequence FVLFHKIPLDG (SEQ ID NO:1), or a sequence with at least 80% or 90% identity to SEQ ID NO:1. The method comprises: immunizing an antibody-producing animal with a construct comprising the peptide including the sequence FVLFHKIPLDG (SEQ ID NO:1), or a sequence with at least 80% or 90% identity to SEQ ID NO:1, wherein the animal has a genetic background that is null for a TrkB.T1 isoform, and isolating an antibody on antibody-producing cell from the animal, wherein the antibody binds to a polypeptide with the sequence FVLFHKIPLDG (SEQ ID NO:1), or a sequence with at least 80% or 90% identity to SEQ ID NO:1.

In some embodiments, the C-terminal domain comprises a polypeptide is a C-terminal domain of a human tropomyosin receptor kinase B (TrkB) isoform.

In some embodiments, the construct comprises the peptide coupled to an immunogenic carrier, such as KLH, BSA, and the like.

The method can further comprise conducting one or more rounds of immunological boosting. For example, additional rounds of immunization with the peptide can be performed. Furthermore, the initial or boosting administrations can be accompanied with adjuvants or other compositions to enhance the immune system and B cell stimulation in the context of the immunization.

In some embodiments, the method further comprises isolating one or more splenocytes from the animal. The splenocytes can be screened for production of antibodies that selectively bind to the peptide including the sequence FVLFHKIPLDG (SEQ ID NO:1), or a sequence with at least 80% or 90% identity to SEQ ID NO:1. In some embodiments, the method further comprises a splenocyte obtained from the animal that produces an antibody that binds to the polypeptide with the sequence FVLFHKIPLDG (SEQ ID NO:1), or a sequence with at least 80% or 90% identity to SEQ ID NO:1, with an immortal cell to produce a hybridoma. General procedures for producing antibodies are known and are disclosed in more detail in reference resources such as Harlow et al., *Antibodies: A Laboratory Manual* (Cold Spring Harbor Laboratory Press, 2nd ed. 1988); Hammerling et al., in: *Monoclonal Antibodies and T-Cell Hybridomas* 563-681 (Elsevier, N.Y., 1981), incorporated herein by reference in their entireties.

As indicated herein, the sequence FVLFHKIPLDG (SEQ ID NO:1) at the C-terminal end of the TrkB.T1 isoform is highly conserved among animal species. Accordingly, the model animal used to produce antibodies to this peptide sequence needs to be genetically modified to be null for any TrkB isoform that contains this C-terminal end (e.g., null for a TrkB.T1 isoform). The amino acid sequence FVLFH- KIPLDG (SEQ ID NO:1) at the C-terminal end of the TrkB.T1 isoform is encoded in exon 15 or 16, depending on the reference genome and/or nomenclature used to describe the encoding NTRK gene and its exons. Thus, the antibody-producing animal that is null for a TrkB.T1 isoform (TrkB.T1⁻/⁻) is missing at least the unique exon (exon 15 or 16, depending on the reference genome) that encodes FVLFHKIPLDG (SEQ ID NO:1), or in some embodiments an exon that encodes for a sequence with at least 80% or 90% identity to SEQ ID NO:1. For example, mice that are genetically engineered to be genetically null for the TrkB.T1 isoform, as described herein, are described in more detail in Dorsey, S. G. et al. In vivo restoration of physiological levels of truncated TrkB.T1 receptor rescues neuronal cell death in a trisomic mouse model. *Neuron* 51, 21-8 (2006), incorporated herein by reference in its entirety.

Method of Detection of Cancer

As demonstrated in more detail below, the novel antibodies or antibody derivatives of this disclosure are useful to detect the presence and amount of TrkB isoforms with the sequence FVLFHKIPLDG (SEQ ID NO:1), or a sequence with at least 80% or at least 90% identity thereto, at the C-terminal end. Furthermore, various studies revealed that elevated amounts of the detectable isoforms are indicative of cancer cells of many different types and varieties.

Accordingly, in another aspect the disclosure provides a method of detecting the presence or elevated risk of a cancer in a subject. In this aspect, the cancer is characterized by elevated levels of a tropomyosin receptor kinase B (TrkB) isoform with a polypeptide with the sequence FVLFH-KIPLDG (SEQ ID NO:1) at the C-terminal end. The method comprises:

contacting a biological sample obtained from the subject with the antibody or antibody derivative as disclosed herein, and detecting binding of the antibody or antibody derivative to a component of the sample to determine a level of the TrkB isoform, wherein an elevated level of the TrkB isoform compared to a reference standard is indicative of the presence or risk of the cancer in the subject.

The TrkB isoform in this aspect has a C-terminus comprising a peptide the sequence FVLFHKIPLDG (SEQ ID NO:1), or a sequence with at least 80% or at least 90% identity thereto. In some embodiments, the TrkB isoform is TrkB.T1.

As described in more detail below, elevated levels of the TrkB isoform were observed for a wide variety of cancer types and, thus provide for a pan-cancer marker. In some embodiments, the method can differentiate a specific type of cancer based on the amounts or ratio of the TrkB isoform present in the biological sample.

In some embodiments, the cancer can be further characterized by expression of nestin. In other embodiments, the cancer can be further characterized as a platelet-derived growth factor (PDGF)-driven cancer. In other embodiments, the cancer can be further characterized by having reduced expression of phosphatase and tensin homolog (PTEN). The reduced expression can be relative to a reference standard, such as derived from cells or tissues, e.g., equivalent cells or tissues, from an individual without cancer.

In some embodiments, the cancer is a solid tumor. Exemplary, nonlimiting solid tumors encompassed by the disclosure are solid tumors in soft tissue, kidney, liver, spleen, or central nervous system tissue.

Alternatively, the cancer can be a non-solid tumor, such as derived from hematopoietic cells. Exemplary, nonlimiting non-solid tumor cancers include leukemia or lymphoma.

As described in more detail below a pan-cancer transcription analysis of NTRK2 was conducted demonstrating marked increased expression for the TrkB.T1 isoform in a wide variety of cancers including adrenocortical carcinoma (ACC), bladder urothelial cancer (BLCA), breast invasive carcinoma (BRCA), cervical squamous cell carcinoma and endocervical adenocarcinoma (CESC), cholangiocarcinoma (CHOL), colon adenocarcinoma (COAD), colorectal adeno-carcinoma (COAD/READ), lymphoid neoplasm diffuse B-cell lymphoma (DLBC), esophageal carcinoma (ESCA), head & neck squamous carcinoma (HNSC), kidney chromophobe (KICH), kidney renal clear cell carcinoma (KIRC), kidney renal papillary cell carcinoma (KIRP), acute myeloid leukemia (LAML), liver hepatocellular carcinoma (LIHC), lung adenocarcinoma (LUAD), lung squamous cell carcinoma (LUSC), mesothelioma (MES), ovarian serous cystadenocarcinoma (OV), pancreatic adenocarcinoma (PAAD), pheochromocytoma and paraganglioma (PCPG), prostate adenocarcinoma (PRAD), rectum adenocarcinoma (READ), sarcoma (SARC), skin cutaneous melanoma (SKCM), stomach adenocarcinoma (STAD), stomach and esophageal (STES), testicular germ cell tumor (TGCT), thyroid carcinoma (THCA), thymoma (THYM), uterine corpus endometrial carcinoma (UCEC), uterine carcinoma (UCS), uveal melanoma (UVM), and gliomas such as low grade glioma (LGG) and glioblastoma (GBM), each of which is encompassed by the present disclosure. Furthermore, in some embodiments the cancer is a pediatric cancer selected from Wilms tumor (WT), rhabdoid tumor (RT), neuroblastoma (NBL), and clear cell sarcoma of the kidney (CCSK). Accordingly, the elevated expression of tropomyosin receptor kinase B (TrkB) isoform with a polypeptide with the sequence FVLFHKIPLDG (SEQ ID NO:1) at the C-terminal end is established as a general, pan-cancer marker as demonstrated by a wide variety of distinct cancer cell types and lineages, each of which is encompassed by the present disclosure. Furthermore, in view of the present disclosure, persons of ordinary skill in the art can routinely test additional cancer types to establish increased expression of the disclosed marker to provide a detectable signal as to the presence of that cancer.

Considering the wide applicability to such a broad array of cancer types, the disclosed method can be readily applied in a quick and fast facile approach to determining the general status of a subject for cancer. Upon determination of a cancer status, further tests can be employed to determine the specific type of cancer present in the subject.

The present method can incorporate a variety of biological samples. For example, a tissue sample (e.g. biopsy) can be obtained from the subject and contacted with the antibody or antibody derivative using standard histological approaches. In such embodiments, the cellular components within the biological sample can be observed for binding by the antibody or antibody derivative. In other embodiments, the biological sample is a liquid sample, such as blood, or blood products (e.g., plasma, serum, etc.), urine, saliva, mucus, sputum, cerebral spinal fluid, and the like. In such samples, the component to which the antibody or antibody derivative would bind to indicate the presence or level of the TrkB isoform can also be a cell or can be circulating TrkB isoform that is not associated with a cell.

This aspect encompasses any assay format that is appropriate for detection and/or quantification of the TrkB isoform in a sample. As indicated above, standard histological techniques can be applied to biopsy-type tissue samples. Alternatively, ELISA-type immune-assays can be applied using the disclosed antibody or antibody derivatives to detect circulating cells or TrkB isoform protein in a liquid sample.

As indicated, elevated levels of the TrkB isoform can be determined by comparison to a reference standard to indicate the presence or risk of cancer in the subject. A variety of approaches can be used for this comparison. For example, the reference standard can inform an increased ratio of the TrkB isoform relative to another protein, such as full length TrkB. In this context, the investigations described in more detail below demonstrated that the TrkB isoform is the dominant form of TrkB, i.e., is expressed at higher levels relative to the full-length TrkB itself, in the variety of testing cancer cells. The particular ratio of the TrkB isoform relative to the reference protein, such as full-length TrkB, that signals the presence of cancer can be readily determined for any particular cancer-type. In some embodiments, the ratio is greater than about 1:1 (isoform:full length), indicating that the TrkB isoform is the dominant form of TrkB expressed in the cells reflected by the sample. Accordingly, in some embodiments the reference standard is provided by a determination of the amount of full length TrkB. The amount of full length TrkB can be determined in the same biological sample or a similar biological sample from the same subject. Alternatively, the reference standard can inform the absolute level of the TrkB isoform. In these embodiments, the reference standard can be derived from a similar or equivalent biological sample (e.g., a biopsy from a same or similar tissue type, or a similar type of liquid sample) obtained from one or more healthy subjects, typically of the same species. In some embodiments, the reference standard can be a predetermined value based on prior determinations made from healthy subjects.

In some embodiments, once a determination is made as to the presence of cancer in the subject, and the type of cancer, the method further comprises treating the subject for the detected cancer according to accepted practice in the medical field for the determined cancer.

In other embodiments, the detection method can be performed at multiple time points, including before, during, and/or after medical intervention for the cancer. Performing the method at multiple time points permits monitoring the efficacy of the treatment and/or monitoring to establish remission or detect recurrence of cancer.

Additional Definitions

Unless specifically defined herein, all terms used herein have the same meaning as they would to one skilled in the art of the present invention. Practitioners are particularly directed to Sambrook J., et al. (eds.), *Molecular Cloning: A Laboratory Manual,* 3rd ed., Cold Spring Harbor Press, Plainsview, New York (2001); Ausubel, F. M., et al. (eds.), *Current Protocols in Molecular Biology*, John Wiley & Sons, New York (2010); and Coligan, J. E., et al. (eds.), *Current Protocols in Immunology*, John Wiley & Sons, New York (2010) Mirzaei, H. and Carrasco, M. (eds.), *Modern Proteomics—Sample Preparation, Analysis and Practical Applications in Advances in Experimental Medicine and Biology*, Springer International Publishing, 2016, and Comai, L, et al., (eds.), *Proteomic: Methods and Protocols in Methods in Molecular Biology*, Springer International Publishing, 2017, for definitions and terms of art.

For convenience, certain terms employed herein, in the specification, examples and appended claims are provided here. The definitions are provided to aid in describing particular embodiments and are not intended to limit the claimed invention, because the scope of the invention is limited only by the claims.

As used herein, the term "nucleic acid" refers to any polymer molecule that comprises multiple nucleotide subunits (i.e., a polynucleotide). Nucleic acids encompassed by the present disclosure can include deoxyribonucleotide polymer (DNA), ribonucleotide polymer (RNA), cDNA or a synthetic nucleic acid known in the art.

As used herein, the term "polypeptide" or "protein" refers to a polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

One of skill will recognize that individual substitutions, deletions or additions to a peptide, polypeptide, or protein sequence which alters, adds or deletes a single amino acid or a percentage of amino acids in the sequence is a "conservatively modified variant" where the alteration results in the substitution of an amino acid with a chemically similar amino acid. Conservative amino acid substitution tables providing functionally similar amino acids are well known to one of ordinary skill in the art. The following six groups are examples of amino acids that are considered to be conservative substitutions for one another:

(1) Alanine (A), Serine (S), Threonine (T),
(2) Aspartic acid (D), Glutamic acid (E),
(3) Asparagine (N), Glutamine (Q),
(4) Arginine (R), Lysine (K),
(5) Isoleucine (I), Leucine (L), Methionine (M), Valine (V), and
(6) Phenylalanine (F), Tyrosine (Y), Tryptophan (W).

Reference to sequence identity addresses the degree of similarity of two polymeric sequences, such as protein or nucleic acid sequences. Determination of sequence identity can be readily accomplished by persons of ordinary skill in the art using accepted algorithms and/or techniques. Sequence identity is typically determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. Various software driven algorithms are readily available, such as BLAST N or BLAST P to perform such comparisons.

The term "treating" and grammatical variants thereof refer to any indicia of success in the treatment or amelioration or prevention of a disease or condition (e.g., a cancer), including any objective or subjective parameter such as abatement, remission, diminishing of symptoms or making the disease condition more tolerable to the patient, slowing in the rate of degeneration or decline, or making the final point of degeneration less debilitating. The treatment or amelioration of symptoms can be based on objective or subjective parameters, including the results of an examination by a physician. Accordingly, the term "treating" includes the administration of compounds or agents to prevent or delay, to alleviate, or to arrest or inhibit development of the symptoms or conditions associated with disease or condition (e.g., a cancer). The term "therapeutic effect" refers to the reduction, elimination, or prevention of the disease or condition, symptoms of the disease or condition, or side effects of the disease or condition in the subject.

The terms "subject," "individual," and "patient" are used interchangeably herein to refer to a mammal being assessed for treatment and/or being treated. In certain embodiments, the mammal is a human. The terms "subject," "individual," and "patient" encompass, without limitation, individuals having cancer. While subjects may be human, the term also encompasses other mammals, particularly those mammals useful as laboratory models for human disease, e.g., mouse, rat, dog, non-human primate, and the like.

As used herein, characterization of a cell or population of cells being "positive" (or "+") for a particular marker refers to the cell or population of cells having the detectable presence of the marker. Conversely, use of the term "negative" (or "−") refers to the absence of a substantial presence in or on the surface of the cell.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application. The word "about" indicates a number within range of minor variation above or below the stated reference number. For example, "about" can refer to a number within a range of 10%, 9%, 8%, 7%, 6%, 5%, 4%, 3%, 2%, or 1% above or below the indicated reference number.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1

This Example describes an investigation demonstrating that a kinases deficient NTRK2 splice variant predominates in glioma and amplifies several oncogenic signaling pathways. This investigation was published as Pattwell, S. S., et al., *Nat Commun* 11, 2977 (2020), which is incorporated herein by reference in its entirety.

Independent scientific achievements have led to the discovery of aberrant splicing patterns in oncogenesis, while more recent advances have uncovered novel gene fusions involving neurotrophic tyrosine receptor kinases (NTRKs) in gliomas. The exploration of NTRK splice variants in normal and neoplastic brain provides an intersection of these two rapidly evolving fields. Tropomyosin receptor kinase B (TrkB), encoded NTRK2, is known for critical roles in neuronal survival, differentiation, molecular properties associated with memory, and exhibits intricate splicing patterns and post-translational modifications. Here, a role for a truncated NTRK2 splice variant, TrkB.T1, is demonstrated in human glioma. TrkB.T1 enhances PDGF-driven gliomas in vivo, augments PDGF-induced Akt and STAT3 signaling in vitro, while next generation sequencing broadly implicates TrkB.T1 in the PI3K signaling cascades in a ligand-independent fashion. These TrkB.T1 findings highlight the importance of expanding upon whole gene and gene fusion analyses to include splice variants in basic and translational neuro-oncology research. More specifically, the TrkB splice variant, TrkB.T1, is a novel and powerful marker and target for glioma detection and therapy.

Introduction

As decades of research have uncovered key drivers in oncogenic signaling through the discovery of tumor suppressors, oncogenes, histone modifications, DNA methylation, and environmental factors, the possibility remains that such factors may contribute to splicing events at the core of oncogenesis. While recent work independently highlights the evolving importance of aberrant splicing in cancer, simultaneous discoveries have implicated novel NTRK2 fusions in various glioma subtypes, yet little is known about endogenous NTRK2 splicing in human brain or its potential role in brain tumor biology. Prior studies have implicated TrkB in the survival of brain tumor initiating cells in the absence of growth factors epidermal growth factor (EGF) and fibroblast growth factor (FGF), while more recent work has implicated TrkB and its ligand, brain-derived neurotrophic factor (BDNF), in the crosstalk between glioma stem cells and their differentiated glioblastoma cell progeny, suggesting that this neurotrophin receptor exhibits complex interactions within the brain tumor environment that extend beyond the canonical TrkB-BDNF signaling events characterized in normal neurodevelopment. Malignant tumors of the central nervous system and brain tumors, specifically, result in the highest years of potential life lost compared with other cancer types, while glioblastoma multiforme (GBM), in particular, remains the most common malignant primary brain tumor with a mere 2-4% 5-year survival rate. Accordingly, the complex role of TrkB in GBM and lower grade gliomas (LGGs) was further investigated in effort to learn more about the neurotrophin receptor splicing contributions to these devastating tumors.

The neurotrophin receptor TrkB, encoded by the NTRK2 gene (hg19: chr9:87,283,466-87,638,505) has well-known roles in neuronal survival, proliferation, differentiation, apoptosis, and exerts diverse effects on cellular and neural outcomes. In addition to the full-length receptor tyrosine kinase, TrkB.FL, several lesser known, alternatively spliced variants, including the truncated isoform, TrkB.T1, have been shown to exist. Once thought dominant-negative due the absence of a kinase domain, TrkB.T1 shares the same extracellular and transmembrane domains, as well as the first 12 intracellular amino acids, as other variants yet contains a unique C-terminal sequence of 11 amino acids that is conserved across species from rodents to humans. In vitro, TrkB.T1 has been shown to alter $Ca^{2+}$ signaling, regulate neuronal complexity, influence astrocytic morphology via Rho GTPases, modify filopodia outgrowth, and contribute to signal transduction and proliferation, raising the possibility that this formerly considered dominant-negative receptor variant has unique and important roles in both normal and abnormal brain development.

Here, it is demonstrated that the TrkB.T1 splice variant is the predominant TrkB isoform expressed across a range of human gliomas. By generating an antibody specific for this splice variant, it is shown that TrkB.T1 receptor localization differs between normal, healthy brain regions and gliomas, in both rodents and humans. In vivo experiments using RCAS-tv/a technology demonstrate that TrkB.T1 enhances PDGFB-driven tumors in mice, while in vitro experiments show that TrkB.T1 enhances the perdurance of PI3K and STAT3 signaling pathways including pAkt and pS6rp. Together, these results demonstrate a previously unidentified role for the NTRK2 splice variant TrkB.T1 in gliomas and highlight the importance of exploring alternative splicing of TRKs in basic and translational research.

Results

Distinct Gene Expression in Normal Human Brain Vs. Glioma

To first investigate the overall genetic variance in human brain tumors compared with normal brain, publicly available gene expression data was queried from The Genotype-Tissue Expression (GTEx) Project on 1216 normal samples across 13 GTEx-defined brain regions [Amygdala (72); Anterior cingulate cortex (BA24) (82); Caudate (basal ganglia) (113); Cerebellar hemisphere (101); Cerebellum (121); Cortex (109); Frontal cortex (BA9) (104); Hippocampus (92); Hypothalamus (90); Nucleus accumbens (basal ganglia) (109); Putamen (basal ganglia) (93); Spinal cord (cervical c-1) (68); and Substantia nigra (62)], 170 GBM samples [GBM (CIMP) (5); GBM (nonCIMP) (59); GBM CIMP status not-available (106)] and 532 LGG samples [Low grade glioma (532); Low grade glioma (CIMP) (437); Low grade glioma (nonCIMP) (95)] from The Cancer Genome Atlas (TCGA). Principal component analysis (PCA) of gene expression data from 20,214 genes across 1216 normal brain GTEx samples revealed three genetically distinct clusters within normal brain samples consisting of multiple supratentorial regions, cerebellum, and spinal cord (not shown). For a more anatomically accurate comparison of genetic variance from normal brain to brain tumors, cerebellum and spinal cord were removed, supratentorial regions were pooled, and these 926 samples are referred to as Normal Brain. Two clear clusters were formed, TCGA-GBM and TCGA-LGG samples fall into one cluster while the supratentorial regions from GTEx maintain the one pooled normal brain cluster from. PCA of the 20,214 genes Normal Brain, LGG and GBM samples, revealed distinct differences in overall gene expression between normal brain and cancer samples (not shown). Similar to previous studies showing distinct clustering based on methylation phenotype, PCA of gene expression data from GBM and LGG samples also yielded distinct clusters of gliomas based on status of CpG island methylator phenotype (CIMP) and non-CIMP (not shown). To rule out systematic differences between GTEx and TCGA data, median whole gene expression in Normal Brain, LGG and GBM samples were compared at a per-gene level, and it was determined that 10,910 genes were overrepresented in TCGA (7769 in GBM; 3141 in LGG) and 9304 genes had higher expression value in Normal Brain samples (not shown). After also confirming that NTRK2 RNASeq expression is reliable across bioinformatic pipelines and does not fall into the less than 12% of genes that are discordantly quantified across commonly used pipelines across, NTRK2 expression across normal brain regions and brain tumors were compared. Given the abundance of literature highlighting the role of NTRK2 in cancer, similar whole gene NTRK2 expression was found across Normal Brain, LGG and GBM samples, suggesting that differences in expression of particular splice variants may underlie potential oncogenic effects driven by NTRK2 (Table 1).

TABLE 1 log2 (TPM) values for NTRK2 Whole
Gene Expression, TrkB.FL Transcript
Expression, and TrkB.T1 Transcript Expression

| | GBM | LGG | Normal Brain |
|---|---|---|---|
| Whole Gene NTRK2 | | | |
| Minimum | 0 | 0.7075 | 1.268 |
| 1st Quartile | 2.2741 | 5.957 | 5.378 |
| Median | 3.6168 | 7.0254 | 6.122 |
| Mean | 3.6745 | 6.7596 | 5.964 |
| 3rd Quartile | 5.2447 | 7.9051 | 6.655 |
| Maximum | 8.1451 | 10.5174 | 8.447 |
| TrkB.FL Transcript | | | |
| Minimum | 0 | 0 | 0 |
| 1st Quartile | 0.8538 | 2.151 | 0.8105 |
| Median | 1.2465 | 2.919 | 1.3802 |
| Mean | 1.4758 | 2.906 | 1.4481 |
| 3rd Quartile | 2.0373 | 3.741 | 1.9504 |
| Maximum | 4.5814 | 5.701 | 4.2866 |
| TrkB.T1 Transcript | | | |
| Minimum | 0.6939 | 0 | 0 |
| 1st Quartile | 3.5196 | 5.679 | 0.08282 |
| Median | 4.6364 | 6.727 | 1.0323 |
| Mean | 4.7139 | 6.426 | 1.48244 |

TABLE 1-continued

| | log2 (TPM) values for NTRK2 Whole Gene Expression, TrkB.FL Transcript Expression, and TrkB.T1 Transcript Expression | | |
| --- | --- | --- | --- |
| | GBM | LGG | Normal Brain |
| 3$^{rd}$ Quartile | 5.8816 | 7.611 | 2.69518 |
| Maximum | 8.0924 | 10.084 | 6.11901 |

TrkB.T1 Expression is Increased in Human Gliomas

Figure 1B:
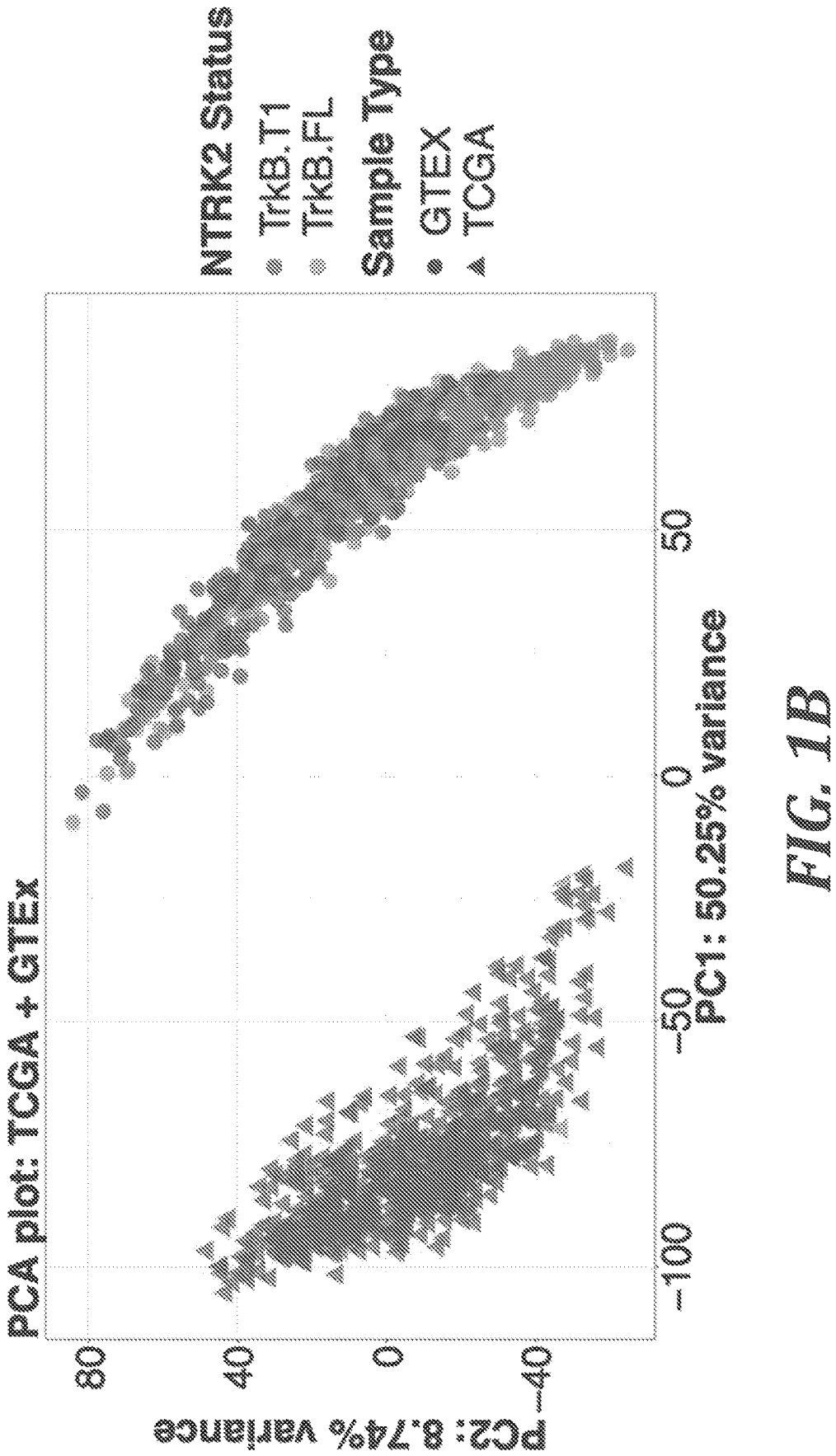
Figure 1C:
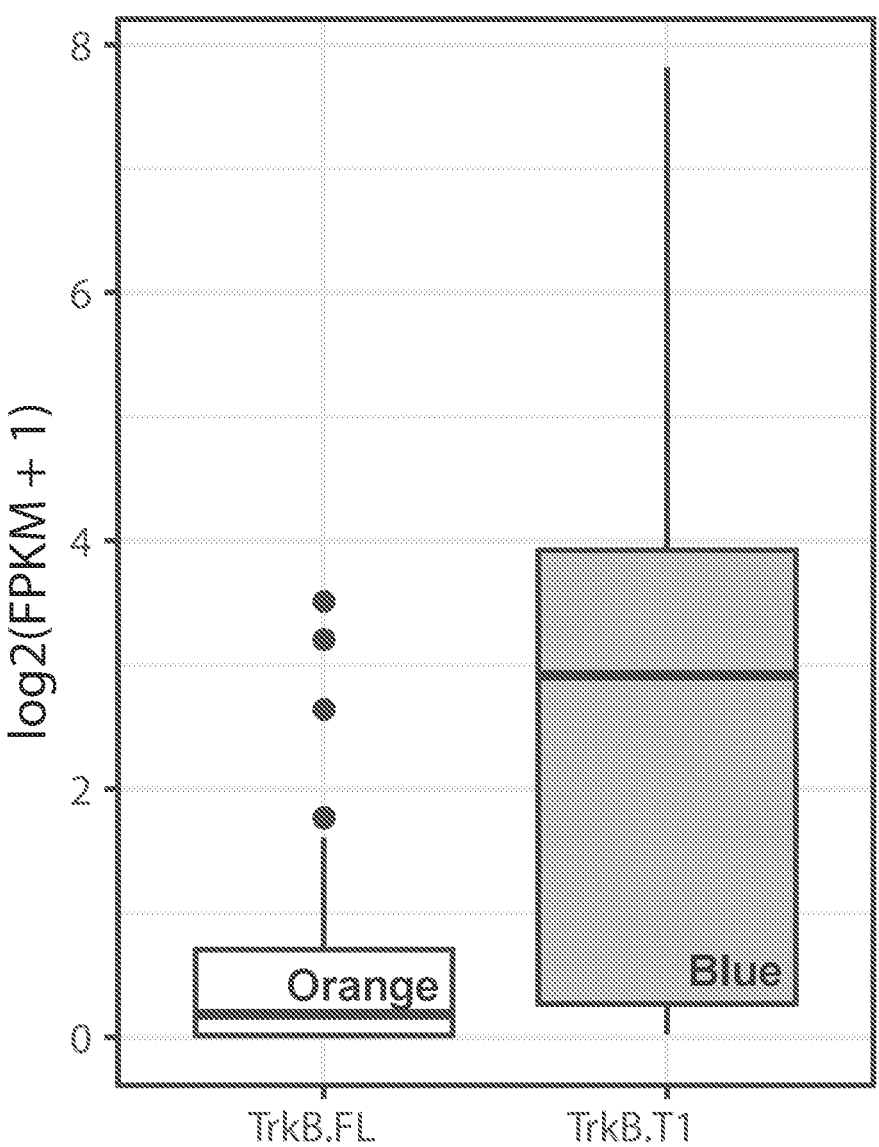
Figure 2:
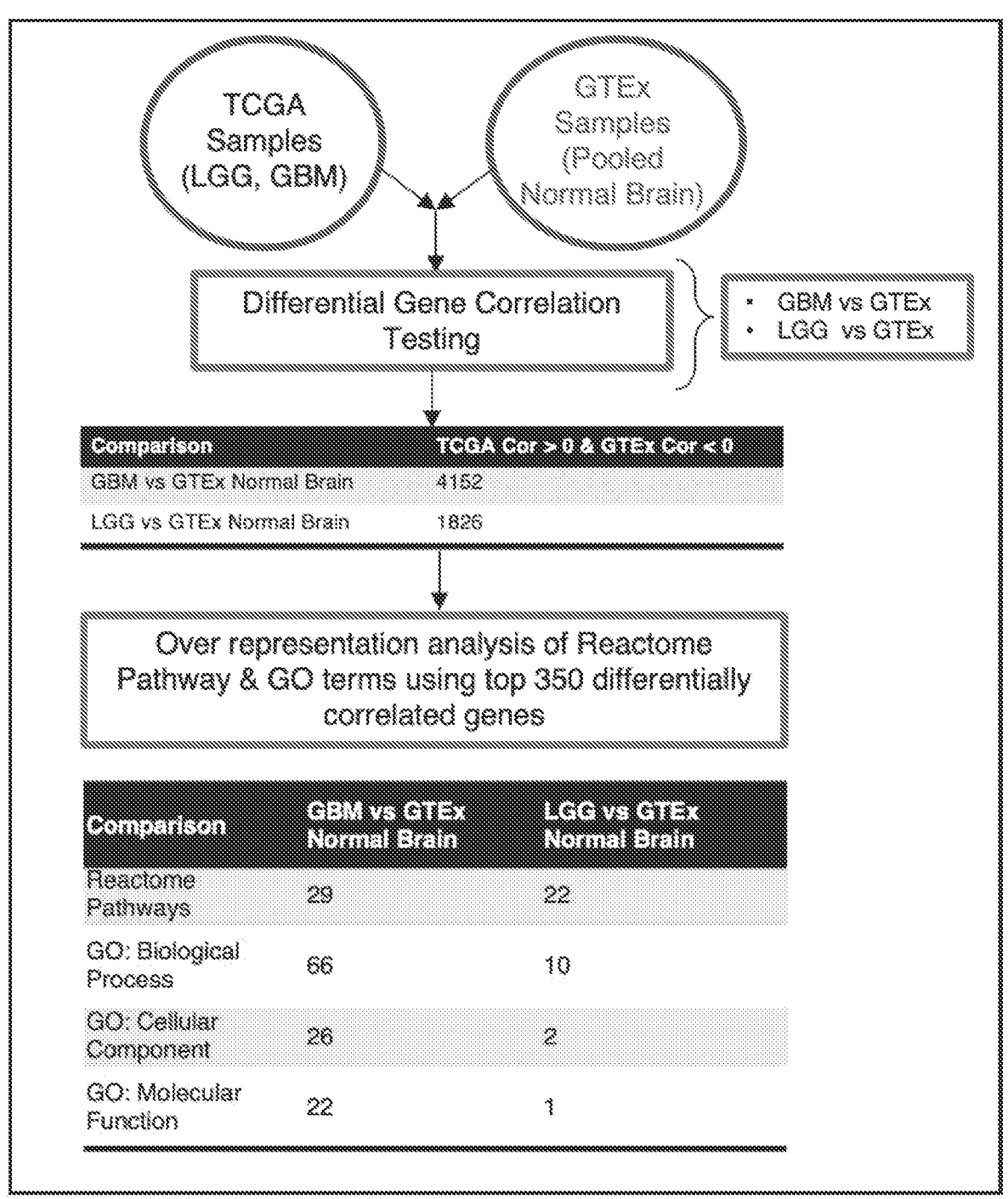
FIG. 2 is a schematic of Differential Gene Correlation Analysis (DGCA) for the top 350 genes significantly positively correlated with NTRK2 in LGG or GBM. GO terms for biological processes in top 350 differentially expressed genes in GBM compared to normal brain and GO terms for the top 350 differentially expressed genes in the cellular component in GBM compared to normal brain revealed a predominance of genes implicated in morphogenesis and proliferation, as well endocytic compartments and vesicular transport. A set of gene ontology enrichment terms was generated for the genesets within the reactome pathways in top 350 differentially expressed genes in LGG compared to normal brain.

Given TrkB's diverse roles in neurodevelopment, the expression of the two most studied NTRK2 splice variants, the full-length receptor tyrosine kinase (TrkB.FL), and kinase-deficient truncated isoform (TrkB.T1) were compared. Using publicly available transcript data from GTEx (available as RPKM data) and TCGA (available as RSEM counts from the legacy archive), all transcript data was converted to Transcripts Per Million (TPM) to allow for isoform comparisons across TCGA and GTEx. Contrary to existing hypotheses surrounding the full-length kinase, TrkB.FL, as the sole suspected NTRK2 contribution to oncogenesis, TrkB.FL levels remain relatively consistent across pooled normal supratentorial regions, LGG and GBM (FIG. 1A, Table 1). Moreover, in contrast to a suspected role of the TrkB kinase in gliomas, it was found that high transcript expression of TrkB.FL is associated with better prognosis for both GBM and LGG, not worse prognosis (not shown). Briefly, survival curve for all TCGA low grade glioma (LGG) and glioblastoma multiforme (GBM) samples combined were compared to survival curve for all combined TCGA samples divided by TrkB.FL status. This revealed that higher TrkB.FL expression does not correlate with worse survival but correlates with longer survival (above median=TrkB.FL high; below median=TrkB.FL low; 2907 days vs 758 days (log rank hazard ratio 0.2827, 95% confidence interval 0.2195-0.3641, p<0.0001)). When stratified by tumor type, there was a trend for TrkB.FL status to correlate with longer survival in GBM (448 days vs 408 days) but this is not statistically significant. There is a significant effect of TrkB.FL status on survival in LGG where high TrkB.FL corresponds with longer survival (e, f) 2907 days vs 1933 days (log rank hazard ratio 0.6281, 95% confidence interval 0.4411-0.8945, p<0.005). By contrast, transcript expression levels of kinase-deficient TrkB.T1 were significantly increased in both CIMP and non-CIMP gliomas (LGG and GBM) compared with all normal brain regions (FIG. 1A, Table 1). Compared with TrkB.FL, TrkB.T1 emerged as the predominant isoform expressed in nearly all human gliomas in TCGA (FIG. 2B). Further analysis across all NTRK2 isoforms confirmed that transcripts with the unique TrkB.T1-specific 11-amino acid C-terminus predominate not only over transcripts containing the TrkB kinase, but also when compared with all other NTRK transcripts (including NTRK1, NTRK2, NTRK3) (not shown). Analysis of 50 human glioblastoma stem cell (GSC) lines isolated from primary tumors show that this TrkB.T1 variant predominates over all other NTRK isoforms, further highlighting its potential role in brain tumor biology (FIG. 1C). Briefly, TrkB.T1 was observed to be the predominant NTRK2 isoform expressed in 6 in house GSCs lines (BTSC349, BTSC349, h543, h516, h561 and h676) and in 44 additional GSC lines derived from primary tumors. TrkB.FL expression remained low across all GSC subtypes while TrkB.T1 expression was increased compared to other NTRK2 variants across GSC subtypes (50 total GSC lines). TrkB.T1 Distribution is Altered in Neoplastic Brain As TrkB.T1 is the predominantly expressed isoform compared with TrkB.FL in LGG and GBM, differential gene correlation analysis (DGCA) was used to find differentially correlated genes whose expression was positively correlated with NTRK2 in LGG or GBM and anti-correlated with NTRK2 in normal brain. Of these significantly correlated genes, the top 350 genes for each tumor type were subjected to gene ontology (GO) analysis to determine which, if any, classes of genes were enriched in NTRK2 glioma pairings (FIG. 2). GO terms were generated for the top 350 differentially expressed genes in GBM compared to normal brain and GO terms for the top 350 differentially expressed genes in the cellular component in GBM compared to normal brain. The GO analysis for both biological processes and cellular component revealed a predominance of genes implicated in morphogenesis and proliferation, as well those implicated in endocytic and vesicular transport (not shown), suggesting that the subcellular location of TrkB.T1 may be critical to its function and could be different between tumor and normal brain. Additionally, because previous work has alluded to more efficient recycling of TrkB.T1 receptors back to the plasma membrane in PC12 cells and neurons, the next task was to identify the distribution of TrkB.T1 in normal human brain and human gliomas based on these DGCA results implicating endocytic and vesicular transport genes.

Figure 4A:
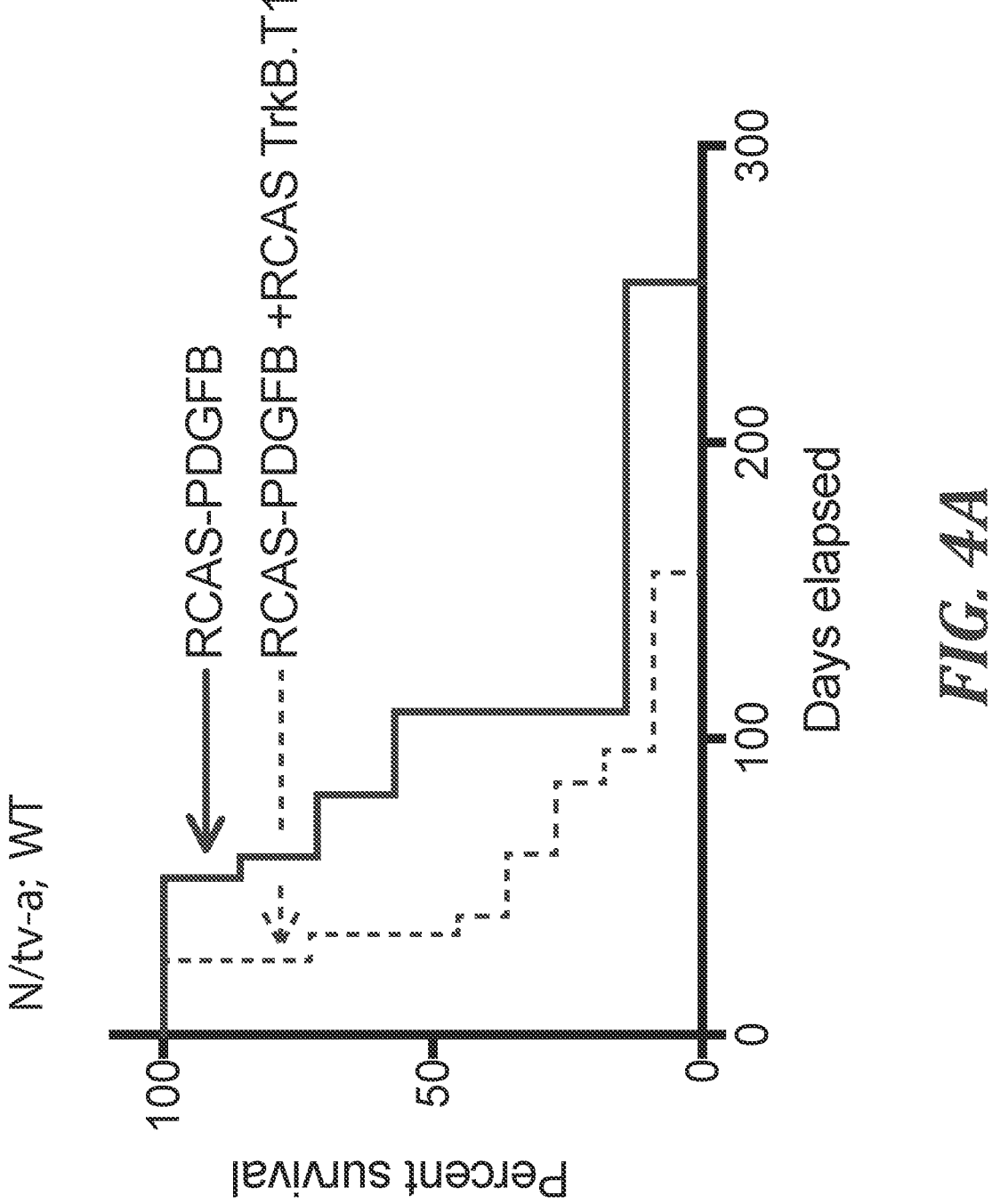
FIGS. 4A and 4B illustrate TrkB.T1 enhances PDGF signaling in vivo and in vitro.
Figure 4B:
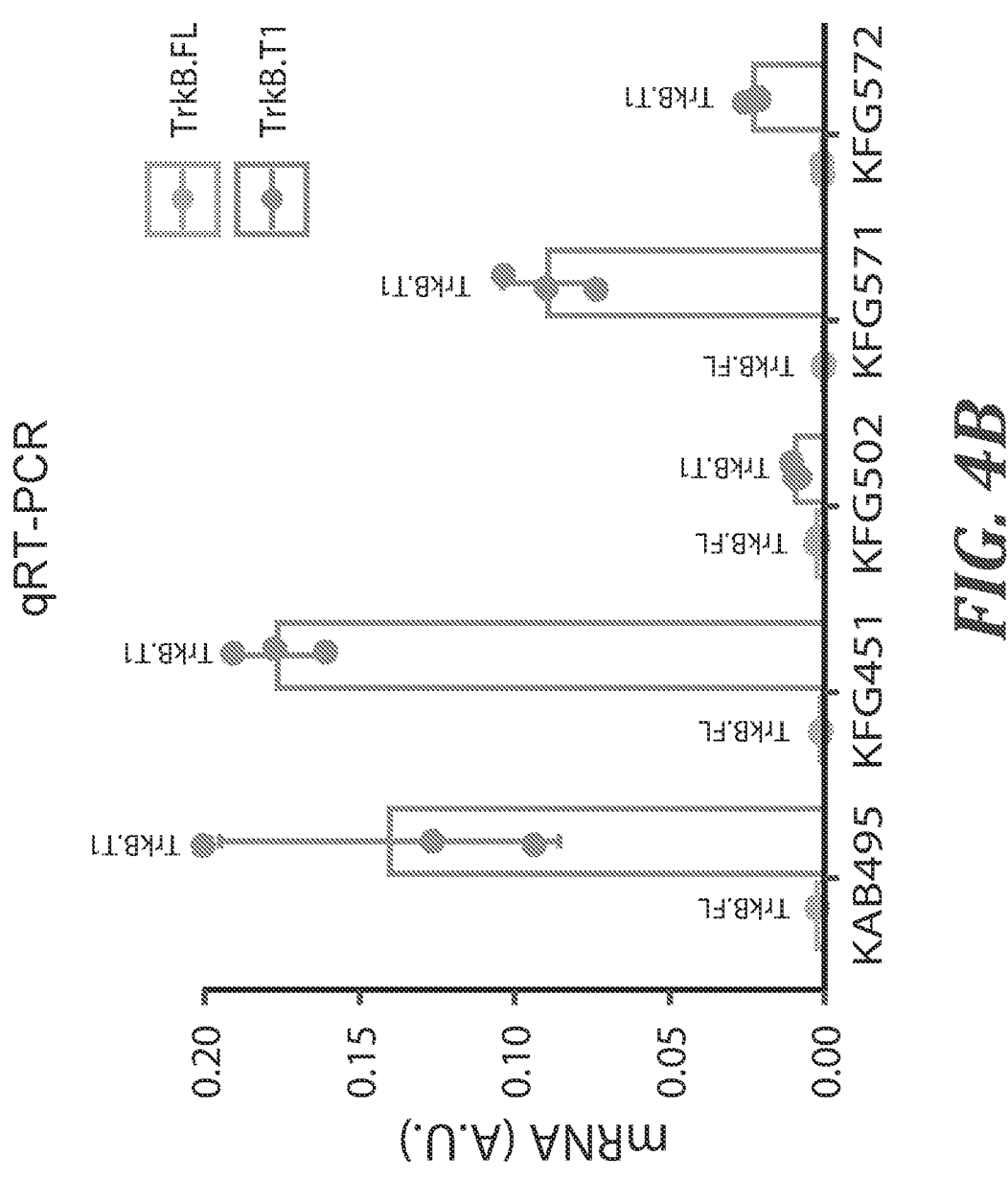

Basic scientific and clinical investigation surrounding TrkB's role in neurodevelopment and oncology has often been hindered due to its complex splicing patterns combined with frequent inability of available antibodies to distinguish between TrkB isoforms. While early immunohistochemical analyses of neural tumors using pan-Trk antibodies confirmed presence of at least one neurotrophin receptor, little insight could be gained as to which TRK (or TRKs) were present or if receptor distribution differed between neural and non-neural tissue. Further, TrkB-specific antibodies do not easily discriminate between the full and truncated variant gene products as the majority are generated against either the entire extracellular domain or extracellular subdomains—regions conserved between full-length and various truncated isoforms. This lack of reagent specificity does not prohibit certain assays but has made visualization of endogenous TrkB splice variants difficult and often requires the use tagged constructs or in vitro systems. To determine endogenous localization of TrkB.T1 in human brain, a monoclonal antibody to the unique intracellular region of TrkB.T1's 11-conserved amino acids (FVLFHKIPLDG; SEQ ID NO:1) was designed, developed, and validated through a series of peptide fusions and immunogenic boosting of TrkB.T1$^{-/-}$ mice as strong cross-species conservation of this receptor has previously made standard rabbit or mouse colonies unsuitable for successful antibody production (FIGS. 4A and 4B).

Normal brain tissue from rapid autopsies (n=5) was procured and subjected to TrkB.T1 immunohistochemistry (IHC) with this TrkB.T1-specific antibody. Each control case contained both supratentorial and infratentorial brain regions, including cerebral cortex, cerebellum, hippocampus, subiculum, entorhinal cortex, and thalamus (see FIG. 3C for exemplary images). TrkB.T1 IHC on normal human brain reveals a distinct punctate intracellular localization and distribution of TrkB.T1 throughout the frontal cortex, hippocampus, and cerebellum. Several normal brain regions exhibit abundant neurons, and glial cells, with strongly intense, cytoplasmic TrkB.T1 immunohistochemical staining in a predominantly vesicular pattern (not shown).

Figure 3A:
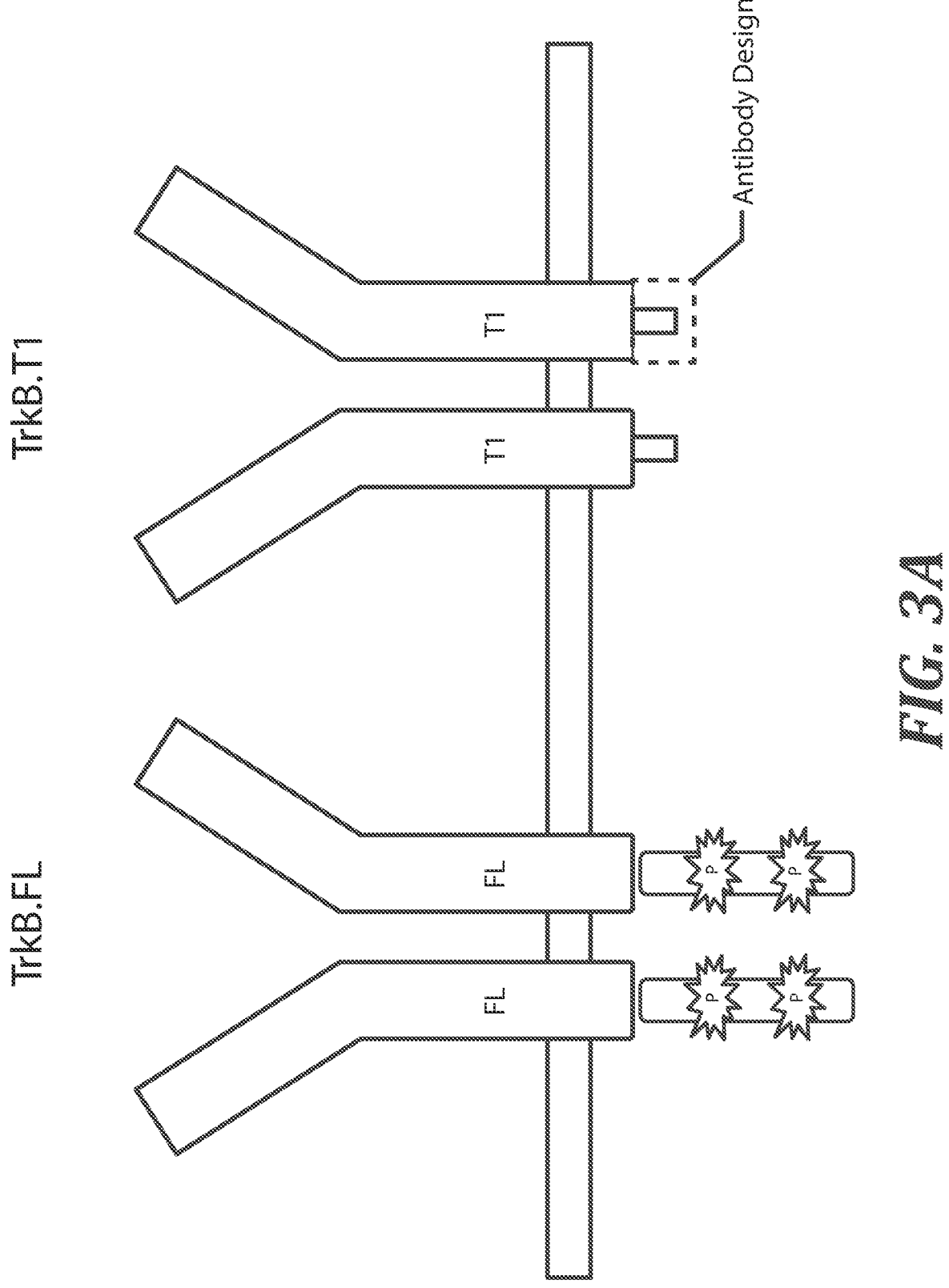
FIGS. 3A-3D illustrate the development of an antibody specific for the TrkB.T1 variant and exemplary results of use thereof in human and rodent TrkB.T1 immunostaining in normal brain and glioma.
Figure 3B:
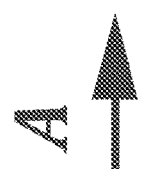
Figure 3B:
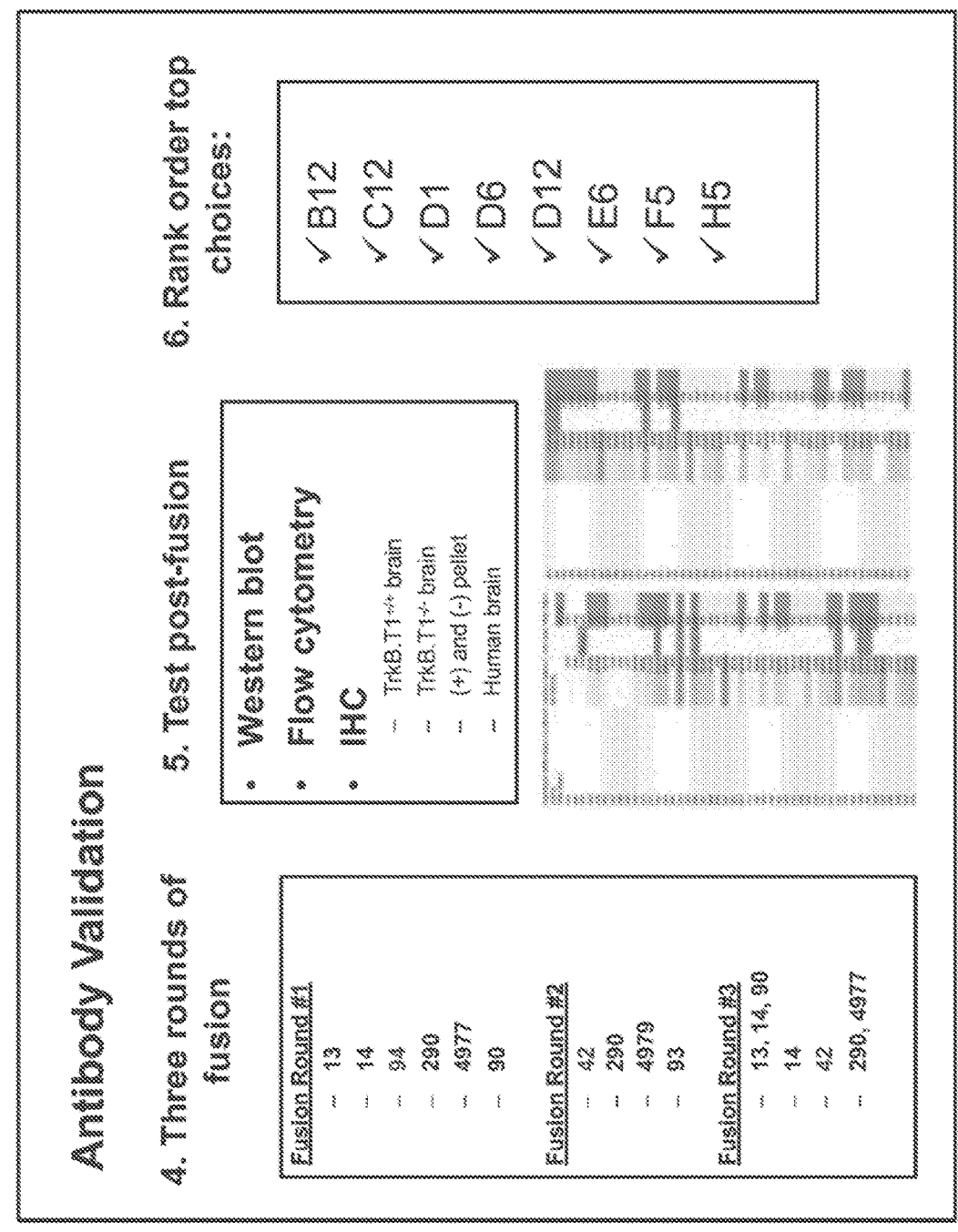
Figure 3B:
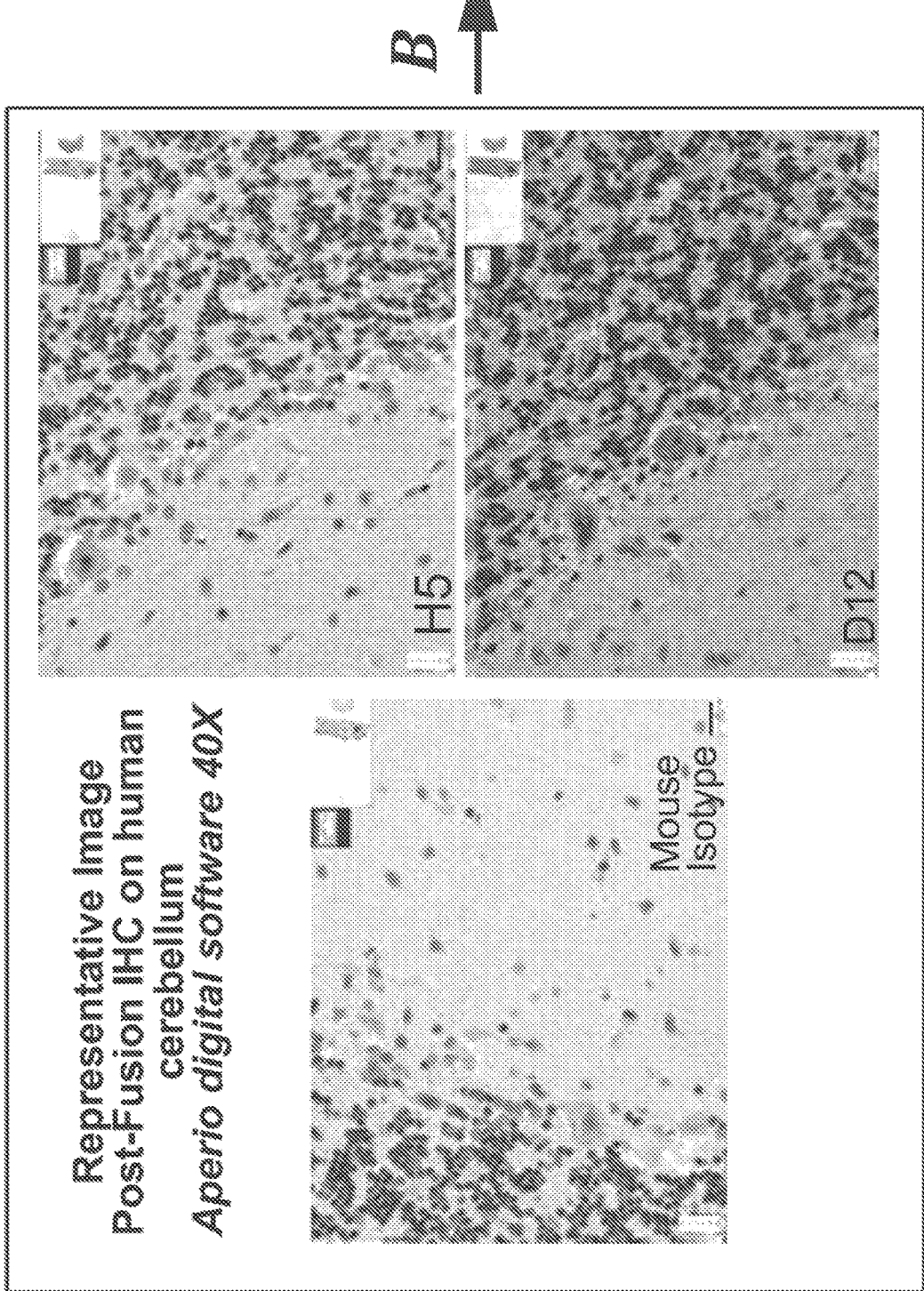
Figure 3B:
Figure 3C:
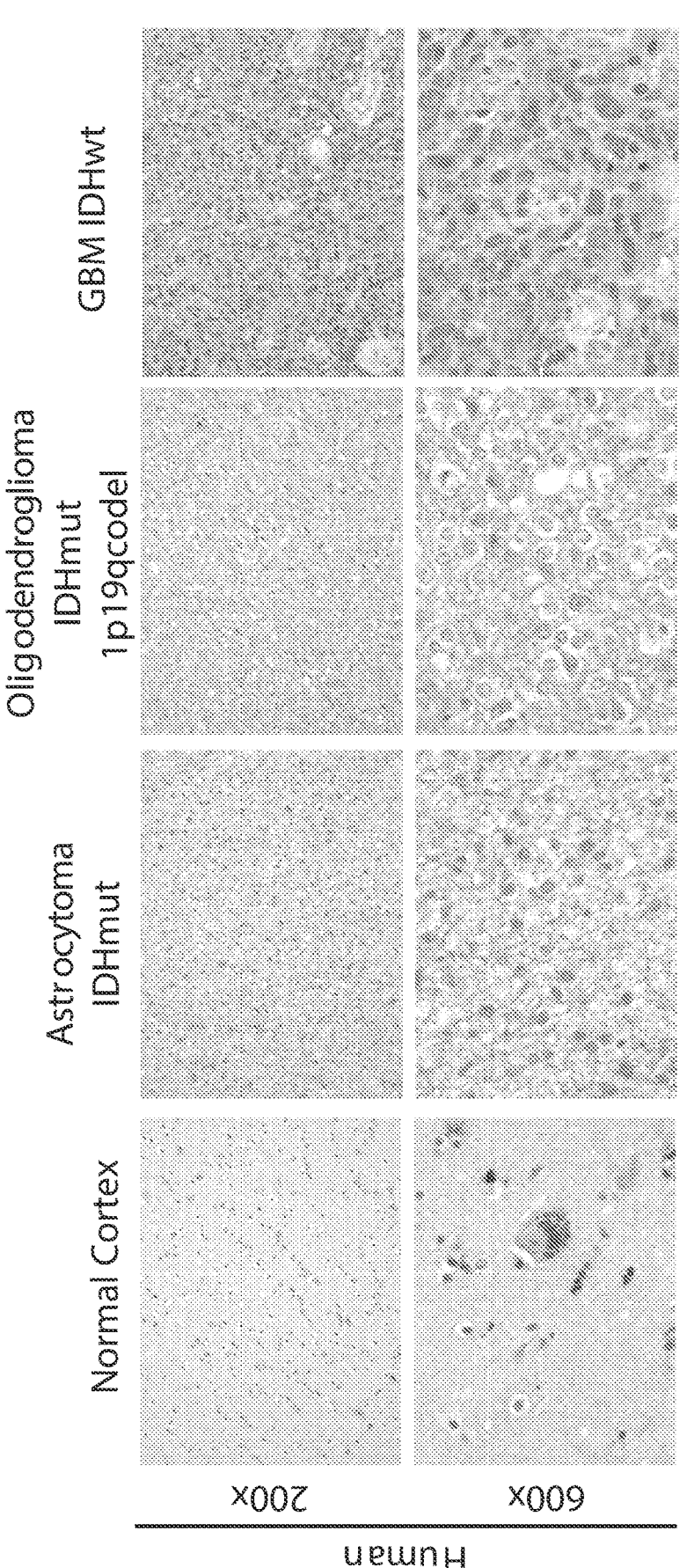

Predominant TrkB.T1 expression in gliomas (FIGS. 1A-1C) combined with GO enrichment analysis data showing altered genesets involved in endocytic trafficking in brain tumors compared with normal brain (FIG. 2) suggested that TrkB.T1 localization may be altered in LGG and GBM. The next step was to compare the distribution and localization of TrkB.T1 in brain tumors compared with normal brain tissue. Formalin-fixed paraffin-embedded (FFPE) pathology tissue was reviewed by a neuropathologist and characterized according to three major integrated classifications of diffuse gliomas derived from the 2016 World Health Organization (WHO) classification of CNS tumors: Oligodendroglioma, IDH-mutant and 1p/19q-codeleted (n=5); Astrocytoma/Glioblastoma, IDH-mutant (n=5); and Astrocytoma/Glioblastoma, IDH-wild-type (WT) (n=14 total; n=5 classical, n=4 proneural, n=5 mesenchymal). Pathological review of tumor sections confirms that TrkB.T1 staining is intensely diffuse throughout all CIMP and non-CIMP tumors. Specifically, these tumors lack punctate intracellular clustering of the receptor seen in non-neoplastic cells, demonstrating that both the expression and distribution of TrkB.T1 differ in normal brain compared with gliomas, providing a degree of visual specificity and receptor localization that was previously not possible. Diffuse gliomas of all classifications demonstrated patchy to widespread, moderately intense, cytoplasmic TrkB.T1 immunohistochemical staining with noticeable lack of normative vesicular pattern (FIG. 3C).

Figure 3D:
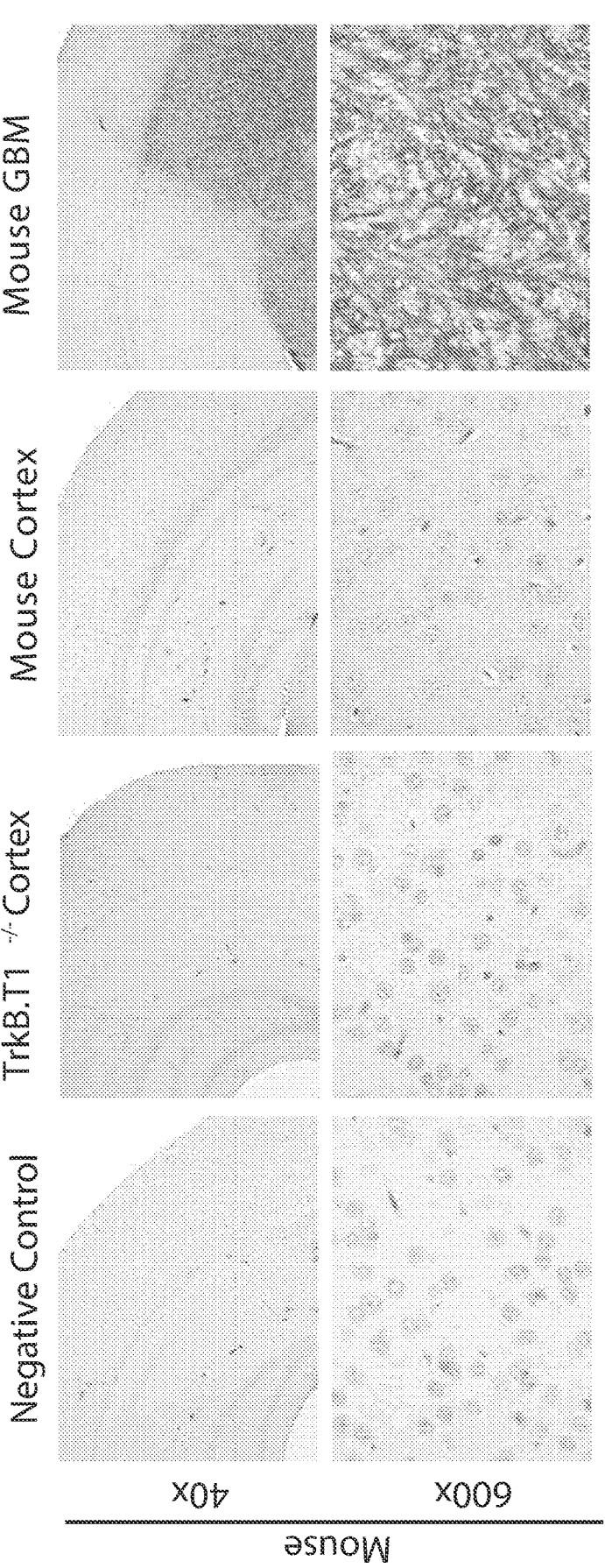

TrkB.T1 IHC on normal mouse cortex recapitulated the cytoplasmic vesicular staining found in normal human cortex and this pattern was completely absent in TrkB.T1$^{-/-}$ brain (FIG. 3D). Archived samples of several different RCAS/tv-a mouse models of glioma including those driven by PDGF and those driven by loss of combined NF1 and PTEN or EGFRvIII were then stained. All mouse glioma models analyzed, regardless of strain, genetic background, or oncogenic driver showed strong diffuse staining for expression of endogenous TrkB.T1 within the tumor boundaries (FIG. 3D), suggesting that TrkB.T1 may be selected for as the predominant NTRK2 isoform across multiple tumor types. These patterns observed in normal mouse brain and mouse gliomas match those seen in normal human brain and human glioma described above (FIG. 3D). As an internal control, TrkB.T1 immunostaining was negative in human glioma stromal blood vessels (not shown) and TrkB.T1$^{-/-}$ mouse cortex (FIG. 3D). These tumors also showed little to no staining for TrkB.FL when stained with an antibody developed against amino acid 810 of the TrkB kinase domain (which therefore detects TrkB.FL, but not TrkB.T1), which is in contrast to normal mouse cortex and TrkB.T1$^{-/-}$ cortex where TrkB.FL is present at moderately high levels (not shown). To ensure IHC on mouse tumors was not an artifact of mouse-on-mouse reagents, a recombinant antibody with a rabbit FC region that could be detected with anti-rabbit secondary antibodies was also created, which showed similar IHC results (not shown).

TrkB.T1 Enhances PDGF-Driven Gliomagenesis In Vivo

Given the differences in TrkB.T1 expression and distribution in normal brain and gliomas in both humans and mice, the next step was to explore the role of TrkB.T1 in glioma biology utilizing the RCAS/tv-a system, which allows somatic transfer TrkB.T1 into specific cell types of genetically altered mice. RCAS-TrkB.T1 injected into the brains of postnatal day (P)1 N/tv-a (Nestin-expressing cell of origin) wild-type mice significantly enhanced glioma formation as evidenced by decreased survival in mice injected with RCAS-PDGFB+RCAS-TrkB.T1 compared with mice injected with RCAS-PDGFB only (RCAS-PDGFB+RCAS-TrkB.T1 vs. RCAS-PDGFB alone: median survival 34 days vs. 109 days, Mantel-Cox/log-rank hazard ratio 2.306, 95% confidence interval 0.8999 to 5.909, p<0.05) (FIG. 4A). In addition to strong immunostaining of TrkB.T1 across genetically diverse RCAS-driven gliomas (described above), additional analysis of genetically diverse mouse tumorsphere lines reveals increased expression of TrkB.T1 compared with TrkB.FL (FIG. 4B) suggesting that while overexpression TrkB.T1 can enhance PDGF-driven gliomas in vivo, this variant also predominates over TrkB.FL in all rodent gliomas analyzed and may be selected for in an oncogenic context. FIG. 4B illustrates results of qRT-PCR analysis, which were recapitulated in western analysis (not shown).

The present NTRK2 transcript-level analysis of normal brain and human gliomas reveals relatively low amounts of full-length TrkB.FL compared with abundant amounts of TrkB.T1 in tumor tissue, suggesting that this isoform has an important role in both normal neurobiology and oncogenesis alike. Subcellular distribution patterns of this TrkB.T1 suggest potentially distinct roles for neuronal and glial cell populations in normal brain, whereas as the lack of vesicular pattern in CIMP and non-CIMP tumors highlights the need for further characterization of differences in signaling mechanism as a result of receptor compartmentalization. As mentioned above, in addition to endocytic and vesicular compartment GO terms (as shown in FIG. 2), DGCA GO analysis for positive NTRK2 correlations in glioma reactome pathways revealed enrichment for genes in the PI3K and mTOR signaling pathways (not shown), which have been known to regulate cellular proliferation in normal and oncogenic contexts. Previous work has shown that TrkB.T1 enhances both apoptosis and proliferation of neurospheres leading to larger sphere diameter and RCAS-TrkB.T1 delivery to N/tv-a isolated neurospheres recapitulates this phenomenon, as shown by the increased size of neurospheres infected with RCAS-TrkB.T1 compared with control neurospheres. Briefly, neural stem cells were isolated from subventricular zone of nestin/tv-a wild-type postnatal day 1 (P1) pups were infected with RCAS-GFP or RCAS-TrkB.T1 and allowed to form neurospheres. Measurements of the neurospheres demonstrated enhanced neurosphere diameter in RCAS-TrkB.T1 spheres. (not shown). This suggests that the TrkB.T1 isoform can influence the replicative capacity of progenitors in dual systems.

TrkB.T1 Enhances Perdurance of PDGF-Induced Signaling

To further characterize which signaling pathways may be active in TrkB.T1 gliomas, 3T3/tv-a cells were maintained as previously described (Ozawa, T. et al. Most human non-GCIMP glioblastoma subtypes evolve from a common proneural-like precursor glioma. *Cancer Cell* 26, 288-300 (2014)) Most human non-GCIMP glioblastoma subtypes evolve from a common proneural-like precursor glioma. *Cancer Cell* 26, 288-300 (2014)) and infected with RCAS-TrkB.T1 to explore potential mechanistic links for these effects. These cells were chosen for their lack of endogenous TrkB receptor expression so that effects of TrkB.T1 could not be confounded with potential interaction with TrkB.FL. Western blot was performed to establish efficiency of RCAS-TrkB.T1 in 3T3/tv-a cells in relation to normal mouse brain and TrkB.T1$^{-/-}$ brain control (not shown). In order to explore if TrkB.T1 can enhance growth factor signaling in vitro, 3T3/tv-a cells were treated with PDGF-BB ligand, chosen for its role in glioma biology, for varying durations and lysates were subjected to western blot analysis to explore downstream targets often implicated in gliomagenesis. TrkB.T1-expressing 3T3/tv-a cells showed significantly enhanced and sustained levels of phospho-STAT3, phospho-AKT, phospho-S6rp, and slight increases in phospho-ERK in response to PDGF treatment. Briefly, western blot analysis demonstrated TrkB.T1-expressing 3T3/tv-a cells exhibit enhanced pSTAT3, pAKT, pS6rp, pERK signaling in response to 10 ng/ml PDGF-BB treatment over the course of 36 h (repeated in duplicate or triplicate). TrkB.T1-expressing 3T3/tv-a cells demonstrated enhanced phosphorylation of PDGFR-β (Y1021) and maintained expression of total PDGFR-β upon ligand stimulation (not shown). This suggests a role for TrkB.T1 in enhancing perdurance of certain components of PDGF signaling, potentially through altered endocytic trafficking, tyrosine kinase receptor cross-talk, sustained membrane insertion or recycling of PDGFR-β. TrkB variants, in general, have been shown to alter default recycling pathways and exhibit cross-talk with other tyrosine kinases in different cancer types, suggesting that interactions with other signaling cascades have yet to be elucidated.

While rapid downregulation of PDGFβ receptors has been observed upon ligand activation, similar downregulation of transactivated PDGFβ receptors has not. Furthermore, transactivation of PDGF-β and TrkB receptors has been shown to occur in unique contexts, such as in neuroblast cells under low concentrations of reactive oxygen species (ROS). Western blot analysis of phosphorylated (p)PDGFR-β and total PDGFR-β demonstrate that there is enhanced pPDGFR-β in TrkB.T1-expressing 3T3/tv-a cells and also a maintained expression of total PDGFR-β upon ligand stimulation (described above). Future biochemical studies characterizing the precise role of TrkB.T1 in the recycling, stabilization, or degradation PDGFR-β will shed light on how this interaction achieves the downstream signaling effects described above and in vivo effects observed in FIG. 4A.

GO Analysis of GSCs Stratified by TrkB.T1 Expression

To explore the correlations between TrkB.T1 levels and GO terms in human tumor initiating GBM stem cells (GSCs), whole gene expression data was obtained from four previously published human GSC lines derived from patient tumors. Two classical/proneural lines were chosen—GSC line 559 was defined as TrkB.T1 Low with TrkB.T1 transcript FPKM values of 1.86, 0.84, and 0.81 for triplicate wells, while GSC line 448 was defined as TrkB.T1 High with FPKM values of 74.94, 58.80, 45.68. Differentially expressed genes were found between these two classical/proneural cell lines (FIG. 5) (545 significantly upregulated genes and 704 significantly downregulated genes, adjusted p-value (FDR)<0.05 with a fold change of more than 2 in each respective direction). PCA plots show distinct clusters for the TrkB.T1 High GSC line (488) compared with the TrkB.T1 Low GSC (559) line in the classical/proneural lines and distinct (not shown). To explore potential pathways involved with high and low TrkB.T1 expression in vitro, GO analysis was performed, which revealed downregulated cellular compartment genesets involved in coated vesicle membranes, clathrin-coated vesicle membranes, clathrin coated endocytic vesicle membranes, endocytic vesicle membrane, and clathrin-coated endocytic vesicles in the TrkB.T1 High line (488) compared with TrkB.T1 Low line (559) (not shown) suggesting endocytic vesicles and receptor trafficking may be altered in TrkB.T1 High vs TrkB.T1 Low contexts. Because normal human brain exhibits relatively lower TrkB.T1 levels, and more punctate TrkB.T1 staining, compared with both GBM and LGG (FIGS. 1A-1C), these differentially expressed GSC genesets are compatible with the differences in TrkB.T1 distribution shown in FIGS.

Figure 5:
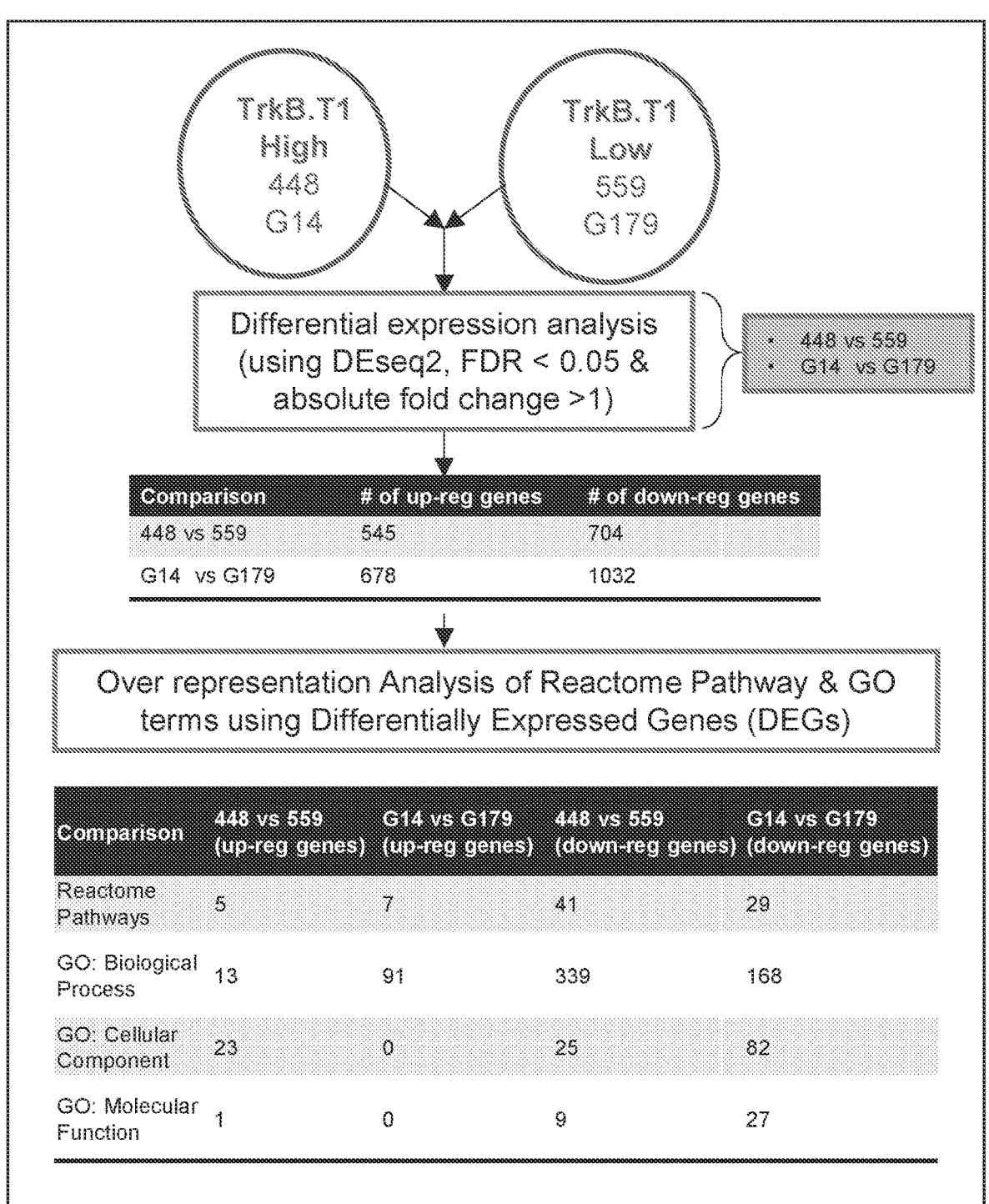
FIG. 5 is a schematic for differential gene expression analysis between TrkB.T1 High (classical/proneural replicates 448 1-3; classical/mesenchymal G14 replicates 1-3) and TrkB.T1 Low (classical/proneural replicates 559 replicates 1-3; classical/mesenchymal G179 replicates 1-3).

3A-3D. GO analysis also revealed downregulated molecular function genesets in TrkB.T1 High (488) compared with TrkB.T1 Low (559) GSC lines involved in platelet-derived growth factor binding and transcriptional activity, further highlighting the potential role for TrkB.T1 PDGF-regulated signaling (e.g., FIG. 4A). To confirm that TrkB.T1 specific terms were not specific to classical/proneural lines, a second pair of classical/mesenchymal GSC lines was separately analyzed. (FIG. 5). The GSC line G179 was defined as TrkB.T1 Low with TrkB.T1 transcript FPKM values of 2.12, 1.70, and 1.50 for triplicate wells, while GSC line G14 was defined as TrkB.T1 High with FPKM values of 41.78, 37.48, 34.38. Differentially expressed genes were found between these two classical/mesenchymal cell lines (FIG. 5) (678 significantly upregulated genes and 1032 significantly downregulated genes, adjusted p-value (FDR)<0.05 with a fold change of more than 2 in each respective direction) (not shown).

TrkB.T1 Upregulates PI3K/Akt Pathway Genes in Neural Stem Cells (NSCs)

To explore the causal role of TrkB.T1 in normal cells, TrkB.T1, TrkB.FL, and GFP were cloned into pLJM1 lentiviral vectors to infect NSCs and performed RNA-sequencing. TrkB.FL-transduced NSCs showed increased levels of TrkB.FL RNA, and protein as validated by western blot (not shown). TrkB.T1 transduced NSCs showed increases in TrkB.T1 RNA and protein and also exhibit increases in gene signatures previously characterized as a marker of a cell's proliferative index, compared with TrkB.FL (not shown). It was found that while each infected line clustered independently (i.e., generating a cluster dendrogram and principal component analysis; not shown), differential expression analysis revealed that 17 genes were significantly upregulated in TrkB.T1 infected NSCs compared with TrkB.FL infected NSCs (adjusted p-value <0.05 and fold change more than 25%). GO enrichment analysis on these upregulated genes revealed a predominance of terms in the PI3K/Akt pathway and the PI3K/ERBB2/ERBB4 pathway (not shown), suggesting that while TrkB.T1 is indeed capable of enhancing PDGF-induced Akt signaling as shown above (FIG. 4B), it may also have more general effects on basal PI3K/AKT signaling in the absence of exogenous ligand, highlighting the generalizability of TrkB.T1-PI3K/AKT interactions across various cell types.

Treatment of NSCs transduced with TrkB.FL and TrkB.T1 showed that both lines were sensitive to phosphoinositide-3 kinase (PI3K) and mTOR inhibitors (LY294002 and rapamycin, respectively) in a dose dependent manner and that TrkB.T1 NSCs were marginally, but statistically significantly, more sensitive to LY294002 than TrkB.FL NSCs at both 48 hours (F(1,24)=10.03; p=0.0042) and at 72 hours (F(1,24)=12.91; p=0.0015) (not shown). For rapamycin drug studies, n=3 plates of TrkB.T1-transduced NSCs and 3 plates of TrkB.FL-transduced cells for each time point (3 plates of each condition for 48 hrs, 3 plates of each condition for 72 hrs). For LY294002 drug studies, n=3 plates of TrkB.T1-transduced NSCs and 3 plates of TrkB.FL-transduced cells were used for each time point (3 plates of each condition for 48 hrs, 3 plates of each condition for 72 hrs). Combined with RNASeq data suggesting a role for TrkB.T1 in PI3K signaling and enhancement of downstream PDGFR pathways in vitro (e.g., FIGURE A and as described above), increased sensitivity to LY294002 in the TrkB.T1 NSCs suggests that TrkB.T1 may selectively activate PI3K pathways.

Similar to TCGA DGCA and GSC data, there were also significant differences in gene expression between TrkB.T1 and TrkB.FL NSCs for genes involved in endocytic vesicles, vesicular trafficking, and vesicular transport (not shown). TrkB.T1 NSCs also exhibited downregulation of several MHC Class II genes, including HLA-DRB1, HLA-DRB5, HLA-DMA, HLA-DRA1, as well as the master transcriptional activator controlling expression of MHC Class II genes CIITA (not shown), highlighting the possibility that along with enhancing PDGF-driven signaling in vivo, the increased levels of TrkB.T1 observed in gliomas (FIGS. 1A-1C) may also harbor a role in modulating antigen-specific immune responses that are often dysregulated cancer.

Discussion

NTRK2's suspected oncogenic role has long centered around the sole possibility of constitutive activation of the TRK kinase, which has more recently been highlighted in NTRK2 kinase-activating fusions. While current TRK inhibitors are being developed and being used clinically with some success, it is unclear of the overall specificity of these compounds and if the targeted kinases are being activated independently or through more paracrine mechanisms. The data shown here reveal a kinase-deficient isoform, TrkB.T1, to be the predominant isoform in brain tumors compared with normal brain, which is contrary to the notion that the TrkB's own kinase is the sole oncogenic driver. While the specificity of the 11 exons comprising TrkB.T1's C-terminus is unclear, it remains conserved across species at the amino acid level, highlighting the possibility for an evolutionarily selected function on its own or through interaction with nearby receptor tyrosine kinases. The in-depth transcript level analyses described here suggest additional components of NTRK2 biology may be implicated in gliomas. TrkB.T1 exhibits distinct granular and vesicular patterning in normal human and mouse brain and a more diffuse, mis-localized pattern in neoplastic brain (in both mice and humans). In addition to altered receptor localization, TrkB.T1 is not only elevated in human gliomas, but also in murine gliomas driven by multiple genetic mechanisms, and across human and rodent GSC and tumorsphere lines. The described data show that while PDGF drives tumors with elevated levels of endogenous TrkB.T1, forced expression of TrkB.T1 makes these tumors more aggressive. TrkB.T1 is also capable of enhancing downstream targets of PDGF signaling in vitro, including Akt, STAT3, and pS6, and future studies should explore if this is a PDGF-specific effect or a more general effect of TrkB.T1 exhibiting crosstalk with other receptor tyrosine kinases to explore whether this phenomenon may be applicable to other tumor types beyond gliomas. Next generation sequencing of human NSCs reveals that TrkB.T1 overexpression upregulates genes in PI3K/Akt pathways and PI3K events in ERBB2 (HER2)/ERBB3/ERBB4 signaling suggesting that TrkB.T1 may have more general effects on PI3K/Akt biology than just amplifying Akt activity resulting from stimulation with PDGF ligand. Future work should investigate the role of TrkB.T1 in PI3K/Akt pathways and PI3K/ERBB2/ERBB3/ERBB4 networks across various cancer types, as western blots (corresponding to RNASeq data) show upregulation of ERBB3 receptor in TrkB.T1 transduced NCS, along with increased expression NRG2, a ligand for ERBB3 and ERBB4 (not shown).

Despite recent advances in diagnostics and characterization of glioma subtypes, survival rates for certain cancers, such as GBM, remain extremely poor, highlighting the need for novel therapeutic targets. As bioinformatic tools now offer more complex analytical approaches, it is possible that unique receptor splice variants, such as TrkB.T1, may prove to be crucial for understanding glioma biology, and oncogenic signaling in general. The present data suggest that TrkB.T1 has a unique distribution pattern throughout the normal brain and that shifts in expression and distribution of this splice variant may harbor distinct roles in oncogenesis within and outside the CNS either independently from or in conjunction with a wide array of growth factors, kinases, or even simultaneous NTRK2 fusions. It is of interest to note that in many cases of novel NTRK2 gene fusions, the TrkB.T1 isoform is still able to be generated in its full form from the reciprocal cross, if the fusion breakpoint is downstream of the unique TrkB.T1 exon. The possibility exists that in addition to creating constitutively active kinases through various fusion partners, these fusions may, in some cases, also be inherently selecting for the production of TrkB.T1. Similarly, analysis of mouse tumorspheres generated with NTRK2 fusions shows that they express TrkB.T1 as their most highly expressed isoform. As treatment failure after initial response to TRK inhibitors, such as larotrectinib or entrectinib, is becoming frequently observed with continued use, teasing apart the exact roles of specific functional domains of NTRK genes will become crucial for understanding and maintaining clinical efficacy. While the importance of a constitutively active TRK kinase should not be overlooked clinically, it will become increasingly important to tease apart the role of TrkB.T1's role in tumors with- and without-NTRK2 fusions.

Materials and Methods

Bioinformatic Analysis

Obtaining and transforming gene level data. Publicly available whole gene RPKM read counts for TCGA-LGG and TCGA-GBM were downloaded from UCSC's Xena Browser (xenabrowser.net/datapages/?host=https://tcga.x-enahubs.net). CIMP and nonCIMP status for TCGA-GBM (Ceccarelli, M. et al. Molecular profiling reveals biologically discrete subsets and pathways of progression in diffuse glioma. *Cell* 164, 550-563 (2016)) and TCGA-LGG (Cancer Genome Atlas Research, N. et al. Comprehensive, integrative genomic analysis of diffuse lower-grade gliomas. *N Engl. J. Med.* 372, 2481-2498 (2015)) samples were obtained from Bolouri et al. Big data visualization identifies the multidimensional molecular landscape of human gliomas. Proc. Natl Acad. Sci. USA 113, 5394-5399 (2016)). Whole gene RPKM read counts for The GTEx Project (v6) (Consortium, G. T. Human genomics. The genotype-tissue expression (GTEx) pilot analysis: multitissue gene regulation in humans. *Science* 348, 648-660 (2015)) was obtained from the web at //gtexportal.org/(version 6) on Mar. 30, 2017 (dbGaP accession number phs000424.v7.p2). GTEx is supported by the Common Fund of the Office of the Director of the National Institutes of Health, and by NCI, NHGRI, NHLBI, NIDA, NIMH, and NINDS. Whole gene counts from GTEX and TCGA was transformed to log 2(rpkm+1) using R [(version 3.3.2) (R Core Team (2017). R: A language and environment for statistical computing. R Foundation for Statistical Computing, Vienna, Austria. URL: R-project.org/)].

Obtaining and transforming transcript level data. Transcript Data (TCGA RNAseqV2 RSEM data) for TCGA-GBM and TCGA-LGG was downloaded from the legacy archive of TCGA. Transcript data (RPKM data) was also downloaded from GTEx(v6) website. To make the RSEM data from TCGA, and RPKM data comparable, both data sets were converted to TPM (transcripts per million). The RSEM counts from TCGA to TPM counts using the following formula (Li, B. & Dewey, C. N. RSEM: accurate transcript quantification from RNA-Seq data with or without a reference genome. *BMC Bioinforma.* 12, 323 (2011)): RSEM can be multiplied by $10^6$. The RPKM transcript data from GTEX was converted to TPM data using the formula (Li, B. & Dewey, C. N., *BMC Bioinforma.* 12, 323 (2011)) TPM=RPKM/(sum of RPKM over all genes/transcripts)× $10^6$. For transcript analyses, NTRK2 transcript IDs were manually aligned to confirm sequence homology and are as follows: TrkB.FL (UCSC: uc004aoa.1; Ensembl: ENST00000376213.1, NTRK2_201), TrkB.T1 (UCSC: uc004aob.1; Ensembl: ENST00000395882.1, NTRK2_204).

RNA Seq analysis for 448 vs 559 and G14 vs G179 GSC cell lines. Raw gene counts for cell line 448, 559, G14, and G179 were obtained from GEO repository, (GSE89623) (Pollak, J. et al. Ion channel expression patterns in glioblastoma stem cells with functional and therapeutic implications for malignancy. *PLoS ONE* 12, e0172884 (2017)). Cufflinks (Trapnell, C. et al. Transcript assembly and quantification by RNA-Seq reveals unannotated transcripts and isoform switching during cell differentiation. *Nat. Biotechnol.* 28, 511-515 (2010)) results for TrkB.T1 were used to differentiate the 4 cell lines into TrkB.T1 High (448, G14) and TrkB.T1 Low (559, G179) groups. Differential Gene Expression analysis was performed between TrkB.T1 High and TrkB.T1 Low (448 vs 559, G14 vs G179) cell lines using the R/Bioconductor package DESeq2 (Love, M. I., Huber, W. & Anders, S. Moderated estimation of fold change and dispersion for RNA-seq data with DESeq2. *Genome Biol.* 15, 550 (2014)) and a statistical cutoff of FDR <0.05 and FC>2 was applied to obtain differentially regulated genes.

RNA Seq analysis for NSC cell lines. RNA-seq reads were aligned to the UCSC hg19 assembly using STAR2 (Dobin, A. et al. STAR: ultrafast universal RNA-seq aligner. *Bioinformatics* 29, 15-21 (2013)) and counted for gene associations against the UCSC genes database with HTSeq (Anders, S., Pyl, P. T. & Huber, W. HTSeq—a Python framework to work with high-throughput sequencing data. *Bioinformatics* 31, 166-169 (2015)). Differential Gene Expression analysis was performed between GFP vs TrkB.T1 NSCs, GFP vs TrkB.FL NSCs, and TrkB.T1 vs TrkB.FL NSCs, using the R/Bioconductor package edgeR (Robinson, M. D., McCarthy, D. J. & Smyth, G. K. edgeR: a Bioconductor package for differential expression analysis of digital gene expression data. Bioinformatics 26, 139-140 (2010)) and a statistical cutoff of FDR<0.05 and FC>1.25 was applied to obtain differentially regulated genes. Raw data files have been deposited to the NCBI Gene Expression Omnibus under accession number GEO: (GSE136868)

Downstream analysis. For PCA plots, the R function 'dist' was used to calculate Euclidean distance between samples. The PCA was computed for the above distances and visualized it using R package ggplot2 (v 2.2.1). Transcript Data was visualized using boxplots using R package ggplot2 (Wickham, H. Ggplot2: elegant graphics for data analysis, viii, 212 p. (Springer, New York, 2009)). Whole gene correlations between Normal Brain Data from GTEX and LGG, GBM data from TCGA was calculated using R package DGCA (on the web at //cran.r-project.org/web/packages/DGCA/index.html). For predominant transcript analysis, log 2 TPM values for each transcript were compared and each sample from pooled normal brain (GTeX), LGG (TCGA) and GBM (TCGA) was marked as either TrkB.T1 or TrkB.FL, depending on which transcript, of the two, had the greater value. GO and Reactome Pathway enrichment analysis (Jassal, B. et al. The reactome pathway knowledgebase. *Nucleic Acids Res.* 48, D498-D503 (2020); Fabregat, A. et al. The reactome pathway knowledgebase. *Nucleic Acids Res.* 46, D649-D655 (2018)) was done using R Bioconductor Packages clusterProfiler v 3.4.4 (Yu, G., Wang, L. G., Han, Y. & He, Q. Y. clusterProfiler: an R package for comparing biological themes among gene clusters. OMICS 16, 284-287 (2012)) and dot plots were made using R Bioconductor package DOSE (Yu, G., et al. DOSE: an R/Bioconductor package for disease ontology semantic and enrichment analysis. *Bioinformatics* 31, 608-609 (2015)). Heatmaps were made using R package pheatmap (on the web at //CRAN.R-project.org/package=pheatmap).

GSC transcript analysis. The human GSCs dataset represented in FIGS. 1A-1C consists of 44 samples from GSE119834 (Mack, S. C. et al. Chromatin landscapes reveal developmentally encoded transcriptional states that define human glioblastoma. *J. Exp. Med.* 216, 1071-1090 (2019)) and 6 additional lines (BTSC349, BTSC349, h543, h516, h561, and h676) from GSE150653. For the newly generated data, sequencing libraries were prepared with the NEBNext Ultra II Directional RNA Library Prep Kit for Illumina (NEB #E7760) as recommended by the kit manufacturer and then sequenced with an Illumina NexSeq 550. RNA-seq samples were analyzed using the nextpresso pipeline (Graña, O., et al. Nextpresso: next generation sequencing expression analysis pipeline. *Curr. Bioinform.* 13 (2018)) as follow: reads were aligned to the human genome (hg19) with TopHat-2.0.10 (Trapnell, C. et al. Differential gene and transcript expression analysis of RNA-seq experiments with TopHat and Cufflinks. *Nat. Protoc.* 7, 562-578 (2012)) using Bowtie 1.0.0 (Langmead, B., Trapnell, C., Pop, M. & Salzberg, S. L. Ultrafast and memory-efficient alignment of short DNA sequences to the human genome. *Genome Biol.* 10, R25 (2009)) and SAMtools 0.1.19 (Li, H. et al. The sequence alignment/map format and SAMtools. *Bioinformatics* 25, 2078-2079 (2009)), allowing 3 mismatches and 20 multi-hits; transcripts quantification was calculated with Cufflinks 2.2.1 (Trapnell, C. et al., *Nat. Protoc.* 7, 562-578 (2012)), using the human hg19 transcript annotations from //ccb.jhu.edu/software/tophat/igenomes.shtml. Transcriptional subtypes were obtained using the 'ssgsea.GBM.classification' R package (Wang, Q. et al. Tumor evolution of glioma-intrinsic gene expression subtypes associates with immunological changes in the microenvironment. *Cancer Cell* 32, 42-56 e6 (2017)), through the SubtypeME tool of the GlioVis web portal (//gliovis.bioinfo.cnio.es) (Bowman, R. L., et al. GlioVis data portal for visualization and analysis of brain tumor expression datasets. *Neuro Oncol.* 19, 139-141 (2017)).

Mouse Tumorspheres

Mouse tumorspheres from Oldrini, B. et al., Somatic genome editing with the RCAS-TVA-CRISPR-Cas9 system for precision tumor modeling. *Nat. Commun.* 9, 1466 (2018), deposited in GSE110700, were analyzed for NTRK transcript expression, as above, and subjected to immunoblotting and RT-qPCR.

Immunoblotting. Lysates were prepared in RIPA lysis buffer (20 mM Tris-HCl, 150 mM NaCl, 1% NP-40, 1 mM EDTA, 1 mM EGTA, 1% sodium deoxycholate, 0.1% SDS) and protein concentrations were determined by DC protein assay kit (Biorad, Cat. 5000111). Proteins were run on a 8% SDS-PAGE gel and transferred to nitrocellulose membrane (Amersham, Cat. GEHE10600003). After blocking the membrane in 5% milk, 0.1% Tween, 10 mM Tris at pH 7.6, 100 mM NaCl, primary antibodies TrkB (Merck, Cat.

07-225; lot: 3277578 at 1:3000) and vinculin (Sigma-Aldrich, Cat. V9131; lot: 118M4777V at 1:10.000) were added. Anti-mouse or rabbit-HRP conjugated antibodies (Jackson Immunoresearch) were used to detect desired protein by chemiluminescence with ECL (Amersham, RPN2106).

Reverse transcription quantitative PCR RNA was isolated with TRIzol reagent (Invitrogen, Cat. 15596-026) according to the manufacturer's instructions. For reverse transcription PCR (RT-PCR), 1 µg of total RNA was reverse transcribed using the High Capacity cDNA Reverse Transcription Kit (Applied Biosystems, Cat. 4368814). Quantitative PCR was performed using the SYBR-S elect Master Mix (Applied Biosystems, Cat. 4472908) according to the manufacturer's instructions. qPCR was run using specific primers for TrkB.T1 (qmNtrk2T1Fw_CAGGTAGAACGGAGCAGCA (SEQ ID NO:3) and qmNtrk2T1RevA_GGTTAGCAGAGGGCAATGGA (SEQ ID NO:4)) and the TrkB.FL (qmNtrk2FLFwdA_TTCCTTGCCGAGTGCTACAA (SEQ ID NO:5) and qmNtrk2FLRevA_TCGTGCTGGAGGTTGGTC (SEQ ID NO:6)). The threshold cycle number for the genes analyzed was normalized to GAPDH (mGAPDHFwd_T-CAACAGCAACTCCCACTCTTCCA (SEQ ID NO:7) and mGAPDHRev_ACCCTGTTGCTGTAGCCGTATTCA (SEQ ID NO:8)).

Generation of Monoclonal Antibody to TrkB.T1

Murine monoclonal antibody (clone FH1D12) was generated at the Fred Hutchinson Antibody Technology Core Facility. Briefly, male and female 20-week-old C57BL6 mice that were characterized as genetic null for TrkB.T1 (Dorsey, S. G. et al.) In vivo restoration of physiological levels of truncated TrkB.T1 receptor rescues neuronal cell death in a trisomic mouse model. Neuron 51, 21-28 (2006)) were immunized with TrkB.T1 peptide Ac—C(dPEG4) FVLFHKIPLDG-OH (SEQ ID NO:1) maleimide coupled to KLH carrier protein. Following a 12+ week boosting protocol splenocytes were isolated from high titer mice and electrofused to a subclone of the P3x63-Ag8 myeloma cell line (BTX, Harvard Apparatus). Hybridomas secreting peptide specific antibody were identified and isolated using a ClonePix2 (Molecular Devices, CPII) colony picker. Antibodies from the picked clones were validated for peptide binding by flow cytometry using a cytometric bead array carrying the target peptide. Clone FH1D12 was subcloned (CPII) followed by validation for peptide binding by bead-based flow cytometry. Affinity purified IgG2b lambda from the hybridoma was further characterized by Western blot analysis and IHC tissue staining. Antibody development was performed in Holland Lab and with the Antibody Technology Resource (Fred Hutchinson Cancer Research Center).

Wes™ capillary electrophoresis for antibody development. Protein Simple Wes™ was used at two stages of antibody screening: Stage 1, selecting immunized mice to advance for hybridoma generation, and Stage 2, for validation of monoclonal antibodies that Western blot full-length TrkB.T1 protein in murine brain detergent extracts. Briefly, mouse brain lysates from TrkB.T1$^{+/+}$ and TrkB.T1$^{-/-}$ mice were prepared by mechanical disruption (Dounce tissue homogenizer, Kimble Chase) in RIPA lysis buffer (Pierce™ RIPA Lysis and Extraction Buffer, ThermoScientific™) containing HALT™ Protease and Phosphatase Inhibitor Cocktail and EDTA (ThermoScientific™) and normalized to 2 µg/µl total protein via Bradford Protein Assay. Approximately 8-10 ng total brain extract protein was loaded into the Protein Simple Capillary WES system for Western analysis following Protein Simple recommended methods (Rustandi, R. R., et al. Applications of an automated and quantitative CE-based size and charge western blot for therapeutic proteins and vaccines. Methods Mol. Biol. 1466, 197-217 (2016)). Mice with antisera (1:2500 dilution in PBS and Antibody Diluent (Protein Simple)) that identified a positive band at 90-100 kDa for the TrkB.T1 protein were advanced forward for final boosting, splenectomy, and hybridoma generation (FIG. 3B). For Stage 2, antibodies from monoclonal culture super (diluted 1:2 in Antibody Diluent (Protein Simple)) targeting the TrkB.T1 peptide (see hybridoma generation and screening) were further tested for their ability to Western blot full length TrkB.T1 protein from normal and KO mouse brain detergent extracts. Clone FH1D12 (and additional clones—FH1D6 and FH1E6) was identified as having positive Western blotting activity (FIG. 3B) positive immunostaining in the wild-type (WT) mouse brain and human brain with absent staining in the TrkB.T1$^{-/-}$ knockout mouse brain.

Figure 6A:
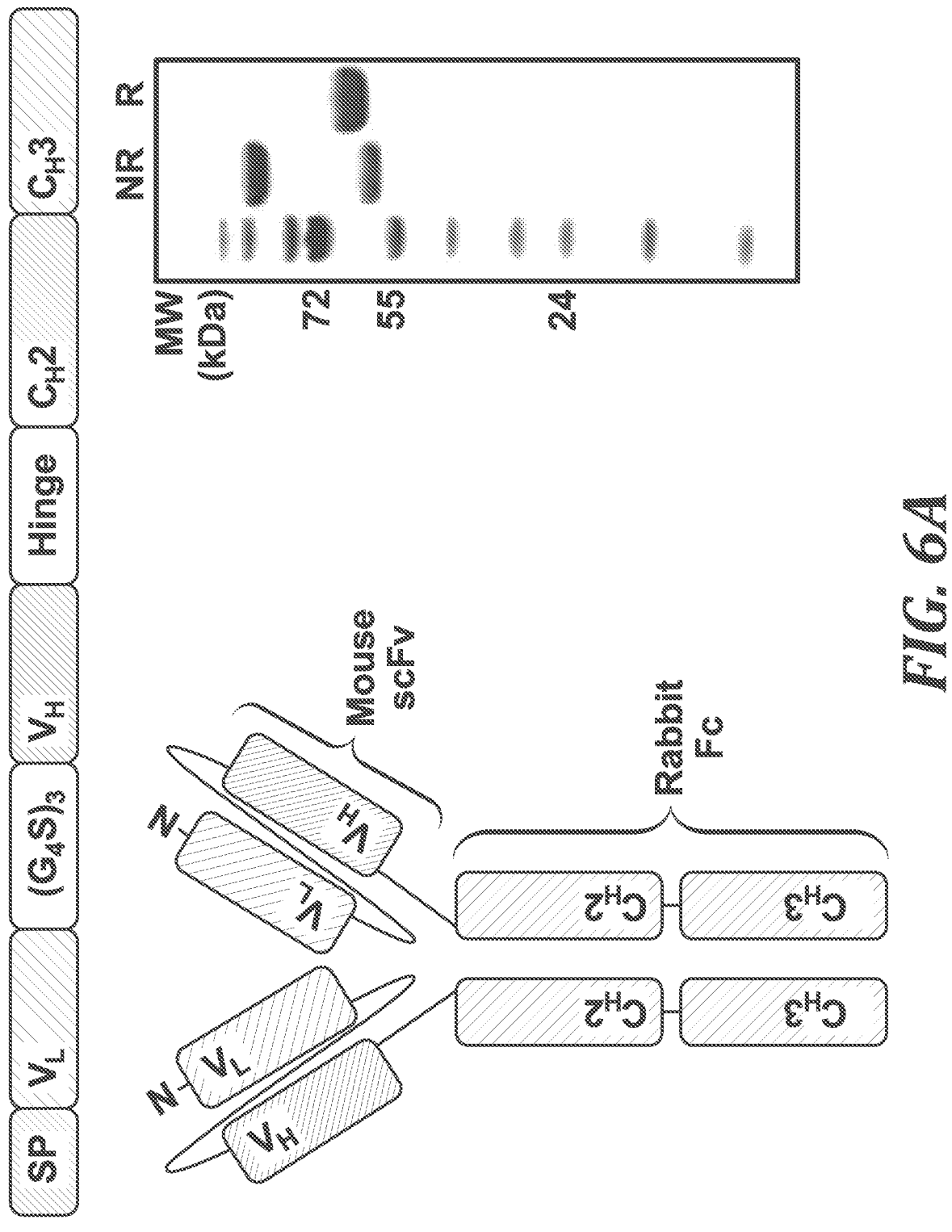
FIG. 6A is a schematic of fusion architecture of the SPEH1_D12 scFv-Fc fusion protein and including sodium dodecyl sulfate polyacrylamide gel showing the purified recombinant protein expressed in mammalian cells under non-reducing and reducing conditions.

Recombinant expression of TrkB.T1 SPEH1 D12 scFv-Fc fusion protein. The variable regions of the SPEH1_D12 (clone FH1D12) antibody were sequenced using rapid amplification of cDNA ends (RACE) cloning with standard primer sets and the SMARTer™ RACE 5'/3' kit (Clonetech). The variable regions were then formatted into a fusion construct containing a rabbit antibody Fc domain (FIG. 6). The amino acid sequence was then reverse translated using human codons, synthesized, and cloned into a custom lentiviral expression vector. The construct was expressed as a soluble protein using the Daedalus expression method (Bandaranayake, A. D. et al. Daedalus: a robust, turnkey platform for rapid production of decigram quantities of active recombinant proteins in human cell lines using novel lentiviral vectors. Nucleic Acids Res. 39, e143 (2011)) and purified using a 5 mL MabSelect Sure column (GE) (Bandaranayake, A. D. et al., Nucleic Acids Res. 39, e143 (2011)). Following purification, the protein was supplemented with 5% glycerol, snap frozen using liquid nitrogen, and stored at −80° C. Final stocks were 11.5 mg/ml in 85 mM Sodium Citrate 140 mM Tris-HCl with 5% glycerol.

Immunohistochemistry

Antibody validation phase—large batch IHC. Four-µm sections of a multi-tissue block containing human brain, mouse brain, TrkB.T1$^{-/-}$ mouse brain, a cell pellet overexpressing TrkB.T1 and a cell pellet without TrkB.T1 were cut and stained with the Leica Bond Rx (Leica Biosystems, Buffalo Grove, IL). Slides were pretreated with H$_2$ antigen retrieval buffer for 20 min. Endogenous peroxidase was blocked with 3% hydrogen peroxide for 5 min. A TCT protein block was applied for 10 min (0.05 M Tris, 0.15 M NaCl, 0.25% Casein, 0.1% Tween 20, pH 7.6). Supernatants from multiple boosting and pre-/post-fusion samples, along with antibody clone D12 were used at 1:20 and applied to the tissue for 30 min. The antibody was then detected using Leica Power Vision HRP Mouse specific polymer (Leica Biosystems catalog #PV6114) for 12 min and staining was visualized with Refine DAB (Leica Biosystems catalog #D59800) and a hematoxylin counterstain was used (Hematoxylin 50% in H$_2$O from Biocare catalog #NM-HEM-M). Mouse isotype control slides were included for each run (Jackson ImmunoResearch Laboratories) at 2 µg/ml. Digital images of IHC-stained slides were obtained at ×40 magnification (0.25 µm/pixel) using a whole slide scanner (ScanScope AT Turbo, Aperio) fitted with a 20×/0.75 Plan Apo objective lens and ×2 magnification changer (Olympus, Center Valley, Pa., USA). Images were saved in SVS format (Aperio), managed with server software (ImageServer, Aperio), and retrieved with a file management web interface (eSlideManager, Aperio). Histology and IHC for antibody validation was performed by Experimental Histopathology Shared Resources at Fred Hutchinson Cancer Research Center.

Mouse brain, mouse glioma, human brain, and human glioma. Immunohistochemical staining was performed on Sum formalin-fixed/paraffin-embedded tissue sections using a Discovery XT Ventana Automated Stainer (Ventana Medical Systems, Inc)., run using standard Ventana reagents and the Discovery ChromoDAB and Discovery OmniMAP antims HRP kits to ameliorate non-specific mouse-on-mouse background and standard Ventana reagents and Vector secondaries for staining with the TrkB.T1 SPEH1_D12 scFv-Fc fusion.

Human Tissue and Case Selection

Approval for the use of human subject material was granted by the University of Washington's Institutional Review Board (Study #44806 and #00002162). Archived FFPE pathology tissue were reviewed by a board-certified neuropathologist (P. J. C.) and classified according to the 2016 WHO classification of CNS tumors: Oligodendroglioma, IDH-mutant and 1p/19q-codeleted (n=5); Astrocytoma, IDH-mutant (n=5); and Glioblastoma, IDH-WT (n=14 total; n=5 classical, n=4 proneural, n=5 mesenchymal) (Louis, D. N. et al. The 2016 World Health Organization Classification of Tumors of the Central Nervous System: a summary. *Acta Neuropathol.* 131, 803-820 (2016); Cimino, P. J., et al. Primary gliosarcoma of the optic nerve: a unique adult optic pathway glioma. *Ophthal Plast. Reconstr. Surg.* 33, e88-e92 (2017)). Normal brain control tissue from rapid autopsies (n=5) was procured from the University of Washington's Neuropathology Core Brain Aging and Neurodegeneration Brain Bank. Each control case contained multiple brain regions, including cerebral cortex, cerebellum, hippocampus, subiculum, entorhinal cortex, and thalamus.

Mouse Tissue Processing

Mouse tissue (including normal brains, tumor bearing brains) were removed, fixed in 10% neutral-buffered formalin for a minimum of 72 h and embedded into paraffin blocks. 5 μm serial sections were cut from formalin-fixed paraffin-embedded specimens and mounted on slides.

NSC Experiments

Cell culture. GSC and NSC isolates were grown in NeuroCult NS-A basal medium (StemCell Technologies) supplemented with B27 (ThermoFisher), N2 (2× stock in Advanced DMEM/F-12 (ThermoFisher) containing 25 μg/mL insulin, 100 μg/mL apo-transferrin, 6 ng/mL progesterone, 16 μg/mL putrescine, 30 nM sodium selenite, and 50 μg/mL bovine serum albumin (Sigma)), and EGF and FGF-2 (20 ng/ml) (PeproTech) on laminin (Trevigen or in-house-purified)-coated polystyrene plates and passaged (Pollard, S. M. et al. Glioma stem cell lines expanded in adherent culture have tumor-specific phenotypes and are suitable for chemical and genetic screens. *Cell Stem Cell* 4, 568-580 (2009)). Cells were detached from their plates using Accutase (EMD Millipore).

Lentiviral production and infection. For virus production, pLJM1 (Addgene) constructs containing the NTRK2 inserts of interest (TrkB.FL, TrkB.T1, or GFP) were transfected into 293T cells, along with psPAX and pMD2.G packaging plasmids (Addgene), using polyethylenimine (Polysciences). Fresh media was added 24 h later and viral supernatant harvested 24 h after that. For infection of NSC-U5 cells, 1e$^5$ cells/well were seeded into 6-well plates. Lentivirus was used unconcentrated and cells were infected at a MOI<1 24 h after seeding. 72 h after seeding, selection was begun for cells successfully expressing the constructs using 2 μg/mL puromycin (for 3 days). Cells were expanded after selection to create a stable line and collected for RNAseq three weeks post infection.

PI3K and mTOR inhibitors. In order to assess the sensitivity of TrkB.T1 and TrkB.FL overexpressing NSCs to LY294002 and rapamycin, biological triplicates of each line were used, seeding 6×4000 cells per triplicate into four laminin coated 96-well plates. One day after seeding, LY294002 (Life Technologies™ #PHZ1144; Lot #76075413) and rapamycin (Life Technologies™ #PHZ1235; Lot #2142418) were dissolved in DMSO warmed to 37 degrees at 10 mM, diluted to 10 μM in NSC media and added to cells in 100 μl NSC media for a total volume of 200 μl at specified concentrations. After 48 and 72 h of drug treatment, plates were analyzed using CellTiter-Glo® Luminescent Cell viability Assay (CTG, Promega). In brief: CTG reagent was reconstituted according to the manufacturer's instructions. The reagent was then diluted 1:5 in PBS. The 96-well plates were equilibrated to room temperature and existing NSC media with drugs was removed before 100 μl of diluted CTG reagent was added to each well. The cells in the plates were then lysed for 2 min with shaking, followed by a 10 min incubation at room temperature. 90 μl of the cell lysate in each well was transferred to opaque 96-well plates for detection. The emitted ATP-driven luminescence signal was detected using the Synergy 2 instrument (BioTek) and the Software Gen5. Integration time was set at 1 s and sensitivity to 135.

RCAS-TrkB.T1

Flag-tagged TrkB.T1 and Flag-tagged TrkB.FL DNA were cut from pEFBOS vectors (Haapasalo, A. et al. Expression of the naturally occurring truncated trkB neurotrophin receptor induces outgrowth of filopodia and processes in neuroblastoma cells. *Oncogene* 18, 1285-1296 (1999))), visualized on a 1% agarose gel and extracted via QIAquick gel extraction kit (Qiagen), and ligated into modified RCAS (replication-competent avian sarcoma-leukosis virus (ASLV) long-terminal repeat with splice acceptor) vectors (Dunn, K. J., et al. Neural crest-directed gene transfer demonstrates Wnt1 role in melanocyte expansion and differentiation during mouse development. *Proc. Natl Acad. Sci. USA* 97, 10050-10055 (2000)). Appropriate inserts were confirmed by sequencing at Fred Hutch Genomics Core. RCAS virus was produced in DF-1 packaging cells with minor modification (Holland, E. C. et al. Combined activation of Ras and Akt in neural progenitors induces glioblastoma formation in mice. *Nat. Genet.* 25, 55-57 (2000); Holland, E. C. & Varmus, H. E. Basic fibroblast growth factor induces cell migration and proliferation after glia-specific gene transfer in mice. *Proc. Natl Acad. Sci. USA* 95, 1218-1223 (1998)). In brief, DF-1s (ATCC) were maintained in Dulbecco's Modified Eagle Media (DMEM) with 1% penicillin/streptomycin and 10% fetal bovine serum (Paa Laboratories) at 39° C., were transfected with RCAS-TrkB.T1 using X-tremeGENE9 (Roche)+Opti-MEM and passaged three times at high confluency to enhance viral propagation. Expression for TrkB.T1 was confirmed by western blot after three passages while TrkB.FL was at maximum size limitations for RCAS and did not make TrkB.T1 protein.

Generation of Murine Tumors

The RCAS/tv-a system was used for murine tumor modeling in immunocompetent mice (Holland, E. C. et al., *Nat. Genet.* 25, 55-57 (2000)). In brief, DF-1 cells were transfected with the relevant RCAS viral plasmids (RCAS-PDGFB or RCAS-TrkB.T1) using Extreme-Gene 9Transfection reagent (Roche) accordingly to manufacturer's protocol. The cells were maintained for three passages to ensure viral propagation to all cells. After confirmation of RCAS-inserts by western blot, DF1s (passage 4 or later) were used for injection into murine brain. Newborn Nestin (N)/tv-a(agouti) pups (P0-P1; males and females) were injected intracranially (Hamilton syringe #84877) with 1 μL of approximately $1 \times 10^5$ DF-1 cells infected with and producing relevant RCAS viruses suspended in serum-free DMEM (RCAS-TrkB.T1 and RCAS-PDGFB). Simultaneous delivery of two RCAS viruses was performed by the injection of 1 μL of $\sim 2 \times 10^5$ DF-1 cells mixed with equal ratio. Mice were monitored for weeks or months to check for tumor related symptoms such as palpable masses, lethargy, weight loss, seizure, hyperactivity, altered gait, poor grooming, macrocephaly, paralysis. Mice with severe hydrocephalus presumably due to injection trauma or an inflammatory response against the DF-1 cells were excluded from survival analysis in this study. All animal experiments were approved by and conducted in accordance with the Institutional Animal Care and Use Committee of Fred Hutchinson Cancer Research Center (protocol #50842).

3T3-Tva Cells

Stable NIH-3T3 cells expressing Tv-a receptor (Ozawa, T. et al. Most human non-GCIMP glioblastoma subtypes evolve from a common proneural-like precursor glioma. *Cancer Cell* 26, 288-300 (2014)) were subjected to retroviral infection with RCAS-TrkB.T1 via 3×8 h cycles using sterile filtered, viral-containing supernatant from DF-1 cells supplemented with 8 μg/ml polybrene (Sigma) and later selected with 2.5 μg/ml puromycin (GIBCO). 3T3/tv-a cells were maintained for three passages prior to any experiments and cultured in DMEM containing penicillin/streptomycin and 10% fetal calf serum (FCS; newborn calf serum filtered, heat-inactivated ThermoScientific). Prior to PDGF treatment, 3T3-tva cells were serum-starved for 24 h. Recombinant human PDGF-BB (Peprotech, catalog #1001-14B, lot #071504) was diluted in fresh serum-free DMEM and added for various time points before cells were lysed on ice in RIPA extraction buffer (Pierce™ RIPA Lysis and Extraction Buffer containing HALT™ Protease and Phosphatase Inhibitor Cocktail; ThermoScientific™) after being rinsed twice with Dulbecco's phosphate buffered saline (DPBS) (Gibco, —Ca2+ and —Mg$^{2+}$). Extracts were further lysed by mechanical disruption using 18½ gauge needles, rotated at 4° C. for 20 min to ensure lysis, and clarified by centrifugation (16,000×g for 10 min at 4° C.). Proteins were resolved by SDS/PAGE (NuPAGE 10% Bis/Tris; LifeTech) according to XCell Sure Lock™ Mini-Cell guidelines, blocked with 5% milk/TBST and probed with specified antibodies overnight at 4° C. in 5% BSA/TBST. After three TBST rinses, species-specific secondary antibodies were added in 5% milk/TBST at 1:10,000. Blots were rinsed three times with TBST before being developed with Amersham™ ECL™ Western Blotting Detection Reagents (GE Healthcare). For densitometric analyses, immunoreactive bands were scanned and quantitated using National Institutes of Health ImageJ (Scion).

Antibodies

For TrkB.T1 IHC, the generated mouse TrkB.T1 antibody was used (1.3 mg/ml) at 1:20 and recombinant rabbit fusion SPEH1 D12 (11.5 mg/ml) was used at 1:500 and TrkB kinase antibody (abcam #ab18987; lot: GR3280550-2) at 1:250. For western blot analyses of human brain, mouse brain, and 3T3-Tv-a cells, commercial antibodies were used according to manufacturer specifications and bands were confirmed by size using Spectra™ Multicolor Broad Range Protein Ladder (ThermoScientific™ catalog #26634; lot: 00784968): pSTAT3 (Tyr705, Cell Signaling #9145; lot: 22 at 1:1000), pAkt (Ser473, Cell Signaling #4060; lot: 23 at 1:1000), pERK (Cell Signaling phospho-p44/42 MAPK (ERK1/2) (Thr202/Tyr204) (D13.14.4E) XP® #4370; lot: 12 at 1:2000), β-actin (Sigma #AB1978 Clone AC-15; lot: 021M4821 at 1:10,000), pS6 ribosomal protein (Ser235/236, Cell Signaling #4858; lot: 16 at 1:1000), TrkB (Millipore #07-225; lot: 2187222 and lot: 3277578 @ 1:3000), TrkB (abcam #ab33655; lot: GR266297-1 at 1:1000), TrkB (Abcam #ab18987; lot: GR3280550-2 at 1:2000), pPDGFR (3 (Y1021; Abcam #ab62437; lot: GR38791-13 at 1:200), PDGFR 13 (Cell Signaling #3169; lot: 13 at 1:800), ERBB3 (Cell Signaling #12708; lot: 4 at 1:1000), NRG2 (Abcam #ab220615; lot: GR3181158-4 at 1:200), vinculin (Sigma-Aldrich, Cat. V9131; lot: 118M4777V at 1:10.000) and added in 5% BSA/TBST overnight at 4° C.

Primary Nestin/Tv-a Neurospheres

Neural progenitors were isolated from Nestin(N)/tv-apups at P0. A minimum of four P0 N/tv-a WT pups were used. SVZ/Hippocampal-centric region was dissected and placed immediately in 3 ml of accutase warmed to 37° C. Cells were pipetted 30 times for mechanical dissociations and left in a 37° C. water bath with occasional agitation before being pipetted an additional 30 times with a P1000 to create a single cell suspension. Two additional mLs of NSC media were added, cells centrifuged @ 200×g for 3 min at 4° C. Supernatant was removed and pellet was resuspended in 5 ml NSC media, transferred to a new tube (leaving any debris behind) and seeded 100 μL into 4 ml NSC media in 25 cm$^2$ flask. 50 ml fresh NSC media were made each day: 50 ml NSC media consisted of (45 ml Neurocult Mouse Basal media, 5 ml Neurocult Proliferation Supplement (mouse), 50 μL EGF (20 μg/ml stock), 50 μL bFGF (10 μg/ml stock), 125 μL Heparin (Stem Cell Technologies #07980), 500 μL P/S). Fresh growth factors were added every three days. Neural progenitors were passaged twice prior to the start of experiments. For retroviral infection of murine neurospheres with RCAS-TrkB.T1 or RCAS-GFP, RCAS virus was produced in DF-1 packaging cells maintained with serum-free neurosphere medium and was then diluted 1:1 with collection media (fresh murine neurosphere media). Efficiency of retroviral infection was confirmed via western blot after one passage and images were obtained in Fred Hutch Imaging Core.

Data Availability

RNASeq data that support the findings of this study have been deposited in GEO database under the accession code GSE136868. Bulk gene expression data for Mouse tumorspheres was obtained from GSE110700. Bulk gene expression data for cell line 448, 559, G14, and G179 was obtained from GEO repository, GSE89623. Bulk gene expression counts for 44 Human GSCs was obtained from GSE119834. Bulk gene expression counts for six additional Human GSCs (BTSC349, BTSC349, h543, h516, h561 and h676) was obtained from GSE150653. RNA-seq data for human normal brain samples were downloaded from the GTEx data portal (v6) [gtexportal.org/]. RNA-seq data for TCGA-GBM and TCGA-LGG were downloaded from the UCSC Xena/ Toil hub [xenabrowser.net/datapages/?hub=https://tcga.x-enahubs.net:443]. Transcript data for TCGA-GBM and TCGA-LGG were downloaded from Broad's firebrowse [firebrowse.org/?cohort=GBM&download dialog=true]. All other relevant data are available from the corresponding author on request. The data that support the findings of this study are included with the manuscript and supplementary data files and also available from the corresponding author upon reasonable request.

Code Availability

All custom scripts have been made available at github-.com/sonali-bioc/Pattwelletal2020. All analyses were performed using publicly available software (R and R/Bioconductor packages) as indicated in Materials and Methods.

Example 2

This Example describes additional investigations that expand on the investigation described in Example 1, demonstrating that a kinase-deficient NTRK2 splice variant, TrkB.T1, is the predominant NTRK2 isoform in a wide range of adult and pediatric tumors. These investigations demonstrate the utility of the NTRK2 isoform as a powerful marker for a diverse spectrum of cancer types and, considering the causal role of the NTRK2 isoform in the cancers, a powerful target for cancer therapy.

Temporally-regulated alternative splicing choices are vital for proper development, yet the wrong splice choice may be detrimental. This investigation highlights a novel role for the neurotrophin receptor splice variant TrkB.T1 in neurodevelopment, embryogenesis, transformation, and oncogenesis across multiple tumor types in both humans and mice. TrkB.T1 is the predominant NTRK2 isoform across embryonic organogenesis and is highly expressed in a wide range of adult and pediatric tumors. Further, forced expression of TrkB.T1 causes multiple solid and nonsolid tumors in mice in the context of tumor suppressor loss. These results highlight a unique role for the neurotrophin receptor splicing in development and oncogenesis and underscore the need for considering alternative splicing and transcript level data in neuroscience, developmental biology, and oncology research.

Introduction

Embryogenesis, and neurodevelopment in particular, comprise an elegant and well-orchestrated series of tightly regulated events, culminating in an organized and highly functioning organism. Cancer, on the other hand, can often be viewed as an uncontrolled, unrestrained, genetically chaotic disease, lacking the precise spatial and temporal rigidity associated with normal development. While appearing to be on opposite sides of the organizational spectrum, the similarities between early development and oncogenesis are numerous. This has been observed frequently as key developmental signaling pathways, such as Wnt, Hedgehog, or Notch, have been shown to be dysregulated in cancer, across all stages from tumor initiation and maintenance, to metastasis.

Encoded by the NTRK2 gene, the tropomyosin receptor kinase TrkB, which has many alternatively spliced isoforms, has well-established roles across neurodevelopment, astrocyte biology, and has also been implicated in a wide range of cancer types. NTRK2 gene fusions have recently been the focus of many clinical and pharmacological studies while inhibition of the TrkB kinase has been shown to inhibit cell proliferation and contribute to apoptosis. In addition to well-known roles in neurobiology, recent studies suggest that NTRK2 may render cells resistant to anoikis and prone to metastasis while others suggest its involvement in the epithelial-to-mesenchymal transition associated with increased migration and invasiveness of many cancer cell lines, yet the precise mechanisms are not fully known. While prior studies have been fundamental in uncovering NTRK2 involvement in cancer, the complex post-translational modifications, intricate splicing patterns, and prior roles in embryogenesis are often ignored. Among the alternatively spliced isoforms of TrkB is a kinase-deficient, truncated isoform TrkB.T1.

In this study, the role of the kinase-deficient NTRK2 splice variant, TrkB.T1, is characterized in embryonic neurodevelopment and early organogenesis via transcript analysis of sci-RNA-seq3 data of E9.5 to E13.5 mouse embryos and transcript specific immunohistochemistry. A developmental role for TrkB.T1 is demonstrated beyond that of the central nervous system, highlighting TrkB.T1's transformation potential in vitro, and uncovering its role in oncogenesis in vivo using a RCAS/tv-a mouse model. It is further revealed that TrkB.T1 is the predominant TRK isoform expressed across the majority of adult and pediatric tumors using clinical data from The Cancer Genome Atlas (TCGA) and Therapeutically Applicable Research to Generate Effective Treatments (TARGET), respectively, demonstrating its varied expression across several tumor types. From alterations in splicing factors to changes in gene expression, the discovery of isoform specific oncogenes with embryonic ancestry has the potential to shape the way we think about developmental systems and oncology.

Results

TrkB.T1 in Embryonic Development and Organogenesis

The investigation described in Example demonstrates that a kinase-deficient NTRK2 splice variant, TrkB.T1, is the predominant neurotrophin receptor in human gliomas, enhances glioma aggressiveness in mice, and increases the perdurance of PDGF-induced Akt and STAT3 signaling. This splice variant is not the result of a pure truncation, as in addition to loss of the terminal kinase exons, it contains a unique terminal exon encoding a 11-amino acid tail that is 100% conserved across species including chicks, mice, rats, felines, and humans, suggesting a potentially evolutionarily significant biological role. In light of recent findings implicating the kinase-deficient splice variant in glioma biology (see Example 1), this Example explores the role of TrkB.T1 in neural development and early embryonic central nervous system (CNS) development in particular. Furthermore, the role of developmentally regulated splicing choices is investigated, leading to the demonstration that forced expression of a splice variant that does not belong at a particular developmental stage can lead to neoplasia in the same organs that once expressed it during embryogenesis.

It is widely known that the majority of organ development in rodents occurs prior to E18. Previous studies have observed that TrkB.FL is the predominate isoform during early rat forebrain development while TrkB.T1 predominates in forebrain regions during late postnatal development and adulthood, yet protein analysis for these studies focused on E18 for embryonic staging and P0-P30 for postnatal development. Recently, advances in next generation sequencing have allowed for the characterization of transcriptional dynamics across development at a single cell resolution resulting in a Mouse Organogenesis Cell Atlas (MOCA) (Cao, J., et al. (2019). The single-cell transcriptional landscape of mammalian organogenesis. *Nature* 566, 496-502, incorporated herein by reference in its entirety). To explore the expression of TrkB.T1 in CNS development, the fact that the truncated and full-length transcripts differ in their 3' ends was utilized, which allows for transcript quantification in single cell RNA sequencing data and mapped expression of TrkB.T1 and TrkB.FL transcripts in mouse embryos over developmental time. Using sci-RNA-seq3 data, MOCA provides gene expression data and cell trajectory annotation for 2,026,641 cells from 61 mouse embryos across five development stages (E9.5-E.13.5), resulting in 38 main cell clusters and 10 main trajectories. The expression of transcripts for all protein coding genes, including TrkB.T1 and TrkB.FL, were normalized and visualized over the existing landscape provided by Cao et al., supra. First, TrkB.FL expression patterns in the t-SNE plot of all 38 cell types within the MOCA were assessed and it was found that TrkB.FL expression is appreciably restricted to a subset of cell types, all of which were neuronal in nature (e.g., inhibitory neurons, sensory neurons, excitatory neurons, and inhibitory neuron progenitors, post-mitotic premature neurons; not shown). TrkB.T1, however, was expressed broadly across many different cell types within the embryo during this period (not shown). The next step was to explore the NTRK2 transcript expression patters within the CNS developmental trajectory. TrkB.T1 cellular expression was observed across multiple neurodevelopmentally driven cell clusters including radial glia, immature oligodendrocytes, isthmic organizer cells (not shown). The second largest population of cells with high, variable levels of TrkB.T1 expression during this developmental period is found in the mesenchymal trajectory, and mapping expression of both transcripts showed a vast predominance of TrkB.T1 over TrkB.FL similar to the non-neuronal cell types of the developing CNS (not shown). Visualization of NTRK2 expression reveals intense, diffuse expression of TrkB.T1 across multiple days in multiple cell types, with expression levels rivaling those of actin in particular clusters (not shown), whereas TrkB.FL expression remains predominantly restricted to mature neurons (not shown). An interactive site allowing 3D visualization and further exploration of NTRK2 transcripts among cell types and within the CNS and mesenchymal trajectories over time can be found at atlas.fredhutch.org/fredhutch/ntrk2/.

As the sci-RNA-seq3 data show widespread TrkB.T1 expression across multiple clusters within and outside the CNS, the next step was to visualize TrkB.T1 and TrkB.FL expression across embryonic development beyond E13.5. To this end, histological sections of embryos from E10-E17 were stained with antibodies specific to the TrkB.FL kinase domain as well as an antibody specific to the intracellular 11-amino acid tail of TrkB.T1 (see Example 1). Similar to the sci-RNA-seq3 data, examination at early embryonic time points, when the most rapid cellular growth and organogenesis is underway, the ratio between these receptors is different, with TrkB.T1 present at exceedingly high levels in multiple organ sites (not shown), compared to TrkB.FL (not shown), which is predominantly expressed and maintained in CNS consistent with the transcript levels for the two TrkB gene products described above. By the end of embryonic development circa E17, TrkB.T1 levels have decreased but are still present throughout various non-CNS organs, while the majority of TrkB.FL remains within the CNS. These data suggest that in addition to a role in CNS development and gliomagenesis, TrkB.T1 may have a role in early organogenesis, implying the possibility that it may play a role in multiple cancer types outside the CNS.

TrkB.T1 Transforms 3T3 Cells in Colony Formation Assay

Figure 7A:
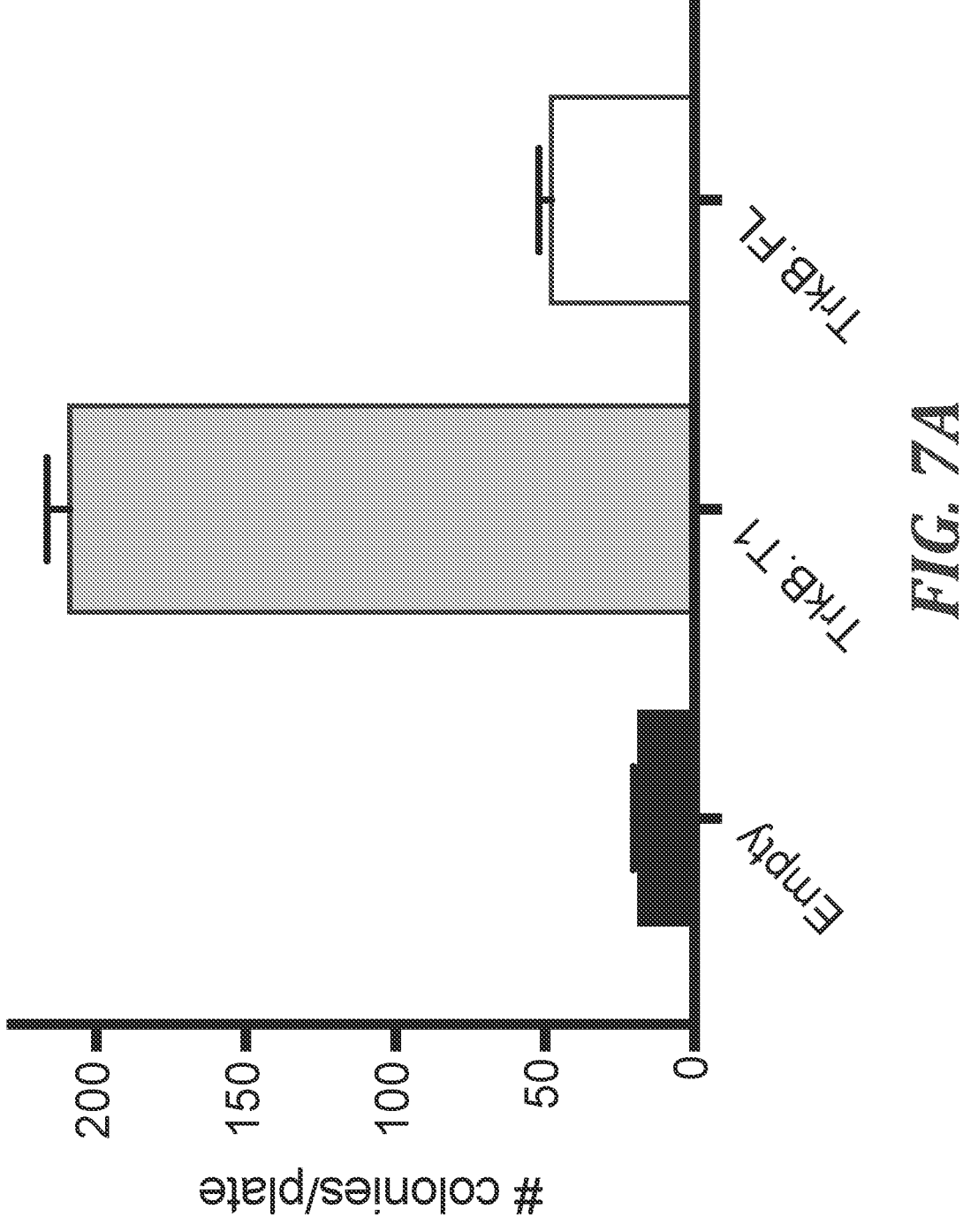
FIGS. 7A-7F illustrate that TrkB.T1 transforms 3T3 cells and causes solid and non-solid tumors throughout the body in mice when overexpressed in the context of tumor suppressor loss.
Figure 7B:
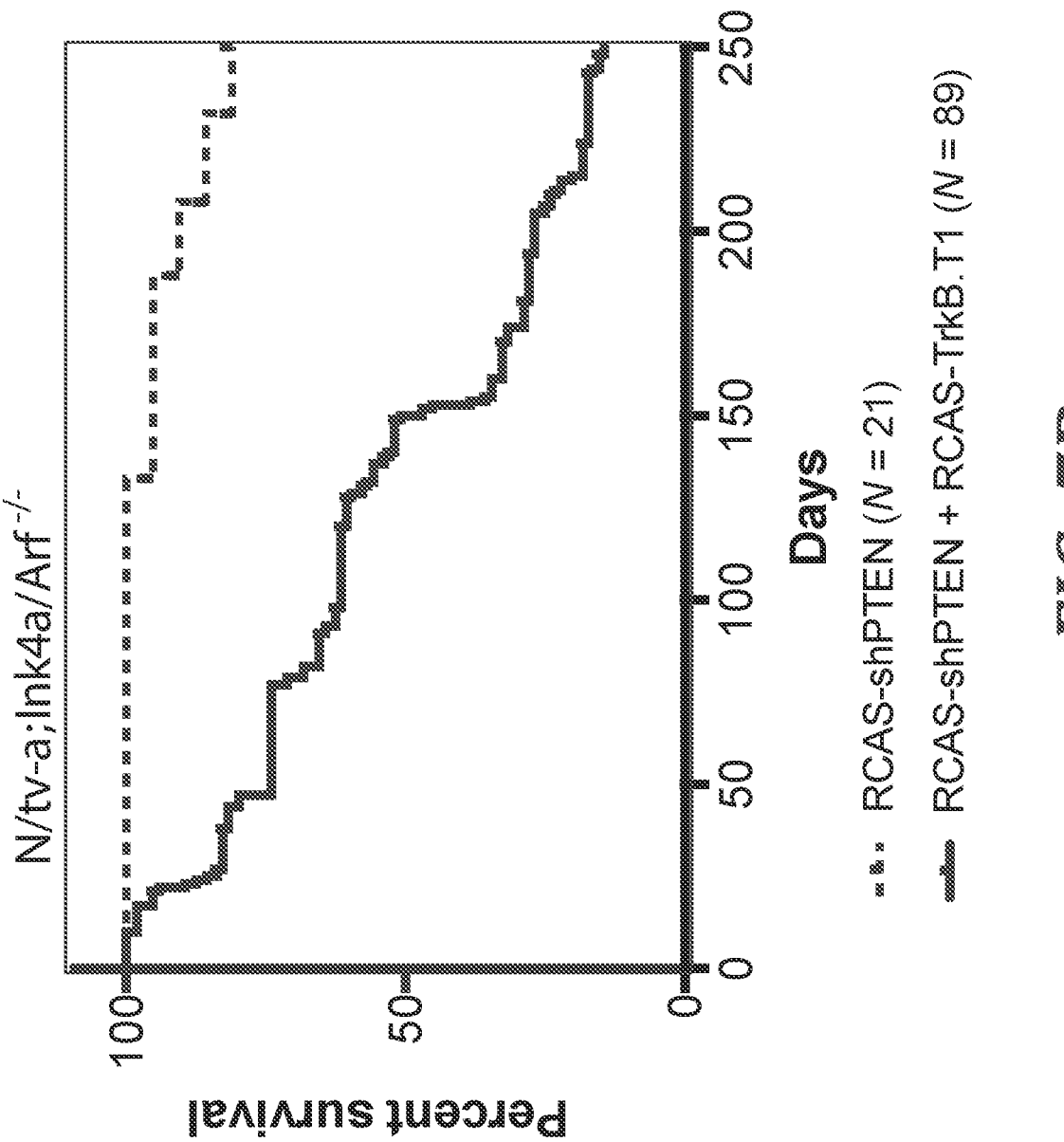
Figure 7C:
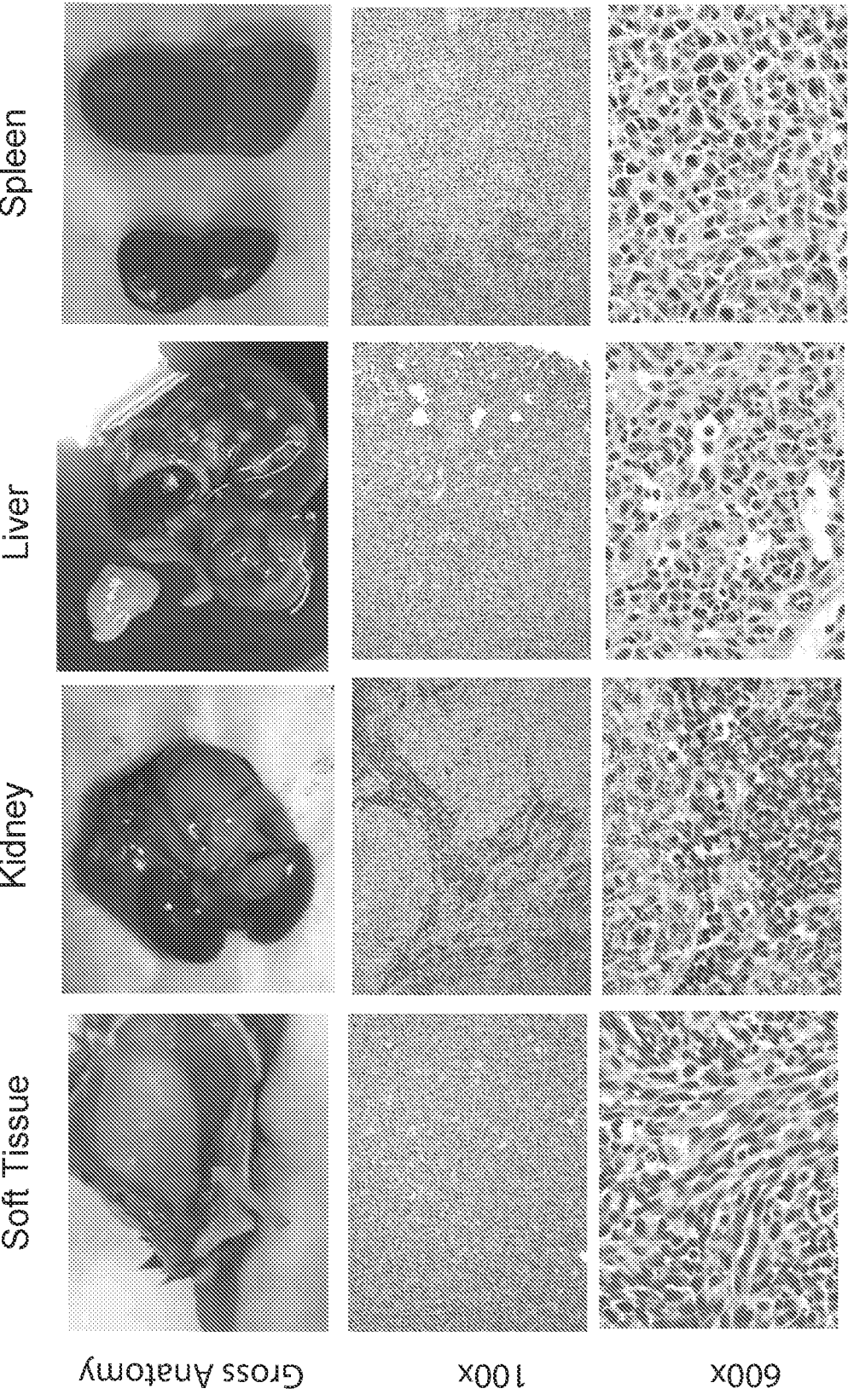
Figure 7D:
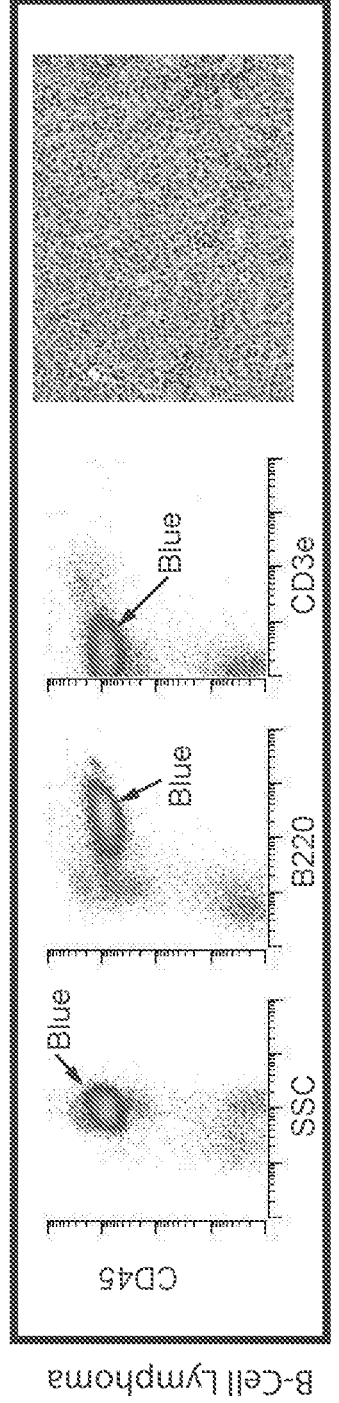
Figure 7E:
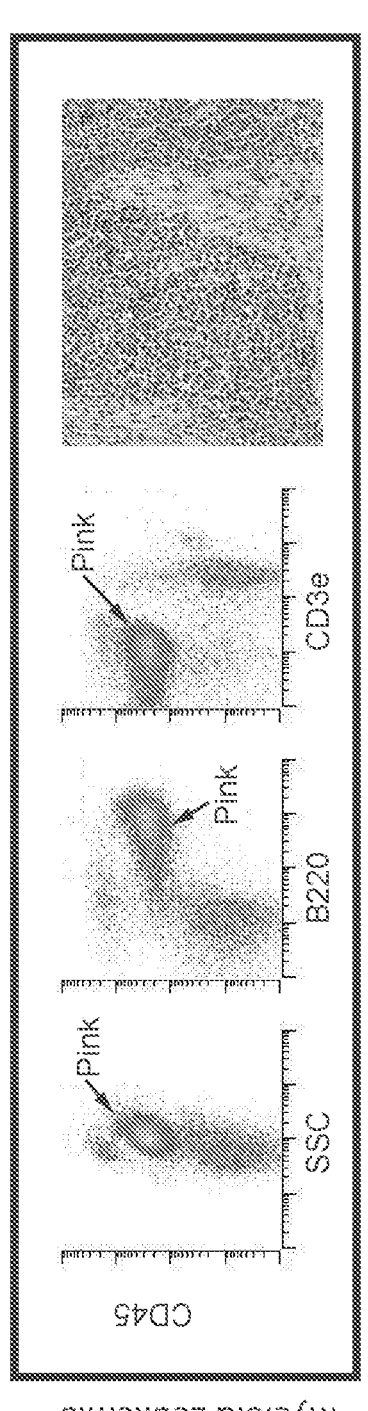
Figure 7F:
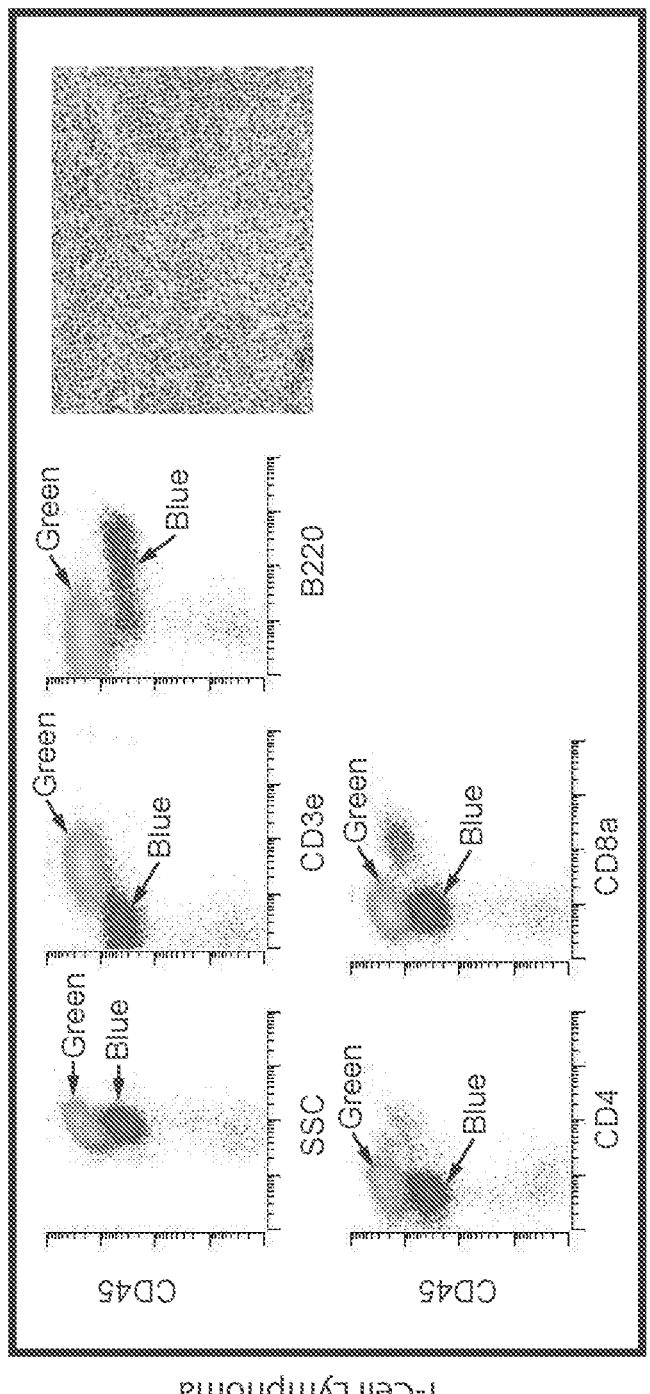

Given the widespread distribution of TrkB.T1 in multiple organ sites and cell types across embryonic development, and the findings in Example 1 that the TrkB.T1 splice variant predominates over the full-length kinase containing TrkB variant, TrkB.FL, in gliomas and that this TrkB.T1 gene product enhances PDGF-driven glioma aggressiveness in vivo and amplifies PDGF-driven AKT and Stat signaling in vitro, the next step was to compare the relative transformation potential of the kinase-containing TrkB.FL and kinase-deficient TrkB.T1 isoforms using a soft agar colony formation assay. Forced expression of the TrkB.T1 splice variant containing the 11-amino acid intracellular tail in 3T3 cells led to significantly enhanced colony formation (average colonies=209) compared to overexpression of the kinase-containing variant, TrkB.FL (average colonies=48), or control vector (average colonies=19.33) (F $(2,6)$=401.5, $p<0.0001$) (FIG. 7A).

TrkB.T1 Causes Multiple Cancer Types in Mice

TrkB.T1 is expressed at moderate levels in multiple cell types within the normal postnatal brain, and as such, is not expected to be oncogenic on its own in a context where endogenous expression and function is likely tightly regulated. Prior investigation into TrkB.T1's role in gliomas revealed that a multitude of genes in PI3K/Akt/PIP/inositol phosphate pathways were significantly positively correlated with NTRK2 expression in LGG and GBM compared to normal brain via Differential Gene Correlation Analysis (DCGA) suggesting a role for TrkB.T1 in the PI3K signaling pathway. Based on these results and the above developmental and transformation data, the next step was to explore whether TrkB.T1 is capable of inducing tumor aggressiveness within and outside the CNS in the context of tumor suppressor loss. Mice with CDKN2A (Ink4a/Arf) loss and PTEN loss were selected to explore in a sensitized genetic background as TrkB.T1 overexpression does not cause tumors on its own in wild-type mice, while Pten is a negative regulator of Akt signaling and Ink4a/Arf loss is a frequent event in cancer. To answer this question, the RCAS/TV-A system was used, which allows for somatic expression of a gene of interest in particular cell types, to force overexpression TrkB.T1 and knockdown PTEN expression in nestin positive progenitor cells. N/tv-a;Ink4a/Arf$^{-/-}$ mice were injected intracranially with RCAS-TrkB.T1 and RCAS-shPTEN at postnatal day (P)0-1. Histological examination of N/tv-a;Ink4a/Arf$^{-/-}$ mouse brains injected with the combination of RCAS-TrkB.T1 and RCAS-shPTEN showed no tumors within the time course of this experiment. Consistent with previously published work, TrkB.T1 does not cause brain tumors on its own but rather it enhances PDGF-driven tumors. RCAS-TrkB.T1 and RCAS-shPTEN injections were insufficient to generate tumors within the brain of N/tv-a;Ink4a/Arf$^{-/-}$ mice, however the intent was to address whether this combination was oncogenic in contexts outside the central nervous system, where endogenous levels of TrkB.T1 in the adult mouse are present at much lower levels than in normal brain.

Mis-expression of factors or proteins that are benign or necessary in one cell type may lead to aberrant and non-canonical signaling in another cell type, as has been shown for Wnt signaling. Because nestin is expressed in a wide range of stem and progenitor cells during the development of various organ sites (not just neural and glial progenitors), this promoter was chosen to target RCAS delivery specifically to nestin positive cells. N/tv-a;Ink4a/Arf$^{-/-}$ mice were injected intraperitoneally (i.p.) or intramuscularly (i.m.) with RCAS-TrkB.T1 and RCAS-shPTEN. While neither RCAS-shPTEN nor RCAS-TrkB.T1 alone caused cancer in this genetic background during the time course of this experiment, the combination of RCAS-shPTEN and RCAS-TrkB.T1 injections caused a range of solid and non-solid tumors originating from nestin-positive cells outside of the central nervous system (CNS). These included soft tissue sarcomas, carcinomas arising in the kidney and lymphoid leukemias and lymphomas (FIGS. 7C-7F). Immunohistochemistry on these solid tumors confirmed that these tumors throughout the body had both high levels of TrkB.T1 and loss of PTEN expression (not shown). These data suggest that the threshold for combined TrkB.T1 and PTEN loss to generate tumors may be lower in non-CNS nestin-positive cells than those within the brain where TrkB.T1 is already present at moderate basal levels and that overexpression of TrkB.T1 in combination with PTEN loss has the potential to form tumors in the same organ sites for which TrkB.T1 was expressed embryonically.

Figure 10:
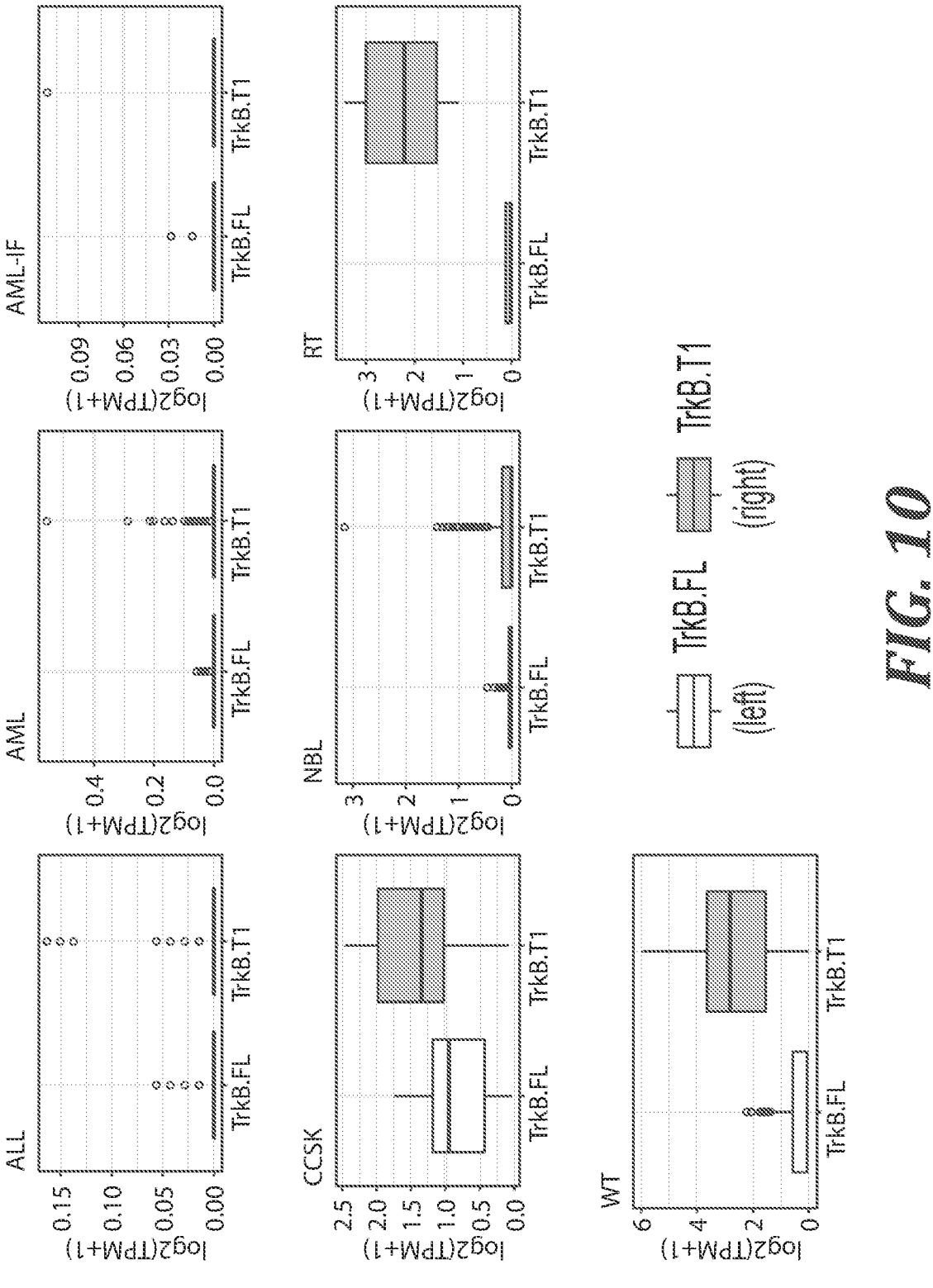
FIG. 10 illustrates NTRK2 transcript analysis of pediatric data from the Therapeutically Applicable Research to Generate Effective Treatments (TARGET) program. These data show that, similar to adult tumors in TCGA (as presented in FIGS. 9A-9F), TrkB.T1 expression is the predominant isoform compared to TrkB.FL in several cancer types. Acute lymphocytic leukemia (ALL), acute myeloid leukemia (AML), induction failure AML (IF-AML), clear cell sarcoma of the kidney (CCSK), neuroblastoma (NBL), rhabdoid tumor (RT) and Wilms tumor (WT). Data are represented as boxplots where the middle line is the median, the lower and upper hinges correspond to the first and third quartiles (the 25th and 75th percentiles), the upper whisker extends from the hinge to the largest value no further than 1.5*IQR from the hinge (where IQR is the inter-quartile range, or distance between the first and third quartiles) and the lower whisker extends from the hinge to the smallest value at most 1.5*IQR of the hinge while data beyond the end of the whiskers are outlying points that are plotted Individually.

TrkB.T1 is the Predominantly Expressed Form of TrkB RNA and Protein in Adult and Pediatric Tumors The large number and breadth of tumor types induced by TrkB.T1 expression combined with the knowledge that in gliomas the predominant form of TrkB is the T1 splice variant prompted an in-depth pan-cancer analysis of NTRK2 transcript expression across all organ sites within The Cancer Genome Atlas (TCGA). Similar to what was reported for gliomas (see above), expression of the full-length, kinase containing TrkB.FL is minimal to absent across the majority of tumor types within TCGA, while TrkB.T1 expression is consistently high (FIGS. 9A-9F). In addition to the data from TCGA, which is comprised of mostly adult tumors, previous studies have also shown a potential role for TrkB in pediatric tumors. TrkB gene products have been shown to be expressed at high levels in high-risk neuroblastoma (NBL) and correlated with poor prognosis while levels of TrkB gene products have been shown to be correlated with unfavorable outcome in Wilms tumor (WT) patients. Transcript specific analysis of pediatric data from the Therapeutically Applicable Research to Generate Effective Treatments (TARGET) program confirms that, similar to adult tumors in TCGA, TrkB.T1 expression is the predominant isoform compared to TrkB.FL in several cancer types, including Wilms tumor (WT), rhabdoid tumor (RT), neuroblastoma (NBL), and clear cell sarcoma of the kidney (CCSK) (FIG. 10).

To extend upon these transcript results demonstrating predominant TrkB.T1 expression across a wide range of human tumors, it was next determined how well RNA transcripts correlate with TrkB.T1 protein distribution. Immunohistochemistry on a tissue microarray containing a wide assortment of human tumor types (FIGS. 9A-9F) reveals variable, increased TrkB.T1 expression and distribution, with high TrkB.T1 H-score values (not shown) for nearly all tumor types. These results show that both RNA transcript expression and protein levels for TrkB.T1 are high across all tumor types in available datasets, suggesting that this is the NTRK2 splicing choice made across cancers and predominates in non-neuronal cells of the embryo as well.

Figure 8:
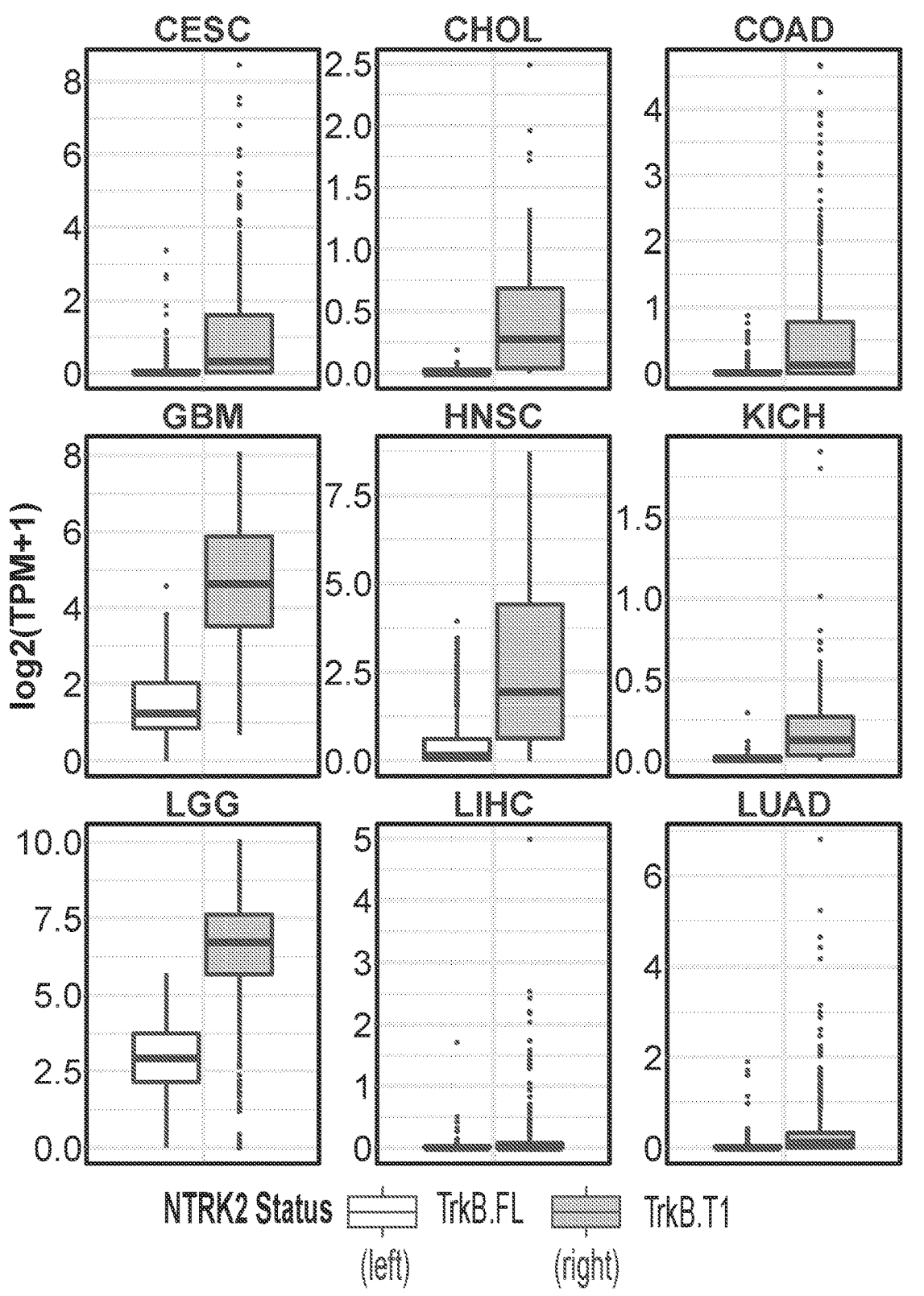
FIG. 8 is a series of graphical representations showing pan-cancer NTRK2 Transcript Analyses. NTRK2 transcript analysis shows minimal to zero expression of TrkB.FL transcript and increased expression for TrkB.T1 transcript across all TCGA organ sites: adrenocortical carcinoma (ACC), bladder urothelial cancer (BLCA), breast invasive carcinoma (BRCA), cervical squamous cell carcinoma and endocervical adenocarcinoma (CESC), cholangiocarcinoma (CHOL), colon adenocarcinoma (COAD), colorectal adenocarcinoma (COAD/READ), lymphoid neoplasm diffuse B-cell lymphoma (DLBC), esophageal carcinoma (ESCA), glioblastoma (GBM), head & neck squamous carcinoma (HNSC), kidney chromophobe (KICH), kidney renal clear cell carcinoma (KIRC), kidney renal papillary cell carcinoma (KIRP), acute myeloid leukemia (LAML), liver hepatocellular carcinoma (LIHC), lung adenocarcinoma (LUAD), lung squamous cell carcinoma (LUSC), mesothelioma (MES), ovarian serous cystadenocarcinoma (OV), pancreatic adenocarcinoma (PAAD), pheochromocytoma and paraganglioma (PCPG), prostate adenocarcinoma (PRAD), rectum adenocarcinoma (READ), sarcoma (SARC), skin cutaneous melanoma (SKCM), stomach adenocarcinoma (STAD), stomach and esophageal (STES), testicular germ cell tumor (TGCT), thyroid carcinoma (THCA), thymoma (THYM), uterine corpus endometrial carcinoma (UCEC), uterine carcinoma (UCS), uveal melanoma (UVM). Data are represented as boxplots where the middle line is the median, the lower and upper hinges correspond to the first and third quartiles (the 25th and 75th percentiles), the upper whisker extends from the hinge to the largest value no further than 1.5*IQR from the hinge (where IQR is the inter-quartile range, or distance between the first and third quartiles) and the lower whisker extends from the hinge to the smallest value at most 1.5*IQR of the hinge while data beyond the end of the whiskers are outlying points that are plotted individually
Figure 8:
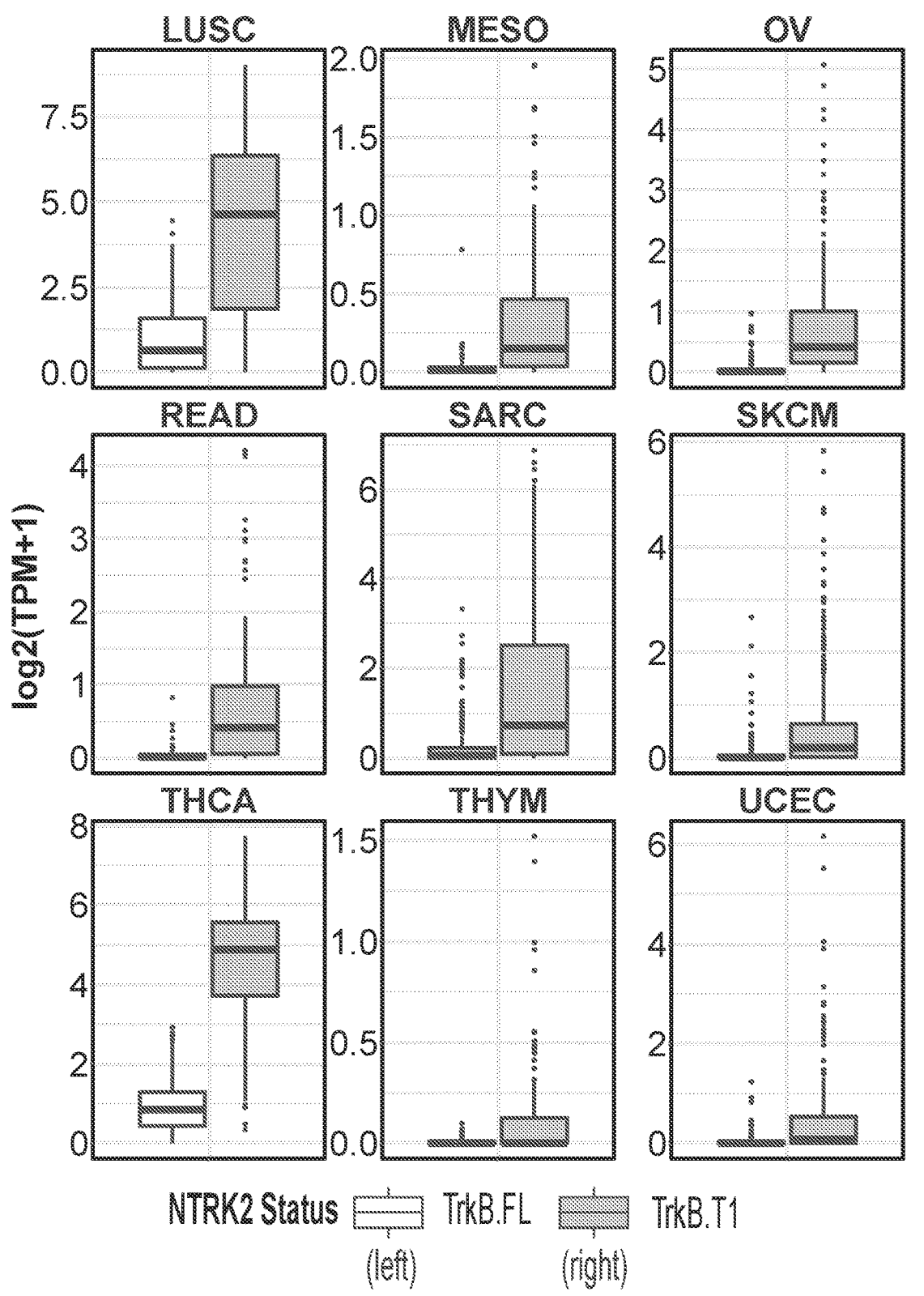
Figure 8:
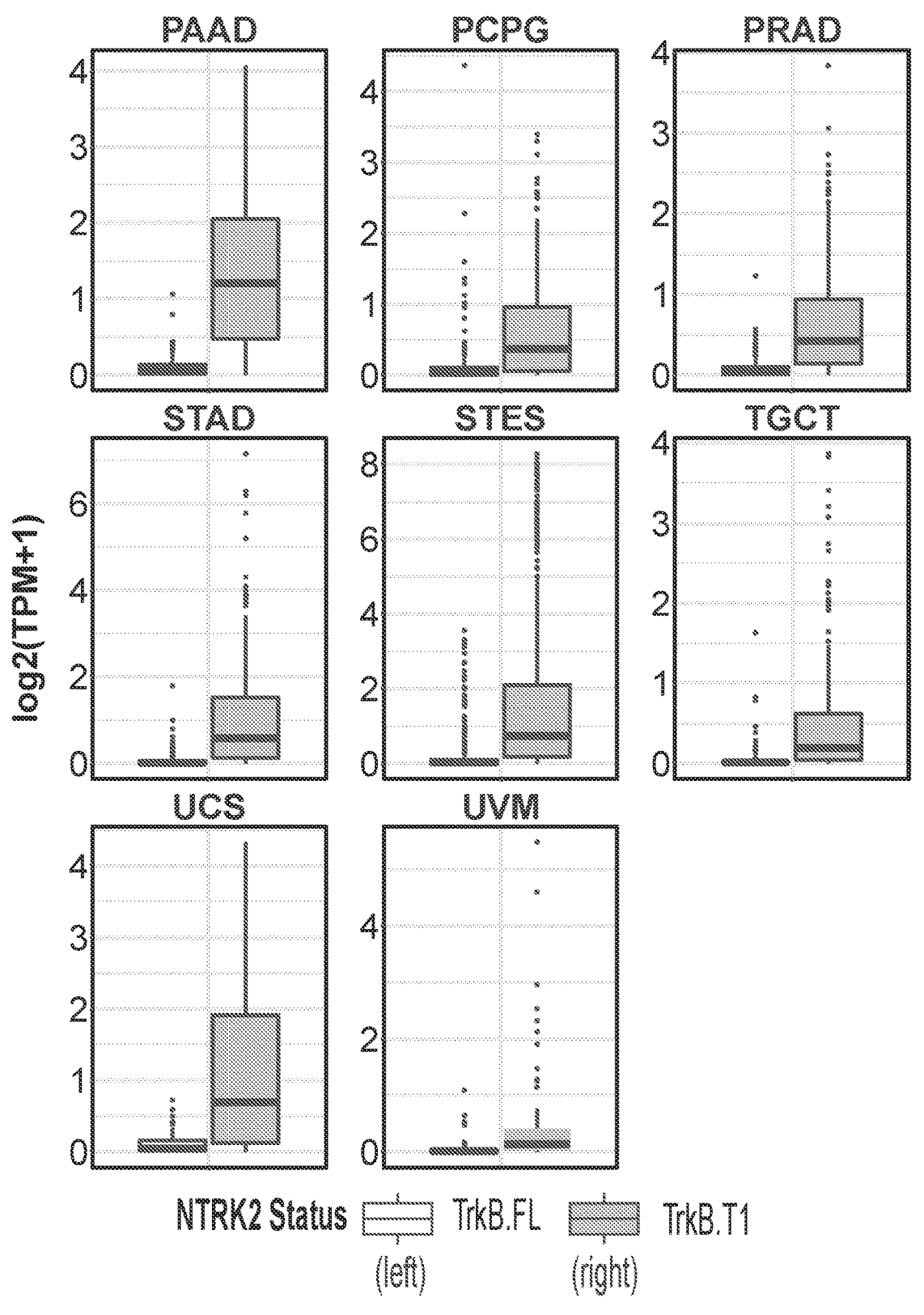
Figures 9A, 9B, 9C, 9D, 9E, 9F:
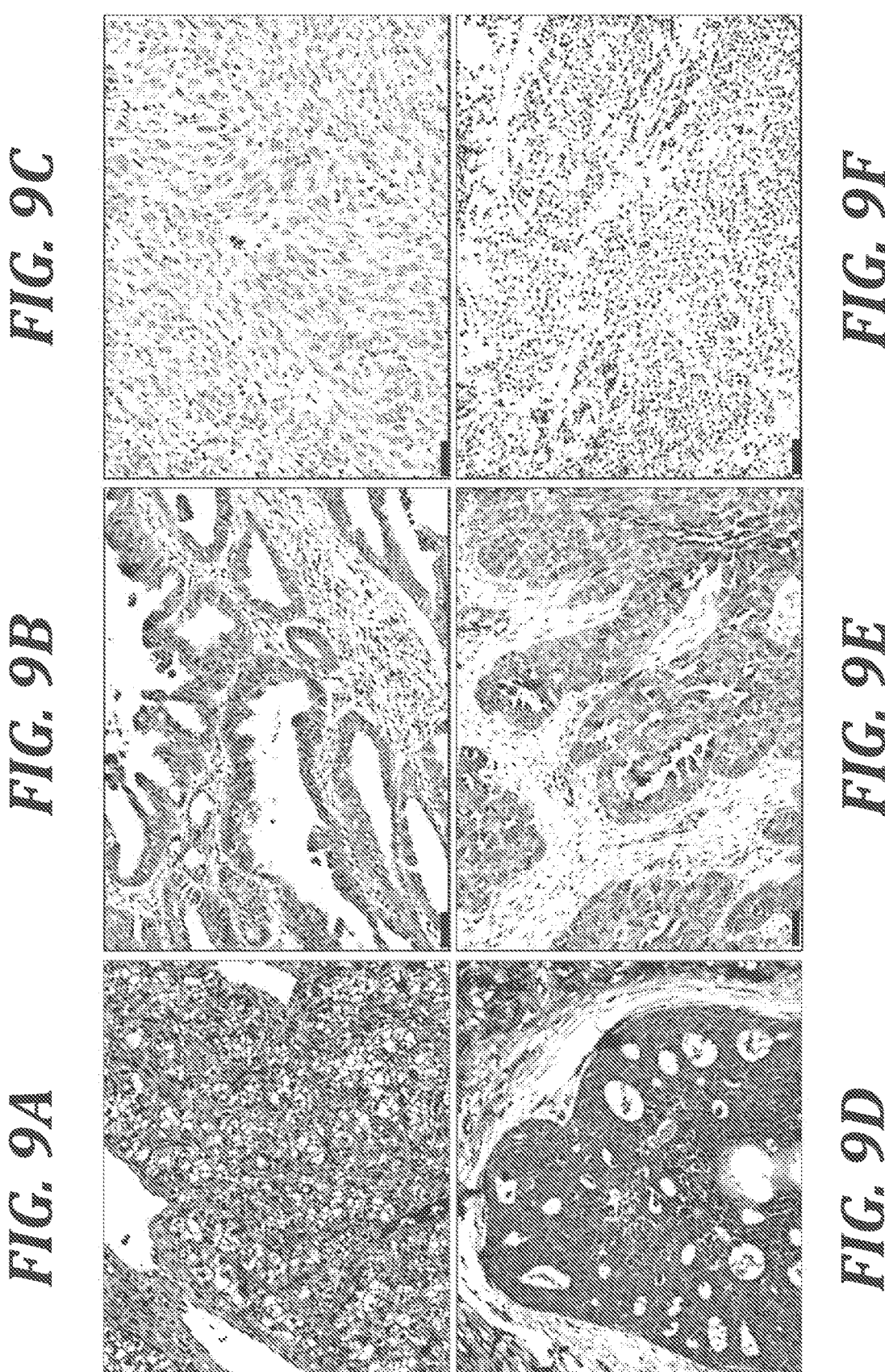
FIGS. 9A-9F are micrographs illustrating that TrkB.T1 has variable expression across multiple human tumor types. Representative micrographs of TrkB.T1 expression in (FIG. 9A) clear cell renal cell carcinoma, (FIG. 9B) colonic adenocarcinoma, (FIG. 9C) leiomyosarcoma, (FIG. 9D) mammary carcinoma (ductal carcinoma in situ is shown here), (FIG. 9E) pancreatic adenocarcinoma, and (FIG. 9F) seminoma. Scalebar indicates 100 μm.

Taken together, these data show that TrkB.T1 is the NTRK2 isoform expressed in multiple cell types across embryonic development, is expressed at surprisingly high rates across various adult and pediatric organ sites within TCGA and TARGET (FIGS. 8 and 10) and is capable of transforming cells in vitro and causing tumors across various organ sites in the context of loss of the common tumor suppressors Ink4a/Arf and PTEN in mice (FIGS. 7A-7F). These results demonstrate that a splice variant that is predominantly expressed in development can be causal in the development of multiple cancer types in mice when mis-expressed in conjunction with tumor suppressor loss in the wrong cell type or during the wrong developmental stage.

Discussion

While a host of point mutations have been discovered in cancer, only a small majority of these mutations have been shown to be causal. Complicated splicing choices allow for highly regulated expression of various transcripts in both normal development while mis-expression of the wrong variant at the wrong time may be lethal. Although it is known that aberrant splicing mechanisms exist in cancer and many mis-spliced genes are made in cancer, TrkB.T1 appears to be one candidate whose regulated splicing choice appears in normal organogenesis but whose mis-expression appears as a driver of oncogenesis.

While the embryogenic data offers correlative insight, the causal RCAS/tv-a mouse studies show that TrkB.T1 causes cancer, potentially by trapping cells in an undifferentiated state similar to their early embryogenic stage. In vitro, TrkB.T1 amplifies the signaling downstream of PDGFR, as described above, in the absence of TrkB.FL. In the embryonic single cell data, TrkB.FL and TrkB.T1 are rarely, if ever, expressed in the same cell suggesting that TrkB.T1 does not function through transactivation of TrkB.FL, but potentially through other signaling pathways. Taken together, the broad expression of TrkB.T1 across the embryonic development and high levels in multiple human tumor types suggest that it may work in combination with other receptors to enhance or prolong activation various tyrosine receptor kinases. Ultimately, TrkB.T1 is strongly expressed in embryonic development during highly proliferative states, is widely expressed in human cancers, and gain of function thereof causes cancer in mice. These data highlight the TrkB.T1 splice variant as a promising candidate as a target for processes in development and oncogenesis across a range of organ sites and tumor models.

These observations, combined with the existence of multiple NTRK2 transcripts, suggest that upregulated or constitutively active TrkB kinase activity may not be the sole NTRK2 contribution to cancer. While it has long been known that splicing choices are vital for proper development of normal neural and non-neural tissue, it is becoming widely accepted that aberrant RNA splicing is a common feature across all cancer hallmarks. Future studies investigating the role of NTRK2 splice variants on treatment outcomes and survival across the organ sites highlighted here may be of interest from both a basic science and clinical perspective. The need for future transcript-level investigation at both the bioinformatic and biological level will become increasingly important in order to tease apart highly complex genomic splice regulation in neuroscience, development, and cancer alike. As it is widely known that splicing is aberrant in cancer, it is possible that globally dysregulated splicing may lead to the production of a handful of specific splice variants that contribute to cancer when expressed outside of normal development. Similar to the many observed point mutations in cancer, only a small subset of these point mutations are actually oncogenic. These rare point mutations that are known to directly contribute to oncogenic signaling do so because they lead to the formation of oncogenic products such as Ras and alter pathways that are otherwise tightly regulated in normal tissues. It is known that cancer cells exhibit vast transcriptomic alterations and that cancer specific isoforms are not merely byproducts of abnormal physiology. In cancer, there are many different splice variants, most of which, like point mutations, are not oncogenic drivers. However, if expressed in the wrong place, at the wrong time, some of these splice variants, like TrkB.T1 may contribute to a cancer phenotype. These data highlight TrkB.T1 as a powerful candidate that, when mis-expressed in the absence of tumor suppressors, causes cancer in the same organs where it was expressed embryonically, further strengthening mechanistic links between the tightly regulated splicing patterns of development with the aberrant splicing choices observed in cancer.

While TrkB.T1 may prove to be one such oncogenic isoform of TrkB, the possibility remains that numerous developmentally regulated splice variants exist that promote a cancer phenotype when mis-expressed in specific contexts or cell types, and at various developmental timepoints. Seeking to uncover additional splice variants that are drivers of oncogenesis or contributors to cancer hallmarks and teasing apart the mechanisms by which they do so generates a wide range of research questions. Approaches to studying splicing factors and alternatively spliced transcripts such as those delineated here should not be restricted to particular genes, stages of development, or organ sites and may uncover promising new avenues for diagnostics or therapeutics by revealing additional developmentally regulated, oncogenic splice variants.

Methods

Bioinformatic Analysis

Quantification of Transcript Data from Sci-RNA-Seq3

SAM alignment files for the MOCA dataset were downloaded from shendure-web.gs.washington.edu/content/members/cao1025/public/nobackup/. The "cell annotation.csv" which contained t-SNE coordinates, UMAP coordinates, and information about clusters and trajectories was downloaded from oncoscape.v3.sttrcancer.org/atlas.gs-.washington.edu.mouse.rna/downloads. The "Comprehensive gene annotation" file was downloaded from gencode-genes.org/mouse/release_M12.html. For each of the 2,062,641 cells, the number of strand-specific UMIs was calculated for each cell mapping to transcripts of each gene with the Python v.2.7.13 HTseq (Anders, S., et al. (2015). HTSeq—a Python framework to work with high-throughput sequencing data. *Bioinformatics* 31, 166-169) package using GENCODE vM12 (Harrow, J., et al. (2012). GENCODE: the reference human genome annotation for The ENCODE Project. *Genome Res* 22, 1760-1774). Monocle3 (Trapnell et al., 2014) was used to construct a cell data set object with all the transcript expression data, preprocess_cds( ) was used to normalize the transcript expression. The expression of TrkB.T1 and TrkB.FL were visualized over existing UMAPs and t-SNEs provided by Cao et al using ggplot2 (Wickham, H. (2009). Ggplot2: elegant graphics for data analysis, (New York: Springer)). An interactive website (atlas.fredhutch.org/fredhutch/ntrk2/) has been put together to facilitate further exploration of the NTRK2 transcript data across various trajectories and cell types.

Obtaining & Transforming Transcript Level Data from TCGA

Transcript Data (TCGA RNAseqV2 RSEM data) for TCGA organ sites was downloaded from Broad's Fire-Browse website (gdac.broadinstitute.org/). Transcript data (TPM data) was also downloaded for TARGET from UCSC Xena: (xenabrowser.net/datapages/?dataset=target_RSEM_gene_tpm&host=https %3A %2F %2F toil.xenahubs.net&removeHub=https %3A %2F %2Fxena.treehouse.gi.ucsc.edu %3A443). To make the RSEM data from TCGA, and TPM data comparable, we converted RSEM counts from TCGA to TPM counts using the following formula (Li, B., and Dewey, C. N. (2011). RSEM: accurate transcript quantification from RNA-Seq data with or without a reference genome. *BMC Bioinformatics* 12, 323): RSEM can be multiplied by $10^6$. For transcript analyses, NTRK2 transcript IDs were manually aligned to confirm sequence homology and are as follows: TrkB.FL (UCSC: uc004aoa.1; Ensembl: ENST00000376213.1,NTRK2_201), TrkB.T1 (UCSC:

uc004aob.1; Ensembl: ENST00000395882.1, NTRK2_204). Transcript Data was visualized using boxplots using R package ggplot2 (Wickham, H. (2009). Ggplot2: elegant graphics for data analysis, (New York: Springer)).

Generation of Murine Tumors

The RCAS/tv-a system used in this work has been described previously for murine tumor modeling in immunocompetent mice (see Example 1). DF-1 cells were transfected with the relevant RCAS viral plasmids using Extreme-Gene 9Transfection reagent (Roche) accordingly to manufacturer's protocol. The cells were maintained for three passages, as described above to ensure viral propagation to all cells. After confirmation of RCAS-inserts by western blot, DF1s (passage 4 or later) were used for injection into murine brain. Newborn N/tv-a;Ink4a/Arf$^{-/-}$ pups (P0-P1) were injected (Hamilton syringe #84877) with 1 µL of approximately $1\times10^5$ DF-1 cells infected with and producing relevant RCAS viruses suspended in serum-free DMEM (TrkB.T1 and shPTEN) (Ozawa, T., et al. (2014). Most human non-GCIMP glioblastoma subtypes evolve from a common proneural-like precursor glioma. *Cancer Cell* 26, 288-300). Simultaneous delivery of two RCAS viruses was performed by the injection of 1 µL of approximately $2\times10^5$ DF-1 cells mixed with equal ratio. Mice were monitored for the duration of the study (250 days) to check for tumor related symptoms such as palpable masses, lethargy, weight loss, seizure, hyperactivity, altered gait, poor grooming, macrocephaly, paralysis. Mice with severe hydrocephalus presumably due to injection trauma or an inflammatory response against the DF-1 cells were excluded from survival analysis in this study. All animal experiments were approved by and conducted in accordance with the Institutional Animal Care and Use Committee of Fred Hutchinson Cancer Research Center (protocol #50842).

Mouse Tissue Processing

Mouse tissue (including normal brains, tumor bearing brains, solid tumors) were removed, fixed in 10% neutral-buffered formalin for a minimum of 72 hours and embedded into paraffin blocks. 5 µm serial sections were cut from formalin-fixed paraffin embedded specimens and mounted on slides.

Immunohistochemistry

Immunohistochemical staining was performed on Sum formalin-fixed/paraffin-embedded tissue sections using a Discovery XT Ventana Automated Stainer (Ventana Medical Systems, Inc)., run using standard Ventana reagents a and Vector secondaries for staining with the TrkB.T1 SPEH1 D12 scFv-Fc fusion (Pattwell, S. S., et al. (2020). Neurotrophic Receptor Tyrosine Kinase 2 (NTRK2) Alterations in Low-Grade Gliomas: Report of a Novel Gene Fusion Partner in a Pilocytic Astrocytoma and Review of the Literature. *Case Rep Pathol* 2020, 5903863) at 1:500 and PTEN (Cell Signaling #9188, Lot #4) at 1:100 or TrkB (kinase specific against amino acid 810; abcam #ab18987, lot #GR3280550-2) at 1:250. All embryonic histology slides and human tissue microarray (BioMax, U.S. #BC001134b) slides were scanned using a Ventana DP200 slide scanning system (Roche Diagnostics) at 20× magnification. Digital images of different organ during mouse development were analyzed using the Fiji image analysis software as described previously (Haffner, M. C., et al. (2017). AIM1 is an actin-binding protein that suppresses cell migration and micrometastatic dissemination. *Nat Commun* 8, 142; Schindelin, J., et al. (2012). Fiji: an open-source platform for biological-image analysis. *Nat Methods* 9, 676-682). Staining intensities in human tumor tissues were assessed using a semi-quantitative H-score system by multiplying the intensity of the stain (0: no staining; 1: weak staining; 2: moderate staining; 3: intense staining) by the percentage (0 to 100) of cells showing that staining intensity (H-score range, 0 to 300) as described previously (Haffner, M. C., Chaux, A., et al. (2011). Global 5-hydroxymethylcytosine content is significantly reduced in tissue stem/progenitor cell compartments and in human cancers. Oncotarget 2, 627-637).

Flow Cytometry

Rodent tumors were harvested and resuspended as single cells in PBS/0.3% BSA. Cells were washed and incubated with the following antibodies: CD45-APC-Cy7 (Biolegend, clone 30-F11, catalog #103116, lot #B242535), CD3e-PE (BD, clone 145-2C11, catalog #553061, lot #22126), GR1-PerCP (BD, clone Ly-6G/Ly-6C, catalog #552093, lot #73108), TER119-APC (BD, clone Ter-119, catalog #557909, lot #42622), B220-Alexa 647 (BD, clone RA3-6B2, catalog #557683, lot #22218), CD4-PerCP (BD, clone L3T3, catalog #553654, lot #60912), and CD8a-FITC (BD, clone Ly-2, catalog #553030, lot #46675), as indicated. Cells were analyzed on a custom built LSR II flow cytometer (BD). Data compensation and analysis were performed by using noncommercial software developed in our laboratory (Wood, B. (2006). 9-color and 10-color flow cytometry in the clinical laboratory. *Arch Pathol Lab Med* 130, 680-690).

Soft Agar Colony Formation Assay

Lentiviral Production 293T packaging cells were seeded in 100 mm plates at a density of $3.8\times10^6$ cells per plate. 293T cells were supplemented with complete DMEM media (Dulbecco's Modified Eagle Media (ThermoScientific, catalog #11966025) containing 10% Fetal Bovine Serum (Fetal Bovine Serum (ThermoScientific, catalog #26140079) and 5% Penicillin/Streptomycin. 293T cells were split 3 times a week in order to maintain healthy density and incubated at 37° C. Once the optimal number of 293T 10 mm plates were produced, they were transfected with psPAX2 (Addgene, catalog #12260), pMD2.G (Addgene, catalog #12259), and the gene of interest containing pLJM1 lentiviral packaging plasmids (Addgene, catalog #91980) at concentrations of 1.3 pmol, 0.72 pmol, and 1.64 pmol. 293T cells were transfected using the ThermoFisher Lipofectamine 3000 transfection protocol (ThermoFisher, catalog #L3000001). The media was replaced after 18 hours in order to permit lentiviral production in transfection reagent free media.

Viral media was harvested after 48, 72, and 96 hours and replaced with fresh media after each harvest. The viral supernatant was filtered through 0.45 μm syringe filters Millex-HP Syringe Filter Unit 0.45 μm (Millipore Sigma, SLHP033RS) to remove cellular debris and other contaminants.

NIH-3T3 cells were seeded in 100 mm plates at a density of $2.2\times10^6$ cells per plate and supplemented with complete DMEM containing 10% calf serum (Calf Serum (Thermo-Scientific. catalog #16170086) and 5% Penicillin/Streptomycin. Once the NIH-3T3 plates reached optimal confluency, NIH-3T3 cells were supplemented with the viral harvest media and left to incubate for 24 hours. The viral harvest was then removed and fresh complete DMEM media with 2 μg/ml of puromycin. The NIH-3T3 cells were incubated for a week under these selection conditions until the population density rebounded to plate confluency.

Soft Agar Colony Formation Assay

Once the NIH-3T3 cells under each condition were confluent, the Soft Agar Colony Formation assay was initiated. A 3% agarose solution (Agarose; Guidechem, catalog number: 9012-36-6) was microwaved for 1 minute and stored in a 45° C. water bath in order to maintain its liquid state. The 3% agarose solution was aliquoted and diluted with complete DMEM media to yield a 0.6% agarose/media solution. This new mixture was poured into 6-well plates at 1 ml and allowed to solidify for 30 min. Aliquots of 0.6% solution were then diluted with the NIH-3T3 cell media suspension so that the solution was composed of 0.3% agarose and contained a concentration of $2\times10^3$ cells/ml. This solution was stored at 37° C. rather than 45° C. to prevent cell death. The solution was plated atop the now solid 0.6% agarose layer and allowed to solidify at room temperature for 1 hour.

The agarose suspension of cells was incubated at 37° C. for 30 days while supplemented with a 1 ml feeder layer of DMEM with 1 ug/ml of puromycin and 10% calf serum. After 30 days, the feeder layer was removed and a solution of 0.005% crystal violet dye was plated onto the agarose to darken the formed colonies. Colonies were photographed at 10× and 20× magnification and were counted at 4× magnification.

While illustrative embodiments have been illustrated and described, it will be appreciated that various changes can be made therein without departing from the spirit and scope of the invention.

---

The invention claimed is:

1. An antibody or antigen-binding derivative thereof, wherein the antibody or antigen-binding derivative specifically binds to a polypeptide with at least 80% identity to the amino acid sequence FVLFHKIPLDG (SEQ ID NO:1), wherein the antibody or antigen-binding fragment comprises a heavy chain variable region (VH) and a light chain variable region (VL), and wherein:

(i) the VH comprises complementarity determining regions, CDRH1, CDRH2, and CDRH3, corresponding to the amino acid residues 146-273 of SEQ ID NO: 2; and (ii) the VL comprises complementarity determining regions, CDRL1, CDRL2, and CDRL3, corresponding to the amino acid residues 21-129 of SEQ ID NO:2.

2. The antibody or antigen-binding derivative thereof of claim 1, wherein the polypeptide is in a C-terminal domain of a human tropomyosin receptor kinase B (TrkB) isoform.

3. The antibody or antigen-binding derivative thereof of claim 1, wherein the antibody derivative comprises an antigen binding antibody fragment.

4. The antibody or antigen-binding derivative thereof of claim 1, wherein the antibody derivative is a single-chain antibody.

5. A method of producing an antibody that binds a polypeptide with at least 80% identity to the sequence FVLFHKIPLDG (SEQ ID NO:1), the method comprising:

immunizing an antibody producing animal with a construct comprising the peptide with at least 80% identity to the sequence FVLFHKIPLDG (SEQ ID NO:1), wherein the animal has a genetic background that is null for a TrkB.T1 isoform, and isolating an antibody from the animal, wherein the antibody comprises a heavy chain variable region (VH) and a light chain variable region (VL), and wherein:

(i) the VH comprises complementarity determining regions, CDRH1, CDRH2, and CDRH3, corresponding to the amino acid residues 146-273 of SEQ ID NO: 2; and (ii) the VL comprises complementarity determining regions, CDRL1, CDRL2, and CDRL3, corresponding to the amino acid residues 21-129 of SEQ ID NO:2.

6. The method of claim 5, further comprising isolating one or more splenocytes from the animal.

7. The method of claim 6, comprising fusing a splenocyte obtained from the animal that produces an antibody that binds to the polypeptide with at least 80% identity to the sequence FVLFHKIPLDG (SEQ ID NO:1) with an immortal cell to produce a hybridoma.

8. A method of detecting the presence or elevated risk of a cancer in a subject, wherein the cancer is characterized by elevated levels of tropomyosin receptor kinase B (TrkB) isoform with a polypeptide with at least 80% identity to the sequence FVLFHKIPLDG (SEQ ID NO:1) at the C-terminal end, the method comprising:

contacting a biological sample obtained from the subject with the antibody or antibody derivative as recited in claim 1, and detecting binding of the antibody or antibody derivative to a component of the sample to determine a level of the TrkB isoform, wherein an elevated level of isoform TrkB isoform compared to a reference standard is indicative of the presence or risk of the cancer in the subject.

9. The method of claim 8, wherein the isoform is TrkB.T1.

10. The method of claim 8, wherein the cancer is characterized by expression of nestin.

11. The method of claim 8, wherein the cancer is a platelet-derived growth factor (PDGF)-driven cancer.

12. The method of claim 8, wherein the cancer is characterized by reduced expression of phosphatase and tensin homolog (PTEN).

13. The method of claim 8, wherein the cancer is a solid tumor.

14. The method of claim 8, wherein the cancer is a non-solid tumor, and wherein the non-solid tumor is a leukemia or lymphoma.

15. The method of claim 8, wherein the cancer is a pediatric cancer selected from Wilms tumor (WT), rhabdoid tumor (RT), neuroblastoma (NBL), and clear cell sarcoma of the kidney (CCSK).

16. The method of claim 8, wherein the reference standard is a level of the TrkB isoform in an equivalent biological sample from one or more healthy subjects.

17. The method of claim 8, wherein the reference standard is a level of full-length TrkB in the same biological sample or a similar biological sample as obtained from the subject.

* * * * *

SEQUENCE LISTING

```
<160> NUMBER OF SEQ ID NOS: 8

<210> SEQ ID NO 1
<211> LENGTH: 11
<212> TYPE: PRT
<213> ORGANISM: Homo sapiens

<400> SEQUENCE: 1

Phe Val Leu Phe His Lys Ile Pro Leu Asp Gly
1               5                   10

<210> SEQ ID NO 2
<211> LENGTH: 501
<212> TYPE: PRT
<213> ORGANISM: Artificial sequence
<220> FEATURE:
<223> OTHER INFORMATION: Synthetic

<400> SEQUENCE: 2
```

-continued

```
Met Glu Thr Asp Thr Leu Leu Leu Trp Val Leu Leu Leu Trp Val Pro
1               5                   10                  15

Gly Ser Thr Gly Gln Thr Val Val Thr Gln Glu Ser Ala Leu Thr Thr
                20                  25                  30

Ser Pro Gly Glu Thr Val Thr Leu Thr Cys Arg Ser Ser Thr Gly Ala
            35                  40                  45

Val Thr Thr Ser Asn Tyr Ala Asn Trp Val Gln Glu Lys Pro Asp His
        50                  55                  60

Leu Phe Thr Gly Leu Ile Gly Gly Ile Asn Asn Arg Ala Pro Gly Val
65                  70                  75                  80

Pro Ala Arg Phe Ser Gly Ser Leu Ile Gly Asp Lys Ala Val Leu Thr
                85                  90                  95

Ile Thr Gly Ala Gln Thr Glu Asp Glu Ala Ile Tyr Phe Cys Ala Leu
            100                 105                 110

Trp Tyr Ser Asn His Trp Val Phe Gly Gly Gly Thr Lys Leu Thr Val
        115                 120                 125

Leu Gly Gly Gly Gly Ser Gly Gly Gly Gly Ser Gly Gly Gly Gly Ser
    130                 135                 140

Gln Val Gln Leu Gln Gln Ser Gly Pro Glu Leu Ala Arg Pro Trp Ala
145                 150                 155                 160

Ser Val Lys Ile Ser Cys Gln Ala Phe Tyr Thr Phe Ser Arg Gly Ile
                165                 170                 175

His Phe Asp Ile Arg Asn Thr Met Tyr Trp Ile Gln Trp Val Lys Gln
            180                 185                 190

Arg Pro Gly Gln Gly Leu Glu Trp Ile Gly Ala Ile Tyr Pro Gly Asn
            195                 200                 205

Gly Asp Pro Thr Tyr Ser Gln Asn Phe Lys Asp Lys Ala Thr Leu Thr
        210                 215                 220

Ala Asp Lys Ser Ser Asn Thr Ala Tyr Met Gln Leu Ser Ser Leu Thr
225                 230                 235                 240

Ser Glu Asp Ser Ala Val Tyr Tyr Cys Ala Arg Tyr Asp Tyr Gly Gly
            245                 250                 255

Gly Phe Thr Tyr Trp Gly Gln Gly Thr Leu Val Thr Val Ser Ala Gly
            260                 265                 270

Ser Ala Pro Ser Thr Cys Ser Lys Pro Thr Cys Pro Pro Pro Glu Leu
        275                 280                 285

Leu Gly Gly Pro Ser Val Phe Ile Phe Pro Pro Lys Pro Lys Asp Thr
    290                 295                 300

Leu Met Ile Ser Arg Thr Pro Glu Val Thr Cys Val Val Val Asp Val
305                 310                 315                 320

Ser Gln Asp Asp Pro Glu Val Gln Phe Thr Trp Tyr Ile Asn Asn Glu
            325                 330                 335

Gln Val Arg Thr Ala Arg Pro Pro Leu Arg Glu Gln Gln Phe Asn Ser
            340                 345                 350

Thr Ile Arg Val Val Ser Thr Leu Pro Ile Thr His Gln Asp Trp Leu
        355                 360                 365

Arg Gly Lys Glu Phe Lys Cys Lys Val His Asn Lys Ala Leu Pro Ala
        370                 375                 380

Pro Ile Glu Lys Thr Ile Ser Lys Ala Arg Gly Gln Pro Leu Glu Pro
385                 390                 395                 400

Lys Val Tyr Thr Met Gly Pro Pro Arg Glu Glu Leu Ser Ser Arg Ser
                405                 410                 415
```

```
Val Ser Leu Thr Cys Met Ile Asn Gly Phe Tyr Pro Ser Asp Ile Ser
            420                 425                 430

Val Glu Trp Glu Lys Asn Gly Lys Ala Glu Asp Asn Tyr Lys Thr Thr
            435                 440                 445

Pro Ala Val Leu Asp Ser Asp Gly Ser Tyr Phe Leu Tyr Asn Lys Leu
    450                 455                 460

Ser Val Pro Thr Ser Glu Trp Gln Arg Gly Asp Val Phe Thr Cys Ser
465                 470                 475                 480

Val Met His Glu Ala Leu His Asn His Tyr Thr Gln Lys Ser Ile Ser
                485                 490                 495

Arg Ser Pro Gly Lys
            500

<210> SEQ ID NO 3
<211> LENGTH: 19
<212> TYPE: DNA
<213> ORGANISM: Artificial sequence
<220> FEATURE:
<223> OTHER INFORMATION: Synthetic

<400> SEQUENCE: 3
caggtagaac ggagcagca                                           19

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
ggttagcaga gggcaatgga                                          20

<210> SEQ ID NO 5
<211> LENGTH: 20
<212> TYPE: DNA
<213> ORGANISM: Artificial sequence
<220> FEATURE:
<223> OTHER INFORMATION: Synthetic

<400> SEQUENCE: 5
ttccttgccg agtgctacaa                                          20

<210> SEQ ID NO 6
<211> LENGTH: 18
<212> TYPE: DNA
<213> ORGANISM: Artificial sequence
<220> FEATURE:
<223> OTHER INFORMATION: Synthetic

<400> SEQUENCE: 6
tcgtgctgga ggttggtc                                            18

<210> SEQ ID NO 7
<211> LENGTH: 24
<212> TYPE: DNA
<213> ORGANISM: Artificial sequence
<220> FEATURE:
<223> OTHER INFORMATION: Synthetic

<400> SEQUENCE: 7
tcaacagcaa ctcccactct tcca                                     24
```

-continued

```
<210> SEQ ID NO 8
<211> LENGTH: 24
<212> TYPE: DNA
<213> ORGANISM: Artificial sequence
<220> FEATURE:
<223> OTHER INFORMATION: Synthetic

<400> SEQUENCE: 8
accctgttgc tgtagccgta ttca                                        24
```